(12) United States Patent
Korneluk et al.

(10) Patent No.: US 6,946,544 B2
(45) Date of Patent: Sep. 20, 2005

(54) XAF GENES AND POLYPEPTIDES: METHODS AND REAGENTS FOR MODULATING APOPTOSIS

(75) Inventors: Robert G. Korneluk, Ottawa (CA); Katsuyuki Tamai, Nagano (JP); Peter Liston, Ottawa (CA); Alexander E. MacKenzie, Ottawa (CA)

(73) Assignee: Aegera Therapeutics Inc., Quebec (CA)

( * ) Notice: Subject to any disclaimer, the term of this patent is extended or adjusted under 35 U.S.C. 154(b) by 194 days.

(21) Appl. No.: 10/288,273

(22) Filed: Nov. 5, 2002

(65) Prior Publication Data

US 2003/0215824 A1 Nov. 20, 2003

Related U.S. Application Data

(60) Continuation of application No. 09/616,614, filed on Jul. 14, 2000, now Pat. No. 6,495,339, which is a division of application No. 09/100,391, filed on Jun. 19, 1998, now Pat. No. 6,107,088.
(60) Provisional application No. 60/056,338, filed on Aug. 18, 1997, provisional application No. 60/054,491, filed on Aug. 1, 1997, and provisional application No. 60/052,402, filed on Jul. 14, 1997.

(51) Int. Cl.[7] .............................................. C07K 14/47
(52) U.S. Cl. ..................................................... 530/350
(58) Field of Search ............................. 530/350; 514/12

(56) References Cited

U.S. PATENT DOCUMENTS

| 5,585,479 A | 12/1996 | Hoke et al. |
| 6,187,667 B1 | 2/2001 | Shan et al. |

FOREIGN PATENT DOCUMENTS

| WO | WO 97/06182 | 2/1997 |

OTHER PUBLICATIONS

Caldwell, Yakubutsu Dotai (Xenobiotic Metabolism and Disposition), 1996, vol. 11, No. 1, pp. 119–125.*
Boldin et al., "Involvement of MACH, a Novel MORT1/FADD–Interacting Protease, in Fas/APO–1 and TNF Receptor–Induced Death," *CELL* 85:803–815 (1996).
Boss et al., "The Cyclosporin A–sensitive Nuclear Factor of Activated T Cells (NFAT) Proteins Are Expressed in Vascular Smooth Muscle Cells," *The Journal of Biological Chemistry* 273(31):19664–19671 (1998).
Cheng et al., "Tank, A Co–inducer with TRAF2 of TNF–and CD40L–mediated NF–KB Activation," *Genes and Development* 10:963–973 (1996).
Chinnaiyan et al., "FADD, A Novel Death Domain–Containing Protein, Interacts with the Death Domain of Fas and Initiates Apoptosis," *Cell* 81:505–512 (1995).
Chinnaiyan et al., "FADD/MORT1 is a Common Mediator of CD95 (Fas/APO–1) and Tumor Necrosis Factor Receptor–induced Apoptosis," *The Journal of Biological Chemistry* 271:4961–4965 (1996).
Clem et al., "Anti–apoptotic genes of baculovirues," *Cell Death and Differentiation* 3:9–16 (1996).
Crabtree, "Calcium, Calcineurin, and the Control of Transcription," *The Journal of Biological Chemistry* 276(4):2313–2316 (2001).
Database Nucleotide and Protein "*H. Sapiens* mRNA for XIAP Associated Factor–1," Database Accession No. X99699 XP002172934.
Database Nucleotide and Protein "EST70445 T–cell Lymphoma *Homo sapiens* cDNA 5' End Similar to EST Containing L1 Repeat," Database Accession No. AA361201 XP002172935.
Database Nucleotide and Protein "Soares Fetal Liver Spleen 1NFLS *Homo sapiens* cDNA Clone IMAGE:66510 3' Similar to Contains L1 Repetitive Element, mRNA Sequence EST," Database Accession No. T66962 XP002172936.
Database Nucleotide and Protein "Soares Fetal Liver Spleen 1NFLS *Homo sapiens* cDNA Clone IMAGE:21864 5' mRNA Sequence EST," Database Accession No. H66704 XP002172937.
de la Pompa et al., "Role of the NF–ATc Transcription Factor in Morphogenesis of Cardiac Valves and Septum," *Nature* 392:182–186 (1998).
Farahani et al. "Genomic Organization and Primary Characterization of *miap*–3: The Murine Homologue Human X–Linked IAP," *Genomics* 42:514–518 (1997).
Gehr et al., "Both Tumor Necrosis Factor Receptor Types Mediate Proliferative Singals in Human Mononuclear Cell Activation," *J. Immunol.* 149:911–917 (1992).
Grell et al., "TR60 and TR80 Tumor Necrosis Factor (TNF)–Receptors Can Independently Mediate Cytolysis," *Lymphokine Cytokine Res.* 12:143–148 (1993).
Heller et al., "The p70 Tumor Necrosis Factor Receptor Mediates Cytotoxicity," *Cell* 70:47–56 (1992).
Hsu et al., The TNF Receptor 1–Associated Protein TRADD Signals Cell Death and NF– B Activation, *Cell* 81:495–504 (1995).
Hsu et al., "TRADD–TRAF2 and TRADD–FADD Interactions Define Two Distinct TNF Receptor 1 Signal Transduction Pathways," *Cell* 84:299–308 (1996).

(Continued)

Primary Examiner—Terry McKelvey
(74) Attorney, Agent, or Firm—Kristina Bieker-Brady; Clark & Elbing, LLP

(57) ABSTRACT

The invention provides novel XAF nucleic acid sequences. Also provided are XAF polypeptides, anti-XAF antibodies, and methods for modulating apoptosis and detecting compounds which modulate apoptosis.

11 Claims, 51 Drawing Sheets

OTHER PUBLICATIONS

John et al., "The Role of Matrix Metalloproteinases in Tumor Angiogenesis and Tumor Metastasis," *Pathology Oncology Research* 7(1):14–23 (2001).

Kitson et al., "A Death–Domain–Containing Receptor That Mediates Apoptosis," *Nature* 384:372–375 (1996).

Liston et al., "Genomic Characterization of the Mouse Inhibitor of Apoptosis Protein 1 and 2 Genes," *Genomics* 46:495–503 (1997).

Liston et al., "Suppression of Apoptosis in Mammalian Cells by NAIP and a Related Family of IAP Genes" *Nature* 379:349–353 (1996).

López–Rodríguez et al., "NFAT5, A Constitutively Nuclear NFAT Protein That Does Not Cooperate With Fos and Jun," *Proc. Natl. Acad. Sci. USA* 96:7214–7219 (1999).

Miyakawa et al., "Tonicity–Responsive Enhancer Binding Protein, A Rel–like Protein That Stimulates Transcription in Response to Hypertonicity," *Proc. Natl. Acad. Sci. USA* 96:2538–2542 (1999).

Müller et al. "Involvement of Chemokine Receptors in Breast Cancer Metastasis," *Nature* 410:50–56 (2001).

Muzio et al., "FLICE, A Novel FADD–Homologous ICE/CED–3–like Protease, Is Recruited to the CD95 (Fas/APO–1) Death–Inducing Signaling Complex," *CELL* 85:817–827 (1996).

Rabinovitz et al., "The Integrin $\alpha 6\beta 4$ Functions in Carcinoma Cell Migration on Laminin–1 By Mediating the Formation and Stabilization of Actin–containing Motility Structures," *The Journal of Cell Biology* 139(7):1873–1884 (1997).

Rajean–Separovic et al., "Assignment of Human Inhibitor of Apoptosis Protein (IAP) Genes *xiap, naip–1*, and *hiap–2* to Chromosomes Xq25 and 11q22–q23 by Fluorescence in Situ Hybridization," *Genomics* 37:404–406 (1996).

Rothe et al., "The TNFR2–TRAF Signaling Complex Contains Two Novel Proteins Related to Baculoviral Inhibitor of apoptosis Proteins", *Cell* 83:1243–1252 (1995).

Rothe et al., "TRAF2–mediated activation of NF–kB by TNF receptor 2 and CD40," *Science* 269:1424–1427 (1995).

Roundtable Discussion, Nature Biotech, Conference 1997, *Nature Biotechnology* 15:522–528 (1997).

Roy et al., "The Gene for Neuronal Apoptosis Inhibitory Protein is Partially Deleted in Individuals with Spinal Muscular Atrophy," *Cell* 80:167–178 (1995).

Shaw et al., "Activation of Phosphoinositide 3–OH Kinase by the $\alpha 6\beta 4$ Integrin Promotes Carcinoma Invasion," *Cell* 91:949–960 (1997).

Spengler, et al., "Regulation of Apoptosis and Cell Cycle Arrest by Zac1, A Novel Zinc Finger Protein Expressed In the Pituitary Gland and the Brain," *The EMBO Journal* 16:2814–2825 (1997).

Tartagalia et al., "The Two Different Receptors For Tumor Necrosis Factor Mediate Distinct Cellular Respones," *Proc. Natl. Acad. Sci. USA* 88:9292–9296 (1994).

Tartaglia et al., "Stimulation of Human T–Cell Proliferation by Specific Activation of the 75– Da Tumor Necrosis Factor Receptor," *J. Immunol.* 151:4637–4641 (1993).

Toji, Yano, and Tamai, "Identification of a novel XIAP associated protein," *GenEMBL* X99699 (1997).

Trama et al., "The NFAT–Related Protein NFATL1 (TonEBP/NFAT5) Is Inducted Upon T Cell Activation in a Calcineurin–Dependent Manner," *The Journal of Immunology* p. 4884–4894 (2000).

Trusolino et al., "A Signaling Adapter Function for $\alpha 6\beta 4$ Integrin in the Control of HGF–Dependent Invasive Growth," *Cell* 107:643–654 (2001).

\* cited by examiner

```
ATGGAAGGAGACTTCTCGGTGTGCAGGAACTGTAAAAGACATGTAGTCTCTGCCAACTTC    60
 M  E  G  D  F  S  V  C  R  N  C  K  R  H  V  V  S  A  N  F

ACCCTCCATGAGGCTTACTGCCTGCGGTTCCTGGTCCTGTGTCCGGAGTGTGAGGAGCCT   120
 T  L  H  E  A  Y  C  L  R  F  L  V  L  C  P  E  C  E  E  P

GTCCCCAAGGAAACCATGGAGGAGCACTGCAAGCTTGAGCACCAGCAGGTTGGGTGTACG   180
 V  P  K  E  T  M  E  E  H  C  K  L  E  H  Q  Q  V  G  C  T

ATGTGTCAGCAGAGCATGCAGAAGTCCTCGCTGGAGTTTCATAAGGCCAATGAGTGCCAG   240
 M  C  Q  Q  S  M  Q  K  S  S  L  E  F  H  K  A  N  E  C  Q

GAGCGCCCTGTTGAGTGTAAGTTCTGCAAACTGGACATGCAGCTCAGCAAGCTGGAGCTC   300
 E  R  P  V  E  C  K  F  C  K  L  D  M  Q  L  S  K  L  E  L

CACGAGTCCTACTGTGGCAGCCGGACAGAGCTCTGCCAAGGCTGTGGCCAGTTCATCATG   360
 H  E  S  Y  C  G  S  R  T  E  L  C  Q  G  C  G  Q  F  I  M

CACCGCATGCTCGCCCAGCACAGAGATGTCTGTCGGAGTGAACAGGCCCAGCTCGGGAAA   420
 H  R  M  L  A  Q  H  R  D  V  C  R  S  E  Q  A  Q  L  G  K

GGGGAAAGAATTTCAGCTCCTGAAAGGGAAATCTACTGTCATTATTGCAACCAAATGATT   480
 G  E  R  I  S  A  P  E  R  E  I  Y  C  H  Y  C  N  Q  M  I

CCAGAAAATAAGTATTTCCACCATATGGGTAAATGTTGTCCAGACTCAGAGTTTAAGAAA   540
 P  E  N  K  Y  F  H  H  M  G  K  C  C  P  D  S  E  F  K  K

CACTTTCCTGTTGGAAATCCAGAAATTCTTCCTTCATCTCTTCCAAGTCAAGCTGCTGAA   600
 H  F  P  V  G  N  P  E  I  L  P  S  S  L  P  S  Q  A  A  E

AATCAAACTTCCACGATGGAGAAAGATGTTCGTCCAAAGACAAGAAGTATAAACAGATTT   660
 N  Q  T  S  T  M  E  K  D  V  R  P  K  T  R  S  I  N  R  F

CCTCTTCATTCTGAAAGTTCATCAAAGAAAGCACCAAGAAGCAAAAACAAAACCTTGGAT   720
 P  L  H  S  E  S  S  S  K  K  A  P  R  S  K  N  K  T  L  D

CCACTTTTGATGTCAGAGCCCAAGCCCAGGACCAGCTCCCCTAGAGGAGATAAAGCAGCC   780
 P  L  L  M  S  E  P  K  P  R  T  S  S  P  R  G  D  K  A  A

TATGACATTCTGAGGAGATGTTCTCAGTGTGGCATCCTGCTTCCCCTGCCGATCCTAAAT   840
 Y  D  I  L  R  R  C  S  Q  C  G  I  L  L  P  L  P  I  L  N

CAACATCAGGAGAAATGCCGGTGGTTAGCTTCATCAAAAAGGAAAACAAGTGAGAAATTT   900
 Q  H  Q  E  K  C  R  W  L  A  S  S  K  R  K  T  S  E  K  F

CAGCTAGATTTGGAAAAGGAAAGGTACTACAAATTCAAAAGATTTCACTTTTAACACTGG   960
 Q  L  D  L  E  K  E  R  Y  Y  K  F  K  R  F  H  F  *

CATTCCTGCCTACTTGCTGTGGTGGTCTTGTGAAAGGTGATGGGTTTTATTCGTTGGGCT  1020
TTAAAAGAAAAGGTTTGGCAGAACTAAAAACAAAACTCACGTATCATCTCAATAGATACA  1080
GAAAAGGCTTTTGATAAAATTCAACTTGACTTCATGTTAAAAACCCTCAACAAACCAGGC  1140
GTCGAAGGAACATACCTCAAAATAATAAGAGCCATCTATGACAAAACCACAGCCAACATC  1200
ATACTGAATGAGCAAAAGCTGGAGCATTACTCTTGAGAAGTAGAACAAGGCACTTCAGTC  1260
CTATTCAACATAGTACTGGAAGTCTCGCCACAGCAATCAGGCAAGAGAAAGAAGTAAAAG  1320
GCACCC
```

Fig. 1

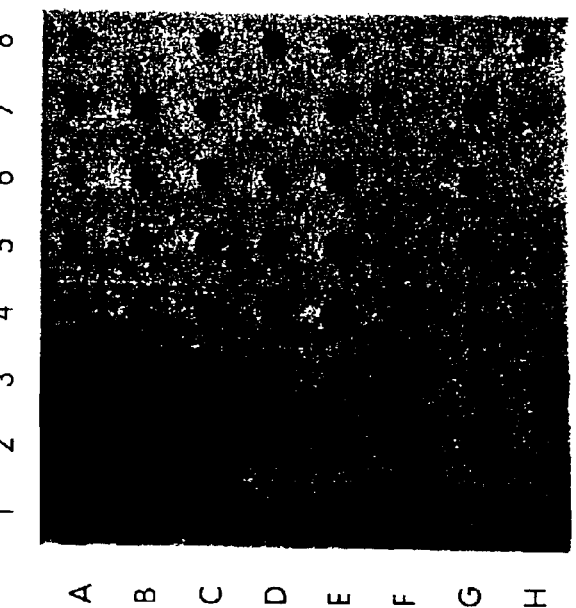

Fig. 4B

| | 1 | 2 | 3 | 4 | 5 | 6 | 7 | 8 |
|---|---|---|---|---|---|---|---|---|
| A | WHOLE BRAIN | AMYGDALA | CAUDATE NUCLEUS | CERE-BELLUM | CEREBRAL CORTEX | FRONTAL LOBE | HIPPO-CAMPUS | MEDULLA OBLONGATA |
| B | OCCIPITAL LOBE | PUTAMEN | SUBSTANTIA NIGRA | TEMPORAL LOBE | THALAMUS | SUB-THALAMIC NUCLEUS | SPINAL CORD | |
| C | HEART | AORTA | SKELETAL MUSCLE | COLON | BLADDER | UTERUS | PROSTATE | STOMACH |
| D | TESTIS | OVARY | PANCREAS | PITUITARY GLAND | ADRENAL GLAND | THYROID GLAND | SALIVARY GLAND | MAMMARY GLAND |
| E | KIDNEY | LIVER | SMALL INTESTINE | SPLEEN | THYMUS | PERIPHERAL LEUKOCYTE | LYMPH NODE | BONE MARROW |
| F | APPENDIX | LUNG | TRACHEA | PLACENTA | | | | |
| G | FETAL BRAIN | FETAL HEART | FETAL KIDNEY | FETAL LIVER | FETAL SPLEEN | FETAL THYMUS | FETAL LUNG | |
| H | YEAST TOTAL RNA 100 ng | YEAST tRNA 100 ng | E. coli rRNA 100 ng | E. coli DNA 100 ng | POLY r(A) 100 ng | HUMAN Cot1 DNA 100 ng | HUMAN DNA 100 ng | HUMAN DNA 500 ng |

Fig. 4A

| DNA-BINDING DOMAIN HYBRID | ACTIVATION DOMAIN HYBRID | INTERACTION |
|---|---|---|
| XIAP | XAF-1 | + |
| HIAP 1 | XAF-1 | + |
| HIAP 2 | XAF-1 | + |
| TRAF 2 | XAF-1 | + |
| TRAF 4 | XAF-1 | − |
| VECTOR | XAF-1 | − |
| XAF-1 | XIAP | + |
| XAF-1 | HIAP 1 | − |
| XAF-1 | HIAP 2 | + |
| XAF-1 | TRAF 2 | + |
| XAF-1 | TRAF 4 | − |
| XAF-1 | VECTOR | − |

Fig. 34

```
   1 GCAGCTAGTGTGTCATTTCAGCGTTTCTCCTCTCGTCCCTGGAAGAGCTAAAGATGGCTG   60
                                                              M  A  E    3

61 AATTTCTAGATGACCAGGAAACTCGACTGTGTGACAACTGCAAAAAGAAATTCCTGTGT  120
   4  F  L  D  D  Q  E  T  R  L  C  D  N  C  K  K  E  I  P  V  F   23
                                  I
 121 TTAACTTTACCATCCATGAGATCCACTGTCAAAGGAACATTGGTATGTGTCCTACCTGTA 180
  24  N  F  T  I  H  E  I  H  C  Q  R  N  I  G  M  C  P  T  C  K   43

181 AGGAACCATTTCCCAAATCTGACATGGAGACTCACATGGCTGCAGAACACTGTCAGGTGA 240
  44  E  P  F  P  K  S  D  M  E  T  H  M  A  A  E  H  C  Q  V  T   63
                        II
 241 CCTGCAAATGTAACAAGAAGTTGGAGAAGAGGCTGTTAAAGAAGCATGAGGAGACTGAGT 300
  64  C  K  C  N  K  K  L  E  K  R  L  L  K  K  H  E  E  T  E  C   83
                         III
 301 GCCCTTTGCGGCTTGCTGTCTGCCAGCACTGTGATTTAGAACTTTCCATTCTAAACTGA  360
  84  P  L  R  L  A  V  C  Q  H  C  D  L  E  L  S  I  L  K  L  K  103
                            IV
 361 AGGAACATGAAGATTATTGTGGTGCCCGGACGGAACTATGTGGCAACTGTGGTCGCAATG 420
 104  E  H  E  D  Y  C  G  A  R  T  E  L  C  G  N  C  G  R  N  V  123
                                            V
 421 TCCTTGTGAAAGATCTGAAGACTCACCCTGAAGTTTGTGGGAGAGAGGGGGAGGAAAAGA 480
 124  L  V  K  D  L  K  T  H  P  E  V  C  G  R  E  G  E  E  K  R  143

481 GAAATGAGGTTGCCATACCTCCTAATGCATATGATGAATCTTGGGGTCAGGATGGAATCT 540
 144  N  E  V  A  I  P  P  N  A  Y  D  E  S  W  G  Q  D  G  I  W  163

541 GGATTGCATCCCAACTCCTCAGACAAATTGAGGCTCTGGACCCACCCATGAGGCTGCCGC 600
 164  I  A  S  Q  L  L  R  Q  I  E  A  L  D  P  P  M  R  L  P  R  183

601 GAAGGCCCCTGAGAGCCTTTGAATCAGATGTTTTCCACAATAGAACTACCAACCAAAGGA 660
 184  R  P  L  R  A  F  E  S  D  V  F  H  N  R  T  T  N  Q  R  N  203

661 ACATTACAGCCCAGGTTTCAATTCAGAATAATCTGTTTGAAGAACAAGAGAGGCAGGAAA 720
 204  I  T  A  Q  V  S  I  Q  N  N  L  F  E  E  Q  E  R  Q  E  R  223

721 GGAATAGAGGCCAACAGCCCCCCAAAGAGGGTGGTGAAGAGAGTGCAAACTTGGACTTCA 780
 224  N  R  G  Q  Q  P  P  K  E  G  G  E  E  S  A  N  L  D  F  M  243

781 TGTTGGCCCTAAGTCTGCAAAATGAAGGCCAAGCCTCCAGTGTGGCAGAGCAGGACTTCT 840
 244  L  A  L  S  L  Q  N  E  G  Q  A  S  S  V  A  E  Q  D  F  W  263

841 GGAGGGCCGTATGTGAGGCCGACCAGTCTCATGGCGGTCCCAGGTCTCTCAGTGACATAA 900
 264  R  A  V  C  E  A  D  Q  S  H  G  G  P  R  S  L  S  D  I  K  283

901 AGGGTGCAGCTGACGAGATCATGTTGCCTTGTGAATTTTGTGAGGAGCTCTACCCAGAGG 960
 284  G  A  A  D  E  I  M  L  P  C  E  F  C  E  E  L  Y  P  E  E  303
                                        VI
 961 AACTGCTGATTGACCATCAGACAAGCTGTAACCCTTCACGTGCCTTACCTTCACTCAATA 1020
 304  L  L  I  D  H  Q  T  S  C  N  P  S  R  A  L  P  S  L  N  T  323

1021 CTGGCAGCTCTTCCCCCAGAGGGGTGGAGGAACCTGATGTCATCTTCCAGAACTCCTTGC 1080
 324  G  S  S  S  P  R  G  V  E  E  P  D  V  I  F  Q  N  S  L  Q  343

1081 AACAGGCTGCAAGTAACCAGTTAGACTCTTTGATGGGCCTGAGCAATTCACACCCTGTGG 1140
 344  Q  A  A  S  N  Q  L  D  S  L  M  G  L  S  N  S  H  P  V  E  363

1141 AGGAGAGCATCATTATCCCATGTGAATTCTGTGGGGTACAGCTGGAAGAGGAGGTGCTGT 1200
 364  E  S  I  I  I  P  C  E  F  C  G  V  Q  L  E  E  E  V  L  F  383
                                  VII
1201 TCCATCACCAGGACCAGTGTGACCAACGCCCAGCCACTGCAACCAACCATGTGACAGAGG 1260
 384  H  H  Q  D  Q  C  D  Q  R  P  A  T  A  T  N  H  V  T  E  G  403

1261 GGATTCCTAGACTGGATTCCCAGCCTCAAGAGCCCCTTCCCCTTGTTTTTA          1311
 404  I  P  R  L  D  S  Q  P  Q  E  P  L  P  L  V  F            420
```

Fig. 35

```
   1 TGGGTGCCAGCCCAGCTCTCCTTGTGTGCCGAAGCTCAGCAACTCAGACAGCCAGGACAT   60
  61 CCAGGGGCGGAATCGAGACAGCCAGAATGGGGCCATAGCCCCTGGGCACGTTTCAGTGAT  120
 121 TCGCCCTCCTCAAAATCTCTACCCAGAAAACATTGTGCCCTCTTTCTCCCGTGGGCCTTC  180
 181 AGGGAGATACGGAGCTAGTGGTAGGAGTGAAGGTGGCAGGAATTCCCGGGTCACCCCTGC  240
 241 AGCTGCCAACTACCGCAGCAGAACTGCAAAGGCAAAGCCTTCCAAGCAACAGGGAGCTGG  300
 301 GGATGCAGAAGAGGAAGAGGAGGAGTAATGGTGTCTCCAGAGACTTTACATCGGTTCCTG  360
 361 TCTTCTGTGCACAGCAGCACTTGCCGCTGTGCAGGCCCACCTCTTTGGCTCTTTGGGTGG  420
 421 GAGAGTTTTTCCAGATTTTAGATTTTTCTAGGTTATGGCCATTTTGTGTCTTTTGAGGTT  480
 481 GTGCTGTGGGGGTTTGGGTTTGAGGGAAGGGAGCAGGGTGGCGGTTGAGGAACGCTTCAG  540
 541 CCTTAGCTGCTACCTTTCGGCAGCAGTGAAATACAAGCTGCAGCCTCGGCTGCCAGGGCT  600
 601 CCCTTTTGACTTATTGTCGCCACTGCCCCTTGGTGCTGTGTGGTCCCAGTGGAAGGAGGG  660
 661 GAAGATTTTGGAAACCTGGTAGCCACCAGTAAGGTGATTCTCTGCCCTGTTGGGGCCTAA  720
 721 ATTTGGGGCTTTTGGGCAACCTCTCCGTGTACTGCGTCTGTCCACACTCGATTGGGCCC  780
 781 CAGGTGTGTATGAGGCGCTCTGGTAAGGTGCTCAGGCCAGTTGCAATGTCTGTCAGTAAC  840
 841 GAGGCTTTTGATGTGTTGAGCTGGAGGTGAGTGGACCGGGGGCTGTGTTTTAAGCTGCTT  900
 901 CCTTGGCATTTGGCATCACTGCCTTCTGTTCCGGGGGAGCATGGATCTTTTGTCCTCAC  960
 961 TGCTTTCTAATGGGGAGGGCTGAGGGCTCCCTGTCCCCACAGCAGGTATGGTTGCTCTGC 1020
1021 CCCAGCCCCACACTTGCTCTGAAAACCAAGTGTCAGAGCCCCTTCCCCTTGTTTTTATTT 1080
1081 TACTGTTATAATAATTATTAACTTCCTTGTAATAGAAATAAAGTTTGTACTTGGAAAAAA 1140
1141 AAAAAAAAAAAAAAAAAAAAAAAAAAAA                                 1169
```

Fig. 36

```
      GCAGCTAGTGTGTCATTTCAGCGTTTCTCCTCTCGTCCCTGGAAGAGCAAAGATGGCTG
   1  ---------+---------+---------+---------+---------+---------+  60
   c                                                          M A E  -
      AATTTCTAGATGACCAGGAAACTCGACTGTGTGACAACTGCAAAAAAGAAATTCCTGTGT
  61  ---------+---------+---------+---------+---------+---------+ 120
   c   F L D D Q E T R L C D N C K K E I P V F                      -
      TTAACTTTACCATCCATGAGATCCACTGTCAAAGGAACATTGGTATGTGTCCTACCTGTA
 121  ---------+---------+---------+---------+---------+---------+ 180
   c   N F T I H E I H C Q R N I G M C P T C K                      -
      AGGAACCATTTCCCAAATCTGACATGGAGACTCACATGGCTGCAGAACACTGTCAGGTGA
 181  ---------+---------+---------+---------+---------+---------+ 240
   c   E P F P K S D M E T H M A A E H C Q V T                      -
      CCTGCAAATGTAACAAGAAGTTGGAGAAGAGGCTGTTAAAGAAGCATGAGGAGACTGAGT
 241  ---------+---------+---------+---------+---------+---------+ 300
   c   C K C N K K L E K R L L K K H E E T E C                      -
      GCCCTTTGCGGCTTGCTGTCTGCCAGCACTGTGATTTAGAACTTTCCATTCTCAAACTGA
 301  ---------+---------+---------+---------+---------+---------+ 360
   c   P L R L A V C Q H C D L E L S I L K L K                      -
      AGGAACATGAAGATTATTGTGGTGCCCGGACGGAACTATGTGGCAACTGTGGTCGCAATG
 361  ---------+---------+---------+---------+---------+---------+ 420
   c   E H E D Y C G A R T E L C G N C G R N V                      -
      TCCTTGTGAAAGATCTGAAGACTCACCCTGAAGTTTGTGGGAGAGAGGGGGAGGAAAAGA
 421  ---------+---------+---------+---------+---------+---------+ 480
   c   L V K D L K T H P E V C G R E G E E K R                      -
      GAAATGAGGTTGCCATACCTCCTAATGCATATGATGAATCTTGGGGTCAGGATGGAATCT
 481  ---------+---------+---------+---------+---------+---------+ 540
   c   N E V A I P P N A Y D E S W G Q D G I W                      -
      GGATTGCATCCCAACTCCTCAGACAAATTGAGGCTCTGGACCCACCCATGAGGCTGCCGC
 541  ---------+---------+---------+---------+---------+---------+ 600
   c   I A S Q L L R Q I E A L D P P M R L P R                      -
      GAAGGCCCCTGAGAGCCTTTGAATCAGATGTTTTCCACAATAGAACTACCAACCAAAGGA
 601  ---------+---------+---------+---------+---------+---------+ 660
   c   R P L R A F E S D V F H N R T T N Q R N                      -
      ACATTACAGCCCAGGTTTCAATTCAGAATAATCTGTTTGAAGAACAAGAGAGGCAGGAAA
 661  ---------+---------+---------+---------+---------+---------+ 720
   c   I T A Q V S I Q N N L F E E Q E R Q E R                      -
      GGAATAGAGGCCAACAGCCCCCCAAAGAGGGTGGTGAAGAGAGTGCAAACTTGGACTTCA
 721  ---------+---------+---------+---------+---------+---------+ 780
   c   N R G Q Q P P K E G G E E S A N L D F M                      -
      TGTTGGCCCTAAGTCTGCAAAATGAAGGCCAAGCCTCCAGTGTGGCAGAGCAGGACTTCT
 781  ---------+---------+---------+---------+---------+---------+ 840
   c   L A L S L Q N E G Q A S S V A E Q D F W                      -
      GGAGGGCCGTATGTGAGGCCGACCAGTCTCATGGCGGTCCCAGGTCTCTCAGTGACATAA
 841  ---------+---------+---------+---------+---------+---------+ 900
   c   R A V C E A D Q S H G G P R S L S D I K                      -
      AGGGTGCAGCTGACGAGATCATGTTGCCTTGTGAATTTTGTGAGGAGCTCTACCCAGAGG
 901  ---------+---------+---------+---------+---------+---------+ 960
   c   G A A D E I M L P C E F C E E L Y P E E                      -
      AACTGCTGATTGACCATCAGACAAGCTGTAACCCTTCACGTGCCTTACCTTCACTCAATA
 961  ---------+---------+---------+---------+---------+---------+ 1020
   c   L L I D H Q T S C N P S R A L P S L N T                      -
      CTGGCAGCTCTTCCCCCAGAGGGGTGGAGGAACCTGATGTCATCTTCCAGAACTTCTTGC
1021  ---------+---------+---------+---------+---------+---------+ 1080
   c   G S S S P R G V E E P D V I F Q N F L Q                      -
```

Fig. 37A-1

```
      AACAGGCTGCAAGTAACCAGTTAGACTCTTTGATGGGCCTGAGCAATTCACACCCTGTGG
1081  ------------+---------+---------+---------+---------+---------+ 1140
   c     Q  A  A  S  N  Q  L  D  S  L  M  G  L  S  N  S  H  P  V  E -
      AGGAGAGCATCATTATCCCATGTGAATTCTGTGGGGTACAGCTGGAAGAGGAGGTGCTGT
1141  ------------+---------+---------+---------+---------+---------+ 1200
   c     E  S  I  I  P  C  E  F  C  G  V  Q  L  E  E  E  V  L  F -
      TCCATCACCAGGACCAGTGTGACCAACGCCCAGCCACTGCAACCAACCATGTGACAGAGG
1201  ------------+---------+---------+---------+---------+---------+ 1260
   c     H  H  Q  D  Q  C  D  Q  R  P  A  T  A  T  N  H  V  T  E  G -
      GGATTCCTAGACTGGATTCCCAGCCTCAAGAGACCCCACCAGAGCTGCCCAGGAGGCGTG
1261  ------------+---------+---------+---------+---------+---------+ 1320
   c     I  P  R  L  D  S  Q  P  Q  E  T  P  P  E  L  P  R  R  R  V -
      TCAGACACCAGGGAGACCTGTCTTCTGGTTACCTGGATGATACTAAGCAGGAAACAGCTA
1321  ------------+---------+---------+---------+---------+---------+ 1380
   c     R  H  Q  G  D  L  S  S  G  Y  L  D  D  T  K  Q  E  T  A  N -
      ATGGGCCCACCTCCTGTCTGCCTCCCAGCCGACCCATTAACAATATGACAGCTACCTATA
1381  ------------+---------+---------+---------+---------+---------+ 1440
   c     G  P  T  S  C  L  P  P  S  R  P  I  N  N  M  T  A  T  Y  N -
      ACCAGCTATCGAGATCAACATCAGGCCCCAGACCTGGGTGCCAGCCCAGCTCTCCTTGTG
1441  ------------+---------+---------+---------+---------+---------+ 1500
   c     Q  L  S  R  S  T  S  G  P  R  P  G  C  Q  P  S  S  P  C  V -
      TGCCGAAGCTCAGCAACTCAGACAGCCAGGACATCCAGGGGCGGAATCGAGACAGCCAGA
1501  ------------+---------+---------+---------+---------+---------+ 1560
   c     P  K  L  S  N  S  D  S  Q  D  I  Q  G  R  N  R  D  S  Q  N -
      ATGGGGCCATAGCCCCTGGGCACGTTTCAGTGATTCGCCCTCCTCAAAATCTCTACCCAG
1561  ------------+---------+---------+---------+---------+---------+ 1620
   c     G  A  I  A  P  G  H  V  S  V  I  R  P  P  Q  N  L  Y  P  E -
      AAAACATTGTGCCCTCTTTCTCCCCTGGGCCTTCAGGGAGATACGGAGCTAGTGGTAGGA
1621  ------------+---------+---------+---------+---------+---------+ 1680
   c     N  I  V  P  S  F  S  P  G  P  S  G  R  Y  G  A  S  G  R  S -
      GTGAAGGTGGCAGGAATTCCCGGGTCACCCCTGCAGCTGCCAACTACCGCAGCAGAACTG
1681  ------------+---------+---------+---------+---------+---------+ 1740
   c     E  G  G  R  N  S  R  V  T  P  A  A  A  N  Y  R  S  R  T  A -
      CAAAGGCAAAGCCTTCCAAGCAACAGGGAGCTGGGGATGCAGAAGAGGAAGAGGAGGAGT
1741  ------------+---------+---------+---------+---------+---------+ 1800
   c     K  A  K  P  S  K  Q  Q  G  A  G  D  A  E  E  E  E  E  *  -
      AATGGTGTCTCCAGAGACTTTACATCGGTTCCTGTCTTCTGTGCACAGCAGCACTTGCCG
1801  ------------+---------+---------+---------+---------+---------+ 1860
   c
      CTGTGCAGGCCCACCTCTTTGGCTCTTTGGGTGGGAGAGTTTTTCCAGATTTTAGATTTT
1861  ------------+---------+---------+---------+---------+---------+ 1920
   c
      TCTAGGTTATGGCCATTTTGTGTCTTTTGAGGTTGTGCTGTGGGGGTTTGGGTTTGAGGG
1921  ------------+---------+---------+---------+---------+---------+ 1980
   c
      AAGGGAGCAGGGTGGCGGTTGAGGAACGCTTCAGCCTTAGCTGCTACCTTTCGGCAGCAG
1981  ------------+---------+---------+---------+---------+---------+ 2040
   c
      TGAAATACAAGCTGCAGCCTCGGCTGCCAGGGCTCCCTTTTGACTTATTGTCGCCACTGC
2041  ------------+---------+---------+---------+---------+---------+ 2100
   c
      CCCTTGGTGCTGTGTGGTCCCAGTGGAAGGAGGGGAAGATTTTGGAAACCTGGTAGCCAC
2101  ------------+---------+---------+---------+---------+---------+ 2160
   c
```

Fig. 37A-2

```
  1 GCAGCTAGTGTGTCATTTCAGCGTTTCTCCTCTCGTCCCTGGAAGAGCTA 50
    ||||||||||||||||||||||||||||||||||||||||||||||||||
  1 GCAGCTAGTGTGTCATTTCAGCGTTTCTCCTCTCGTCCCTGGAAGAGCTA 50

51 AAGATGGCTGAATTTCTAGATGACCAGGAAACTCGACTGTGTGACAACTG 100
    ||||||||||||||||||||||||||||||||||||||||||||||||||
 51 AAGATGGCTGAATTTCTAGATGACCAGGAAACTCGACTGTGTGACAACTG 100

101 CAAAAAGAAATTCCTGTGTTTAACTTTACCATCCATGAGATCCACTGTC 150
    ||||||||||||||||||||||||||||||||||||||||||||||||||
101 CAAAAAGAAATTCCTGTGTTTAACTTTACCATCCATGAGATCCACTGTC 150

151 AAAGGAACATTGGTATGTGTCCTACCTGTAAGGAACCATTTCCCAAATCT 200
    ||||||||||||||||||||||||||||||||||||||||||||||||||
151 AAAGGAACATTGGTATGTGTCCTACCTGTAAGGAACCATTTCCCAAATCT 200

201 GACATGGAGACTCACATGGCTGCAGAACACTGTCAGGTGACCTGCAAATG 250
    ||||||||||||||||||||||||||||||||||||||||||||||||||
201 GACATGGAGACTCACATGGCTGCAGAACACTGTCAGGTGACCTGCAAATG 250

251 TAACAAGAAGTTGGAGAAGAGGCTGTTAAAGAAGCATGAGGAGACTGAGT 300
    ||||||||||||||||||||||||||||||||||||||||||||||||||
251 TAACAAGAAGTTGGAGAAGAGGCTGTTAAAGAAGCATGAGGAGACTGAGT 300

301 GCCCTTTGCGGCTTGCTGTCTGCCAGCACTGTGATTTAGAACTTTCCATT 350
    ||||||||||||||||||||||||||||||||||||||||||||||||||
301 GCCCTTTGCGGCTTGCTGTCTGCCAGCACTGTGATTTAGAACTTTCCATT 350

351 CTCAAACTGAAGGAACATGAAGATTATTGTGGTGCCCGGACGGAACTATG 400
    |||||||||||
351 CTCAAACTGAA.................................... 361

OBVIOUS SPLICE SITE

1701 CGGGTCACCCCTGCAGCTGCCAACTACCGCAGCAGAACTGCAAAGGCAAA 1750
     ||||||||||||||||||||||||||||||||||||||||||||||||
 362 ...GTCACCCCTGCAGCTGCCAACTACCGCAGCAGAACTGCAAAGGCAAA 409

1751 GCCTTCCAAGCAACAGGGAGCTGGGGATGCAGAAGAGGAAGAGGAGGAGT 1800
     ||||||||||||||||||||||||||||||||||||||||||||||||||
 410 GCCTTCCAAGCAACAGGGAGCTGGGGATGCAGAAGAGGAAGAGGAGGAGT 459

1801 AATGGTGTCTCCAGAGACTTTACATCGGTTCCTGTCTTCTGTGCACAGCA 1850
     ||||||||||||||||||||||||||||||||||||||||||||||||||
 460 AATGGTGTCTCCAGAGACTTTACATCGGTTCCTGTCTTCTGTGCACAGCA 509
```

Fig. 37B-1

```
1851 GCACTTGCCGCTGTGCAGGCCCACCTCTTTGGCTCTTTGGGTGGGAGAGT 1900
     ||||||||||||||||||||||||||||||||||||||||||||||||||
 510 GCACTTGCCGCTGTGCAGGCCCACCTCTTTGGCTCTTTGGGTGGGAGAGT 559

1901 TTTTCCAGATTTTAGATTTTTCTAGGTTATGGCCATTTTGTGTCTTTTGA 1950
     ||||||||||||||||||||||||||||||||||||||||||||||||||
 560 TTTTCCAGATTTTAGATTTTTCTAGGTTATGGCCATTTTGTGTCTTTTGA 609

1951 GGTTGTGCTGTGGGGGTTTGGGTTTGAGGGAAGGGAGCAGGGTGGCGGTT 2000
     ||||||||||||||||||||||||||||||||||||||||||||||||||
 610 GGTTGTGCTGTGGGGGTTTGGGTTTGAGGGAAGGGAGCAGGGTGGCGGTT 659

2001 GAGGAACGCTTCAGCCTTAGCTGCTACCTTTCGGCAGCAGTGAAATACAA 2050
     ||||||||||||||||||||||||||||||||||||||||||||||||||
 660 GAGGAACGCTTCAGCCTTAGCTGCTACCTTTCGGCAGCAGTGAAATACAA 709

2051 GCTGCAGCCTCGGCTGCCAGGGCTCCCTTTTGACTTATTGTCGCCACTGC 2100
     ||||||||||||||||||||||||||||||||||||||||||||||||||
 710 GCTGCAGCCTCGGCTGCCAGGGCTCCCTTTTGACTTATTGTCGCCACTGC 759

2101 CCCTTGGTGCTGTGTGGTCCCAGTGGAAGGAGGGGAAGATTTTGGAAACC 2150
     ||||||||||||||||||||||||||||||||||||||||||||||||||
 760 CCCTTGGTGCTGTGTGGTCCCAGTGGAAGGAGGGGAAGATTTTGGAAACC 809

2151 TGGTAGCCACCAGTAAGGTGATTCTCTGCCCTGTTGGGGCCTAAATTTGG 2200
     ||||||||||||||||||||||||||||||||||||||||||||||||||
 810 TGGTAGCCACCAGTAAGGTGATTCTCTGCCCTGTTGGGGCCTAAATTTGG 859

2201 GGGCTTTTGGGCAACCTCTCCGTGTACTGCGTCTGTCCACACTCGATTGG 2250
     ||||||||||||||||||||||||||||||||||||||||||||||||||
 860 GGGCTTTTGGGCAACCTCTCCGTGTACTGCGTCTGTCCACACTCGATTGG 909

2251 GCCCCAGGTGTGTATGAGGCGCTCTGGTAAGGTGCTCAGGCCAGTTGCAA 2300
     ||||||||||||||||||||||||||||||||||||||||||||||||||
 910 GCCCCAGGTGTGTATGAGGCGCTCTGGTAAGGTGCTCAGGCCAGTTGCAA 959

2301 TGTCTGTCAGTAACGAGGCTTTTGATGTGTTGAGCTGGAGGTGAGTGGAC 2350
     ||||||||||||||||||||||||||||||||||||||||||||||||||
 960 TGTCTGTCAGTAACGAGGCTTTTGATGTGTTGAGCTGGAGGTGAGTGGAC 1009

2351 CGGGGGCTGTGTTTTAAGCTGCTTCCTTGGCATTTGGCATCACTGCCTTC 2400
     ||||||||||||||||||||||||||||||||||||||||||||||||||
1010 CGGGGGCTGTGTTTTAAGCTGCTTCCTTGGCATTTGGCATCACTGCCTTC 1059
```

Fig. 37B-2

```
2401 TGTTCCCGGGGGAGCATGGATCTTTTGTCCTCACTGCTTTCTAATGGGGA 2450
     ||||||||||||||||||||||||||||||||||||||||||||||||||
1060 TGTTCCCGGGGGAGCATGGATCTTTTGTCCTCACTGCTTTCTAATGGGGA 1109

2451 GGGCTGAGGGCTCCCTGTCCCCACAGCAGGTATGGTTGCTCTGCCCCAGC 2500
     ||||||||||||||||||||||||||||||||||||||||||||||||||
1110 GGGCTGAGGGCTCCCTGTCCCCACAGCAGGTATGGTTGCTCTGCCCCAGC 1159

2501 CCCACACTTGCTCTGAAAACCAAGTGTCAGAGCCCCTTCCCCTTGTTTTT 2550
     ||||||||||||||||||||||||||||||||||||||||||||||||||
1160 CCCACACTTGCTCTGAAAACCAAGTGTCAGAGCCCCTTCCCCTTGTTTTT 1209

2551 ATTTTACTGTTATAATAATTATTAACTTCCTTGTAATAGAAATAAAGTTT 2600
     ||||||||||||||||||||||||||||||||||||||||||||||||||
1210 ATTTTACTGTTATAATAATTATTAACTTCCTTGTAATAGAAATAAAGTTT 1259

2601 GTACTTGGAAAAAAAAAAAAAAAAAAAAAAAAAAAAAAAAAAA 2643
     |||||||||||||||||||||||||||||||||||||||||||
1260 GTACTTGGAAAAAAAAAAAAAAAAAAAAAAAAAAAAAAAAAAA 1302
```

Fig. 37B-3

```
                        I                              II
  1  MEGDFSVCRN CKRHVVSANF TLHEAYCLRF LVLCPECEEP VPKETMEEHC
                        III                            IV
 51  KLEHQQVGCT MCQQSMQKSS LEFHKANECQ ERPVECKFCK LDMQLSKLEL
                        V
101  HESYCGSRTE LCQGCGQFIM HRMLAQHRDV CRSEQAQLGK GERISAPERE
                        VI
151  IYCHYCNQMI PENKYFHHMG KCCPDSEFKK HFPVGNPEIL PSSLPSQAAE

201  NQTSTMEKDV RPKTRSINRF PLHSESSSKK APRSKNKTLD PLLMSEPKPR
                                          VII
251  TSSPRGDKAA YDILRRCSQC GILLPLPILN QHQEKCRWLA SSKRKTSEKF

301  QLDLEKERYY KFKRFHF*
```

Fig. 38A

```
                                I                               II
  1  MAEFLDDQET  RLCDNCKKEI  PVFNFTIHEI  HCQRNIGMCP  TCKEPFPKSD
                                III                        IV
 51  METHMAAEHC  QVTCKCNKKL  EKRLLKKHEE  TECPLRLAVC  QHCDLELSIL
                                 V
101  KLKEHEDYCG  ARTELCGNCG  RNVLVKDLKT  HPEVCGREGE  EKRNEVAIPP
151  NAYDESWGQD  GIWIASQLLR  QIEALDPPMR  LPRRPLRAFE  SDVFHNRTTN
201  QRNITAQVSI  QNNLFEEQER  QERNRGQQPP  KEGGEESANL  DFMLALSLQN
                                                                VI
251  EGQASSVAEQ  DFWRAVCEAD  QSHGGPRSLS  DIKGAADEIM  LPCEFCEELY
301  PEELLIDHQT  SCNPSRALPS  LNTGSSSPRG  VEEPDVIFQN  FLQQAASNQL
                                         VII
351  DSLMGLSNSH  PVEESIIIPC  EFCGVQLEEE  VLFHHQDQCD  QRPATATNHV
401  TEGIPRLDSQ  PQETPPELPR  RRVRHQGDLS  SGYLDDTKQE  TANGPTSCLP
451  PSRPINNMTA  TYNQLSRSTS  GPRPGCQPSS  PCVPKLSNSD  SQDIQGRNRD
501  SQNGAIAPGH  VSVIRPPQNL  YPENIVPSFS  PGPSGRYGAS  GRSEGGRNSR
551  VTPAAANYRS  RTAKAKPSKQ  QGAGDAEEEE  EE*
```

Fig. 38B

```
                                I                               II
  1  MAEFLDDQET  RLCDNCKKEI  PVFNFTIHEI  HCQRNIGMCP  TCKEPFPKSD
                                III
 51  METHMAAEHC  QVTCKCNKKL  EKRLLKKHEE  TECPLRLAVC  QHCDLELSIL
101  KLKVTPAAAN  YRSRTAKAKP  SKQQGAGDAE  EEEE*
```

Fig. 38C

```
  1 MAEFLDDQETRLCDNCKKEIPVFNFTIHEIHCQRNIGMCPTCKEPFPKSD  50
    :.:  .:| |||:.:.   |||:||  .|  |  :.:||.|.||.||..
  1 .....MEGDFSVCRNCKRHVVSANFTLHEAYCLRFLVLCPECEEPVPKET  45

51 METHMAAEHCQVTC.KCNKKLEKRLLKKHEETECPLRLAVCQHCDLELSI  99
    ||.|   ||  ||.| .|...::|. |.  |...||. | .|. |.|:: :
 46 MEEHCKLEHQQVGCTMCQQSMQKSSLEFHKANECQERPVECKFCKLDMQL  95

100 LKLKEHEDYCGARTELCGNCGRNVLVKDLKTHPEVCGREGEEKRNEVAIP 149
    ||. ||.|||.|||||..||. :: : |  |.:||     |.|  |
 96 SKLELHESYCGSRTELCQGCGQFIMHRMLAQHRDVC.......RSEQAQL 138

150 PNAYDESWGQDGIWI..ASQLLRQIEALDPPMRLPRRPLRAFESDVFHNR 197
    ..:    |  .: :|:.  ..|:..: . :..                .:
139 GKGERISAPEREIYCHYCNQMIPENKYFHHM.................GK 171

198 TTNQRNITAQVSIQNNLFEEQERQERNRGQQPPKEGGEESANLDFMLALS 247
    ..  :.::. :..:.|   :  .  .... :.|...  :  : .:.  : :.
172 CCPDSEFKKHFPVGNPEILPSSLPSQAAENQTSTMEKDVRPKTRSINRFP 221

248 LQNEGQASSVAEQDFWRAVCEADQSHGGPRSLSDIKG.AADEIMLPCEFC 296
    |:.|:  .|.  |...   :.:  .    |.. ||. |.   :||:|:.|.|
222 LHSES.SSKKAPRSKNKTLDPLLMSEPKPRTSSPRGDKAAYDILRRCSQC 270

297 EELYPEELLIDHQTSCNPSRALPSLNTGSSSPRGVEEPDVIFQNFLQQAA 346
    :  |.|  .:|  :||..|.          :||...:.|.   ||    |:..
271 GILLPLPILNQHQEKCR........WLASSKRKTSEK....FQLDLEKER 308

347 SNQLDSLMGLSNSHPVEESIIIPCEFCGVQLEEEVLFHHQDQCDQRPATA 396
    .:...:
309 YYKFKRFHF*......................................  318
```

Fig. 39

XAF GENES AND POLYPEPTIDES: METHODS AND REAGENTS FOR MODULATING APOPTOSIS

CROSS-REFERENCE TO RELATED APPLICATIONS

This application is a continuation of U.S. patent application Ser. No. 09/616,614, filed Jul. 14, 2000, now issued as U.S. Pat. No. 6,495,339, which is a divisional of Ser. No. 09/100,391, filed Jun. 19, 1998, now issued as U.S. Pat. No. 6,107,088, which claims benefit from U.S. provisional applications 60/056,338, filed Aug. 18, 1997, 60/054,491, filed Aug. 1, 1997, and 60/052,402, filed Jul. 14, 1997.

BACKGROUND OF THE INVENTION

This invention relates to apoptosis, tumor necrosis factor-α (TNF-α) mediated signalling, cell cycle and tumor growth suppression.

Apoptosis is a morphologically distinct form of programmed cell death that is important in the normal development and maintenance of multicellular organisms. Dysregulation of apoptosis can take the form of inappropriate suppression of cell death, as occurs in the development of cancers, or in a failure to control the extent of cell death, as is believed to occur in acquired immunodeficiency and certain neurodegenerative disorders.

Some baculoviruses encode proteins termed "inhibitors of apoptosis proteins" (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which may be involved in DNA binding, and two N-terminal domains that consist of a 70 amino acid repeat motif termed a BIR domain (Baculovirus IAP Repeat).

We have recently discovered a mammalian family of IAP polypeptides. These polypeptides include the human proteins HIAP-1, HIAP-2, and XIAP and their murine homologs. A related protein, NAIP, has also been found. The mammalian IAP levels have been shown to be increased both in cancer cells and cells which survive events known to induce apoptosis (e.g., ischemia). The IAPs have also been shown to block apoptosis triggered by diverse stimuli. These results are consistent with a role for the mammalian IAPs as inhibitors of apoptosis.

The IAP family is now known to include at least two *Drosophila* proteins, in addition to the original four mammalian homologues (Hay et al., Cell 83: 1253–1262, 1995). Although we and others have established that the IAPs can suppress apoptosis in tissue culture model systems their mechanism of action is still under investigation.

SUMMARY OF THE INVENTION

We have discovered a novel family of genes, the XAFs. Members of the XAF gene family encode proteins that interact with IAPs and are associated with apoptosis. Our discovery allows the development of diagnostic, prognostic, and therapeutic compounds and methods for the detection and treatment of diseases involving apoptosis.

In a first aspect, the invention features substantially pure nucleic acid encoding a XAF polypeptide.

In a second aspect, the invention features substantially pure nucleic acid corresponding to at least ten nucleotides of a nucleic acid encoding a XAF polypeptide, where the nucleic acid is antisense nucleic acid and the antisense nucleic acid is sufficient to decrease XAF biological activity. In various embodiments of this aspect, the antisense nucleic acid corresponds to at least fifteen nucleotides of a nucleic acid encoding a XAF polypeptide, at least thirty nucleotides of a nucleic acid encoding a XAF polypeptide, or at least 100 nucleotides of a nucleic acid encoding a XAF polypeptide. In other embodiments, the XAF biological activity is decreased by at least 20%, 40%, 60%, or 80%. In yet another embodiment of this aspect of the invention, the antisense nucleic acid is in a vector where the vector is capable of directing expression of the antisense nucleic acid in a vector-containing cell.

In a third aspect, the invention features a vector that includes a substantially pure nucleic acid encoding a XAF polypeptide, where the vector is capable of directing expression of the polypeptide in a vector-containing cell.

In another related aspect, the invention features a cell that contains a substantially pure nucleic acid encoding a XAF polypeptide. In a preferred embodiment of this aspect, the nucleic acid is expressed in the cell. In various preferred embodiments, the cell is present in a patient having a disease that is caused by excessive or insufficient cell death and the cell is selected from the group that includes a fibroblast, a neuron, a glial cell, an insect cell, an embryonic stem cell, a myocardial cell, and a lymphocyte.

In a fifth aspect, the invention features a transgenic animal generated from a cell genetically engineered to lack nucleic acid encoding a XAF polypeptide, where the transgenic animal lacks expression of the XAF polypeptide.

In a related aspect, the invention features a transgenic animal generated from a cell that contains a substantially pure nucleic acid that replaces DNA encoding a XAF polypeptide, where the nucleic acid is expressed in the transgenic animal.

In various embodiments of this aspect, the XAF polypeptide is from a mammal (e.g., a human or a rodent). In another embodiment, the nucleic acid is genomic DNA or cDNA, and is operably linked to regulatory sequences for expression of the polypeptide where the regulatory sequences include a promoter (e.g., a constitutive promoter, a promoter inducible by one or more external agents, or a cell-type specific promoter). In other preferred embodiments, the XAF polypeptide is selected from a group that includes XAF-1, XAF-2 N terminus, XAF-2L and XAF-2S. In another embodiment, the XAF-1 has the amino acid sequence of SEQ ID NO.: 2 or the nucleic acid sequence of SEQ ID NO.: 1, and may include a deletion of the nucleic acids encoding the carboxy terminal amino acids 173 to 317 of XAF-1 (SEQ ID NO.: 8); or a deletion of the nucleic acids encoding the amino terminal amino acids 1 to 172 of XAF-1 (SEQ ID NO.: 7). In another embodiment of this aspect of the invention, the XAF-2 N terminus polypeptide has the amino acid sequence of SEQ ID NO.: 4 or the nucleic acid sequence of SEQ ID NO.: 3. In another embodiment, the XAF-2L polypeptide has the amino acid sequence of SEQ ID NO.: 10 or the nucleic acid sequence of SEQ ID NO.: 9. In yet another embodiment, the XAF-2S polypeptide has the amino acid sequence of SEQ ID NO.: 12 or the nucleic acid sequence of SEQ ID NO.: 11.

In a seventh aspect, the invention features a method of identifying a compound that modulates apoptosis. The method includes: (a) providing a cell that has a XAF gene; (b) contacting the cell with a candidate compound; and (c) monitoring expression of the XSF gene, where an alteration in the level of expression of the XAF gene indicates the presence of a compound which modulates apoptosis. In one preferred embodiment of this aspect, the alteration that is an increase indicates the compound is increasing apoptosis, and the alteration that is a decrease indicates the compound is decreasing apoptosis. In various embodiments of this aspect, the cell is transformed and the cell is not able to induce apoptosis by expression of p53.

In a related aspect, the invention features another method of identifying a compound that is able to modulate apoptosis that includes: (a) providing a cell including a reporter gene operably linked to a promoter from a XAF gene; (b) contacting the cell with a candidate compound; and (c) measuring expression of the reporter gene, where a change in the expression in response to the candidate compound identifies a compound that is able to modulate apoptosis. In one preferred embodiment of this aspect, the alteration that is an increase indicates the compound is increasing apoptosis, and the alteration that is a decrease indicates the compound is decreasing apoptosis. In various embodiments of this aspect, the cell is transformed and the cell is not able to induce apoptosis by expression of p53.

In a ninth aspect, the invention features a method of identifying a compound that is able to inhibit XAF-mediated apoptosis that includes: (a) providing a cell expressing an apoptosis-inducing amount of XAF; (b) contacting the cell with a candidate compound; and (c) measuring the level of apoptosis in the cell, where a decrease in the level relative to a level in a cell not contacted with the candidate compound indicates a compound that able to inhibit XAF-mediated apoptosis. In various embodiments of this aspect, the cell is transformed and the cell is not able to induce apoptosis by expression of p53.

In a tenth aspect, the invention features a method of identifying a compound that is able to induce XAF-mediated apoptosis that includes: (a) providing a cell expressing an apoptosis-inducing amount of XAF; (b) contacting the cell with a candidate compound; and (c) measuring level of apoptosis in the cell, where an increase in the level relative to a level in a cell not contacted with the candidate compound indicates a compound that able to induce XAF-mediated apoptosis. In various embodiments of this aspect, the cell is transformed and the cell is not able to induce apoptosis by expression of p53.

In related aspects, the invention features other methods of identifying a compound that is able to modulate apoptosis.

One such method includes: (a) providing a cell expressing a TRAF polypeptide, a XAF polypeptide, and a reporter gene operably linked to DNA that includes an NF-κB binding site; (b) contacting the cell with a candidate compound; and (c) measuring expression of the reporter gene, where a change in expression in response to the compound indicates that the compound is able to modulate apoptosis. In a preferred embodiment of this aspect of the invention, the TRAF is selected from a group that includes TRAF2, TRAF5, and TRAF6. In various embodiments of this aspect, the cell is transformed and the cell is not able to induce apoptosis by expression of p53.

A second such method includes: (a) providing a cell expressing a TRAF polypeptide, a XAF polypeptide, an IAP polypeptide, and a reporter gene operably linked to DNA that includes an NF-κB binding site; (b) contacting the cell with a candidate compound; and (c) measuring expression of the reporter gene, where a change in expression in response to the compound indicates that the compound is able to modulate apoptosis. In a preferred embodiment of this aspect of the invention, the IAP is XIAP. In another preferred embodiment of this aspect of the invention, the TRAF is selected from a group that includes TRAF2, TRAF5, and TRA-F6. In various embodiments of this aspect, the cell is transformed and the cell is not able to induce apoptosis by expression of p53.

A third such method includes: (a) providing a cell having: (i) a reporter gene operably linked to a DNA-binding-protein recognition site; (ii) a first fusion gene capable of expressing a first fusion protein, where the first fusion protein includes a XAF polypeptide covalently bonded to a binding moiety capable of specifically binding to the DNA-binding-protein recognition site; (iii) a second fusion gene capable of expressing a second fusion protein, where the second fusion protein includes a XAF polypeptide covalently bonded to a gene activating moiety; (b) exposing the cell to the compound; and (c) measuring reporter gene expression in the cell, where a change in the reporter gene expression indicates that the compound is capable of modulating apoptosis. In a preferred embodiment of this aspect of the invention, the cell is a yeast cell.

A fourth method for detecting a compound capable of modulating apoptosis includes: (a) providing a cell having: (i) a reporter gene operably linked to a DNA-binding-protein recognition site; (ii) a first fusion gene capable of expressing a first fusion protein, where the first fusion protein includes a XAF polypeptide covalently bonded to a binding moiety capable of specifically binding to the DNA-binding-protein recognition site; (iii) a second fusion gene capable of expressing a second fusion protein, where the second fusion protein includes an IAP polypeptide covalently bonded to a gene activating moiety; (b) exposing the cell to the compound; and (c) measuring reporter gene expression in the cell, where a change in the reporter gene expression indicates that the compound is capable of modulating apoptosis. In a preferred embodiment of this aspect of the invention, the IAP is XIAP. In another preferred embodiment, the cell is a yeast cell.

A fifth such method includes: (a) providing a cell having: (i) a reporter gene operably linked to a DNA-binding-protein recognition site; (ii) a first fusion gene capable of expressing a first fusion protein, where the first fusion protein includes an IAP polypeptide covalently bonded to a binding moiety capable of specifically binding to the DNA-binding-protein recognition site; (iii) a second fusion gene capable of expressing a second fusion protein, where the second fusion protein includes a XAF polypeptide covalently bonded to a gene activating moiety; (b) exposing the cell to the compound; and (c) measuring reporter gene expression in the cell, where a change in the reporter gene expression indicates that the compound is capable of modulating apoptosis. In a preferred embodiment of this aspect of the invention, the IAP is XIAP. In another preferred embodiment, the cell is a yeast cell.

A sixth such method includes: (a) providing a first XAF polypeptide immobilized on a solid-phase substrate; (b) contacting the first XAF polypeptide with a second XAF polypeptide; (c) contacting the first XAF polypeptide and the second XAF polypeptide with a compound; and (d) measuring amount of binding of the first XAF polypeptide to the second XAF polypeptide, where a change in the amount relative to an amount not contacted with the compound indicates that the compound is capable of modulating apoptosis.

A seventh method for detecting a compound capable of modulating apoptosis includes: (a) contacting a XAF polypeptide immobilized on a solid-phase substrate; (b)

providing the XAF polypeptide with an IAP polypeptide; (c) contacting the XAF polypeptide and the IAP polypeptide with a compound; and (d) measuring amount of binding of the XAF polypeptide to the IAP polypeptide, where a change in the amount relative to an amount not contacted with the compound indicates that the compound is capable of modulating apoptosis. In a preferred embodiment of this aspect of the invention, the IAP is XIAP.

An eighth such method includes: (a) providing an IAP polypeptide immobilized on a solid-phase substrate; (b) contacting the IAP polypeptide with a XAF polypeptide; (c) contacting the IAP polypeptide and the XAF polypeptide with a compound; and (d) measuring amount of binding of the IAP polypeptide to the XAF polypeptide, where a change in the amount relative to an amount not contacted with the compound indicates that the compound is capable of modulating apoptosis. In a preferred embodiment of this aspect of the invention, the IAP is XIAP.

In various preferred embodiments of the seventh to eighteenth method aspects of the invention, the XAF is XAF-1; the XAF is the N-terminus of XAF-2; the XAF is XAF-2L, or the XAF is XAF-2S. In other embodiments, the XAF is from a mammal (e.g., a human or a rodent).

In a nineteenth aspect, the invention features a method of increasing apoptosis in a cell by administering to the cell an apoptosis inducing amount of XAF polypeptide or fragment thereof.

In related aspects, the invention includes methods of increasing apoptosis by either providing a transgene encoding a XAF polypeptide or fragment thereof to a cell of an animal such that the transgene is positioned for expression in the cell; or by administering to the cell a compound which increases XAF biological activity in a cell (e.g., by administering a polypeptide fragment of a XAF polypeptide, a mutant of a XAF polypeptide, or a nucleic acid encoding a XAF polypeptide, a mutant thereof, or a polypeptide fragment thereof).

In preferred embodiment of the nineteenth, twentieth, and twenty-first aspects of the invention, the XAF is selected from a group that includes XAF-1, XAF-2 N-terminus, XAF-2L, and XAF-2S. In various preferred embodiments, the XAF is from a mammal (e.g., a human or rodent); the cell is in a mammal (e.g., a human or rodent); the cell is in an mammal diagnosed as having a condition involving insufficient apoptosis, (e.g., a cancer such as breast cancer, uterine cervical carcinoma, gastric carcinoma, ovarian epithelial cancer, pediatric medulloblastoma, lung carcinoma, prostate cancer); and the cell is a peripheral blood leukocyte (e.g., a lymphocyte), a muscle cell (e.g., a myocardial cell), an intestinal cell, an ovarian cell, a placental cell, or a thymus cell (e.g., a thymocyte).

In a twenty-second aspect, the invention features a method of inhibiting apoptosis in a cell, by administering to the cell an apoptosis-inhibiting amount of XAF polypeptide or fragment thereof.

In related aspects, the invention features a method of inhibiting apoptosis in a cell by providing to the cell a transgene encoding a XAF polypeptide or fragment positioned for expression in the cell; and a method of inhibiting apoptosis by administering a compound which decreases XAF biological activity (e.g., an antibody which specifically binds to a XAF polypeptide (e.g., a neutralizing antibody), a polypeptide fragment of a XAF polypeptide, a mutant form of a XAF polypeptide, an antisense nucleic acid complementary to the XAF coding sequence, a negative regulator of the XAF-dependent apoptotic pathway, or a XAF antisense nucleic acid).

In a preferred embodiment of the twenty-second, twenty-third, and twenty-fourth aspects of the invention, the XAF is selected from a group that includes XAF-1, XAF-2 N-terminus, XAF-2L, and XAF-2S. In various preferred embodiments, the XAF is from a mammal (e.g., a human or rodent); the cell is in a mammal (e.g., a human or rodent); and the mammal bearing the cell is an mammal diagnosed as having a condition involving excessive apoptosis (e.g., AIDS, a neurodegenerative disease, a myelodysplastic syndrome, or an ischemic injury (caused by, e.g., a myocardial infarction, a stroke, or a reperfusion injury, a toxin-induced liver disease, physical injury, renal failure, a secondary exsanguination or blood flow interruption resulting from any other primary diseases)). In other preferred embodiments, the cell is a muscle cell (e.g., a myocardial cell), a peripheral blood leukocyte (e.g., a lymphocyte, such as a T lymphocyte (preferably, a CD4$^+$T lymphocyte)), an intestinal cell, an ovarian cell, a placental cell, a thymus cell (e.g., a thymocyte), or a breast cell.

In the twenty-fifth and twenty-sixth aspects, the invention features methods of diagnosing a mammal for the presence of disease involving altered apoptosis or an increased likelihood of developing a disease involving altered apoptosis. The methods include isolating a sample of nucleic acid from the mammal and determining whether the nucleic acid includes a XAF mutation, where the presence of a mutation is an indication that the animal has an apoptosis disease or an increased likelihood of developing a disease involving apoptosis; or measuring XAF gene expression in a sample from an animal to be diagnosed, where an alteration in the expression or activity relative to a sample from an unaffected mammal is an indication that the mammal has a disease involving apoptosis or increased likelihood of developing such a disease. In preferred embodiments, XAF gene expression is measured by assaying the amount of XAF polypeptide or XAF biological activity in the sample (e.g., the XAF polypeptide is measured by immunological methods), or XAF gene expression is measured by assaying the amount of XAF RNA in the sample.

In one preferred embodiment of the twenty-fifth and twenty-sixth of the invention, the XAF is selected from a group that includes XAF-1, XAF-2 N-terminus, XAF-2L, and XAF-2S. In another preferred embodiment, the mammal is a human.

In a twenty-seventh aspect, the invention features a kit for diagnosing a mammal for the presence of a disease involving altered apoptosis or an increased likelihood of developing a disease involving altered apoptosis that includes a substantially pure antibody that specifically binds a XAF polypeptide.

Another such kit includes a material for measuring XAF RNA (e.g., a probe). In a preferred embodiment, the material is a nucleic acid probe.

A third such kit includes both a substantially pure antibody that specifically binds a XAF polypeptide, as well as a material for measuring XAF RNA. In a preferred embodiment, the kit also includes a means for detecting the binding of the antibody to the XAF polypeptide. In another preferred embodiment, the material is a nucleic acid probe.

In a thirtieth aspect, the invention features a method of obtaining a XAF polypeptide, including: (a) providing a cell with DNA encoding a XAF polypeptide, the DNA being positioned for expression in the cell; (b) culturing the cell under conditions for expressing the DNA; and (c) isolating the XAF polypeptide.

In preferred embodiments of this aspect of the invention, the XAF is XAF-1, XAF-2 N terminus, XAF-2L, or XAF- 2S. In another preferred embodiment, the DNA further includes a promoter inducible by one or more external agents.

In a thirty-first aspect, the invention features a method of isolating a XAF gene or portion thereof having sequence identity to human XAF-1. The method includes amplifying by polymerase chain reaction the XAF gene or portion thereof using oligonucleotide primers wherein the primers (a) are each greater than 13 nucleotides in length; (b) each have regions of complementarity to opposite DNA strands in a region of the nucleotide sequence of FIG. 1; and (c) optionally contain sequences capable of producing restriction endonuclease cut sites in the amplified product; and isolating the XAF gene or portion thereof.

In a related aspect, the invention features a method of isolating a XAF gene or portion thereof having sequence identity to human XAF-2L or XAF-2S. The method includes amplifying by polymerase chain reaction the XAF gene or portion thereof using oligonucleotide primers wherein the primers (a) are each greater than 13 nucleotides in length; (b) each have regions of complementarity to opposite DNA strands in a region of the nucleotide sequence of FIG. 37A; and (c) optionally contain sequences capable of producing restriction endonuclease cut sites in the amplified product; and isolating the XAF gene or portion thereof.

In another related aspect, the invention features a method of isolating a XAF gene or fragment thereof from a cell, including the steps of: (a) providing a sample of cellular DNA; (b) providing a pair of oligonucleotides having sequence homology to a conserved region of a XAF gene; (c) combining the pair of oligonucleotides with the cellular DNA sample under conditions suitable for polymerase chain reaction-mediated DNA amplification; and (d) isolating the amplified XAF gene or fragment thereof. In a preferred embodiment of the above three aspects, the polymerase chain reaction is reverse-transcription polymerase chain reaction (e.g., RACE).

In yet another related aspect, the invention features a method of identifying a XAF gene in a mammalian cell that includes: (a) providing a preparation of mammalian cellular DNA; (b) providing a detectably-labeled DNA sequence having identity to a conserved region of a second known XAF gene; and (c) contacting the preparation of cellular DNA with the detectably-labeled DNA sequence under hybridization conditions that provide detection of a gene having 50% or greater nucleotide sequence identity to the detectably-labeled DNA sequence; and identifying the XAF gene. In one preferred embodiment of this method for detecting a XAF gene, the DNA sequence includes at least a portion of XAF-1. In another preferred embodiment, the DNA sequence includes at least a portion of XAF-2L. In another preferred embodiment, the DNA sequence includes at least a portion of XAF-2S.

In a thirty-fifth aspect, the invention features a method for identifying a XAF gene that includes the steps of: (a) providing a mammalian cell sample; (b) introducing by transformation into the cell sample a candidate XAF gene; (c) expressing the candidate XAF gene within the cell sample; and (d) determining whether the sample exhibits an altered level of apoptosis, where an alteration in the level of apoptosis identifies a XAF gene. Preferably, the alteration is an increase in apoptosis and the cell is a leukocyte, a fibroblast, an insect cell, a glial cell, a myocardial cell, an embryonic stem cell, or a neuron.

In other aspects, the invention features a XAF nucleic acid for use in modulating apoptosis, a XAF polypeptide for use in modulating apoptosis, the use of a XAF polypeptide for the manufacture of a medicament for the modulation of apoptosis, and the use of a XAF nucleic acid for the manufacture of a medicament for the modulation of apoptosis. Preferably, the XAF is selected from a group that includes XAF-1, XAF-2 N terminus, XAF-2L, and XAF-2S.

In a fortieth aspect, the invention features a substantially pure antibody that specifically binds a XAF polypeptide, or a fragment or a mutant thereof. In one preferred embodiment of this aspect, the XAF polypeptide is selected from a group that includes XAF-1, XAF-2 N terminus XAF-2S, and XAF-2L. In other preferred embodiments, the XAF polypeptide is from a mammal (e.g., a human or a rodent), and the antibody is a polyclonal antibody, a monoclonal antibody, or a neutralizing antibody.

By "XAF", "XAF protein", or "XAF polypeptide" is meant a polypeptide, or fragment thereof, which has at least 30%, more preferably at least 35%, and most preferably 40% amino acid identity to either the amino-terminal 131 amino acids of the human XAF-1 (SEQ ID NO.: 2) or the amino-terminal 135 amino acids of human XAF-2L (SEQ ID NO.: 10) polypeptides. It is understood that polypeptide products from splice variants of XAF gene sequences are also included in this definition. Preferably, the XAF protein is encoded by nucleic acid having a sequence which hybridizes to a nucleic acid sequences present in either SEQ ID NO.: 1 or SEQ ID NO.: 9 under stringent conditions. Even more preferably the encoded polypeptide also has XAF biological activity. Preferably, the XAF polypeptide has at least three zinc finger domains. More preferably, the XAF polypeptide has at least six zinc finger domains, at least five of which occur within 150 amino acids of the N-terminus.

By "zinc finger" is meant a binding domain capable of associating with zinc. A preferable zinc binding domain has the amino acid sequence 5' C—$X_{2-5}$—C—$X_{11-18}$—C/H—$X_{2-5}$—C/H 3' (SEQ ID NO.: 6), wherein "X" may be any amino acid. A more preferable zinc binding domain has the amino acid sequence 5' C—$X_{1-2}$—C—$X_{11}$—H—$X_{3-5}$—C 3' (SEQ ID NO.: 7), wherein "X" may be any amino acid. Even more preferably, a zinc binding domain has the amino acid sequence 5' C—$X_2$—H—$X_{11}$—H—$X_3$—C 3' (SEQ ID NO.: 8), wherein "X" may be any amino acid. Most preferably, a zinc binding domain is one found in a XAF polypeptide.

By "XAF biological activity" is meant any one or more of the biological activities described herein for XAF-1, XAF-2L, or XAF-2S, including, without limitation, the ability to bind an IAP (e.g., a XIAP), or another XAF polypeptide; the ability to cause apoptosis when transfected into a cell (particularly in a HeLa cell); the ability to enhance the NF-κB inducing activity of a TRAF; and the ability to specifically bind a XAF-1, XAF-2L, or XAF-2S specific antibody.

By "modulating apoptosis" or "altering apoptosis" is meant increasing or decreasing the number of cells that undergo apoptosis (than would otherwise be the case) in a given cell population. Preferably, the cell population is selected from a group including T cells, neuronal cells, fibroblasts, myocardial cells, or any other cell line known to undergo apoptosis in a laboratory setting (e.g., the baculovirus infected insect cells or an in vivo assay). It will be appreciated that the degree of modulation provided by a XAF polypeptide or a modulating compound in a given assay will vary, but that one skilled in the art can determine the statistically significant change or a therapeutically effective change in the level of apoptosis which identifies a XAF polypeptide or a compound which modulates XAF or is a XAF therapeutic.

By "high stringency conditions" is meant hybridization in 2×SSC at 40° C. with a DNA probe length of at least 40 nucleotides. For other definitions of high stringency conditions, see Ausubel, F. et al., 1994, *Current Protocols in Molecular Biology*, John Wiley & Sons, New York, 6.3.1–6.3.6, hereby incorporated by reference.

By "IAP" is meant an amino acid sequence which has identity to baculovirus inhibitors of apoptosis. Mammalian IAPs include, without limitation, NAIP, HIAP1, HIAP2, and XIAP. Preferably, such a polypeptide has an amino acid sequence which is at least 45%, preferably 60%, and most preferably 85% or even 95% identical to at least one of the amino acid sequences of a baculovirus IAP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of more than two amino acids, regardless of post-translational modification such as glycosylation or phosphorylation.

By "pharmaceutically acceptable carrier" means a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a XAF polypeptide that is at least 75%, more preferably at least 90%, and most preferably at least 99%, by weight, pure. A substantially pure XAF polypeptide may be obtained, for example, by extraction from a natural source (e.g., a fibroblast, neuronal cell, or lymphocyte) by expression of a recombinant nucleic acid encoding a XAF polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides not only includes those derived from eukaryotic organisms but also those synthesized in *E. coli* or other prokaryotes. By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "TRAF" is meant a member of the TRAF family of proteins. TRAF family members each possess an amino terminal RING zinc finger and/or additional zinc fingers, a leucine zipper, and a unique, conserved carboxy terminal coiled coil motif, the TRAF-C domain, which defines the family. TRAF1 and TRAF2 were first identified as components of the TNF-R2 signaling complex (Rothe et al., Cell 78: 681–692, 1994). Preferred TRAF polypeptides are TRAF2, TRAF5, and TRAF6.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammals (e.g., rodents such as rats or mice) and the DNA (transgene) is inserted by artifice into the nuclear genome.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift mutation, or a missense mutation. Preferably, the mutation is an insertion or deletion, or is a frameshift mutation that creates a stop codon.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, heliumdriven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "transformed cell" is meant a cell into which (or into an ancestor of which) has been introduced, by means of recombinant DNA techniques, a DNA molecule encoding (as used herein) a XAF polypeptide.

By "positioned for expression" is meant that the DNA molecule is positioned adjacent to a DNA sequence which directs transcription and translation of the sequence (i.e., facilitates the production of, e.g., a XAF-1 polypeptide, a recombinant protein or a RNA molecule).

By "reporter gene" is meant any gene which encodes a product whose expression is detectable. A reporter gene product may have, one of the following attributes, without restriction: fluorescence (e.g., green fluorescent protein), enzymatic activity (e.g., luciferase or chloramphenicol acetyl transferase), toxicity (e.g., ricin), or an ability to be specifically bound by a second molecule (e.g., biotin or a detectably labeled antibody).

By "promoter" is meant a minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' or intron sequence regions of the native gene.

By "operably linked" is meant that a gene and one or more regulatory sequences are connected in such a way as to permit gene expression when the appropriate molecules (e.g., transcriptional activator proteins) are bound to the regulatory sequences.

By "conserved region" is meant any stretch of six or more contiguous amino acids exhibiting at least 30%, preferably 50%, and most preferably 70% amino acid sequence identity between two or more of the XAF family members, (e.g., between human XAF-1 and another human XAF).

By "detectably-labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, e.g., fluorescein labeling).

By "antisense," as used herein in reference to nucleic acids, is meant a nucleic acid sequence that is complementary to the coding strand of a gene, preferably, a XAF gene.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., a XAF-1, XAF-2 N-terminus, XAF-2L, or XAF-2S specific antibody. A purified antibody may be obtained, for example, by affinity chromatography using recombinantly-produced protein or conserved motif peptides and standard techniques.

By "specifically binds" is meant an antibody that recognizes and binds a XAF polypeptide but that does not substantially recognize and bind other non-XAF molecules in a sample, e.g., a biological sample, that naturally includes protein. A preferred antibody binds to the XAF-1 peptide sequence of FIG. 1 (SEQ ID NO.: 2). Another preferred antibody binds to the XAF-2 N-terminus peptide sequence of FIG. 35 (SEQ ID NO.: 4). Yet another preferred antibody binds to the XAF-2L peptide sequence of FIG. 37 (SEQ ID NO.: 10). Still another preferred antibody binds to the XAF-2S peptide sequence of FIG. 38C (SEQ ID NO.: 12). A more preferred antibody binds to two or more of XAF-1 (SEQ ID NO.: 2), XAF-2 N-terminus (SEQ ID NO.: 4), XAF-2L (SEQ ID NO.: 10) and XAF-2S (SEQ ID NO.: 12).

By "neutralizing antibodies" is meant antibodies that interfere with any of the biological activities of a XAF polypeptide, particularly the ability of a XAF to participate in apoptosis. The neutralizing antibody may reduce the ability of a XAF polypeptide to participate in apoptosis by, preferably 50%, more preferably by 70%, and most preferably by 90% or more. Any standard assay of apoptosis, including those described herein, may be used to assess potentially neutralizing antibodies.

Other features and advantages of the invention will be apparent from the following description of the preferred embodiments thereof, and from the claims.

BRIEF DESCRIPTION OF THE DRAWINGS

FIG. 1 is a listing of the cDNA (above; SEQ ID NO.: 1) and predicted amino acid (below; SEQ ID NO.: 2) sequences of human XAF-1.

FIGS. 4A–4B is a Northern dot-blot analysis of XAF-1 mRNA in multiple adult and fetal human tissues.

FIG. 15A shows metaphase spread hybridized with XAF-1 genomic probe. FIG. 15B shows metaphase spread after G banding with Giemsa stain. Specific fluorescent signals on 17p13.3 are indicated by arrows.

FIG. 34 is a table listing the interaction results of a yeast two-hybrid assay.

FIG. 35 is a listing of the cDNA (above; SEQ ID NO.: 3) and the predicted amino acid (below; SEQ ID NO.: 4) sequences of the N-terminus of human XAF-2. The seven zinc finger motifs are boxed and labeled in Roman numerals.

FIG. 36 is a listing of the 3' untranslated region (UTR) DNA sequence (SEQ ID NO.: 5) of human XAF-2 which is located about 250 base pairs C-terminally of SEQ ID NO.:3.

FIGS. 37A-1–37A-2 is a listing of the full length 5' nucleotide (above; SEQ ID NO.: 9) and amino acid (below; SEQ ID NO.: 10) sequences of the long (XAF-2L) splice variant of XAF-2. The shorter splice variant of XAF-2 (XAF-2S) is spliced as indicated.

FIGS. 37-1–37B-3 is an alignment comparing the nucleic acid sequence of XAF-2L (above) with the entire nucleic acid sequence of XAF-2S (below; SEQ ID NO.: 11).

FIGS. 38A, 38B, and 38C are the amino acid sequence listings of XAF-1, XAF-2L, and XAF-2S (SEQ ID NO.: 12), respectively, with the zinc finger binding domains indicated.

FIG. 39 is an alignment comparing the sequence of the first 396 amino acids of XAF-2L (above) with the entire amino acid sequence of XAF-1 (below).

DETAILED DESCRIPTION OF THE PREFERRED EMBODIMENT

Figure 2:
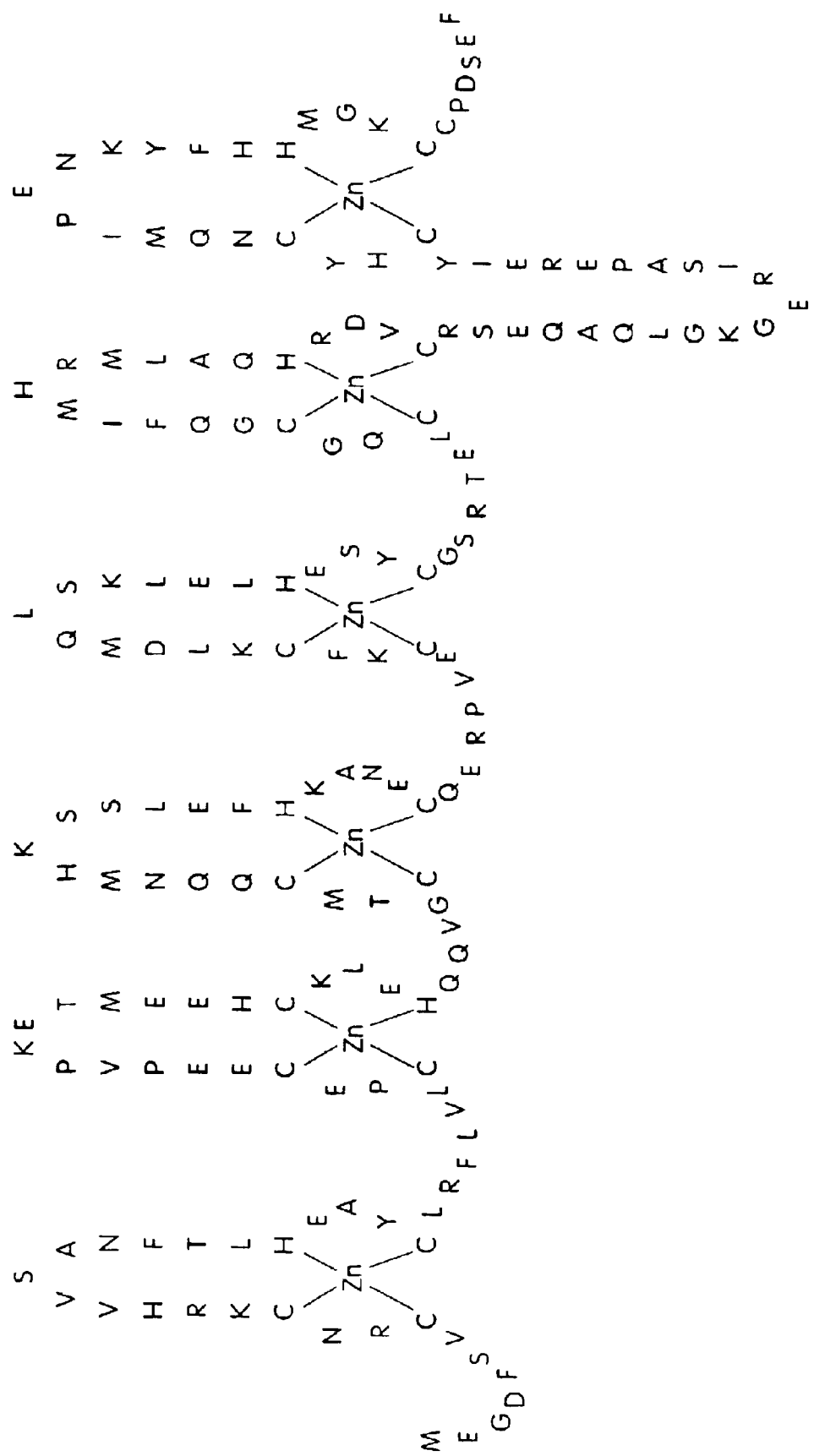
FIG. 2 is a schematic diagram of the six predicted Zn finger binding domains corresponding to the N-terminal 178 amino acids of XAF-1 (SEQ ID NO.: 6).

We have discovered a new family of proteins, the XAFs, which interact with IAPs and are involved the TNFα signal transduction pathway which regulates apoptosis.

The TNF receptor superfamily includes at least 13 transmembrane type I glycoproteins composed of two identical subunits with variable numbers of a characteristic cysteine rich extracellular repeat. Included among these members are TNF receptor 1 (TNF-R1), TNF receptor 2 (TNF-R2), CD40, Fas, and CD30. The corresponding ligands for these receptors are typically type II transmembrane glycoproteins expressed on the surface of interacting cells. In some instances, notably lymphotoxin-α (also known as TNFβ) and the majority of tumor necrosis factor-α (TNFα), the ligand is secreted from the cell.

The signals generated by ligated members of the TNF receptor superfamily can be stimulatory or inhibitory depending on the nature and activation state of the target cell. However, there is considerable overlap in the signal transduction pathways; for instance, ligation of TNF-R1, TNF-R2, CD30, and CD40 (Kitson et al., Nature 384: 372–275, 1996) all result in NF-κB activation, a transcription factor found latent in the cytoplasm of cells complexed to an inhibitor protein termed I-κB. Receptor ligation induces the phosphorylation of I-κB, which renders I-κB susceptible to ubiquitination and subsequent degradation. I-κB degradation unveils the nuclear translocation signal in NF-κB and allows nuclear localization and activation of transcription from NF-κB dependent promoters (reviewed in Grilli et al., Int. Rev. Cytol. 143: 1–60, 1993).

Tumor necrosis factor-α (TNFα), mediates its diverse effects through both the 55–60 kDa TNF-R1 and 75–80 kDa TNF-R2 receptors. The cytoplasmic domains of TNF-R1 and TNF-R2 are not conserved, which is reflected in both the protein factors associated with the cytoplasmic domains and in the consequences of receptor stimulation. TNF-α signaling through TNF-R2 can induce either proliferative responses (i.e., thymocyte and mononuclear proliferation; Tartaglia et al., Proc. Natl. Acad. Sci. USA 88: 9292–9296, 1991; Tartaglia, et al., J. Immunol. 151: 4637–4641, 1993; Gehr et al., J. Immunol. 149: 911–917, 1992), or cytolytic responses (Heller et al., Cell 70: 47–52, 1992; Grell et al., Lymphokine Cytokine Res. 12: 143–148, 1993) depending upon the cell type and activation state.

Immunoprecipitation of TNF-R2 complexes and peptide sequence analysis of the associated proteins identified HIAP-1 and HIAP-2 as components of the unstimulated TNF-R2 signaling complex. Protein-protein interaction analysis has established that the BIR domains of HIAP-1 and HIAP-2 can bind interchangeably to the TRAF-N domains of TRAF1 and TRAF2 (Rothe et al., Cell 83: 1243–1252, 1995). To date, very little is known regarding the distribution and function of the protein components of the TNF-R2 complex following receptor ligation. Likewise, the functional consequences of HIAP-1 and HIAP-2 in the TNF-R2 receptor complex have not been determined.

The role of HIAP-2 in the TNF-R1 receptor signaling complex has, in contrast, been more clearly defined.

The intracellular domain of TNF-R1 contains an approximately 80 amino acid protein-protein interaction motif termed a "death domain", which is also found in the low affinity nerve growth factor and Fas receptors. The cytoplasmic death domain of TNF-R1 does not appear to associate with components of the signal transduction pathways prior to ligand binding. The primary effects of TNF-R1 aggregation are NF-κB activation and apoptosis. These effects are dependent upon interaction of TNF-R1 with TRADD (TNF-R1 associated death domain protein; Hsu et al., Cell 81: 495–504, 1995), through their respective death domains. TRADD functions as an adapter molecule which can recruit a variety of proteins to the signaling complex. The formation of alternative signaling complexes likely determines the ultimate fate of the cell.

In certain circumstances, TRADD is capable of triggering the formation of a protein complex called the DISC (Death Inducing Signaling Complex). DISC formation occurs when FADD is recruited to the TNF-R1/TRADD complex, again through interaction of death domains (Chinnaiyan et al., Cell 81: 505–512 1995; Chinnaiyan et al., J. Biol. Chem. 271: 4961–4965, 1996). In addition to a carboxy terminal death domain, FADD possesses an amino terminal "death effector domain" (DED), which triggers apoptosis by recruiting FLICE (caspase-8). FLICE possesses an unusually long amino terminal pro-domain containing two DED homologous sequences which bind to the FADD DED. Bringing FLICE molecules into close proximity results in proteolytic auto-activation. The cleavage event that activates FLICE also releases the enzyme from the DISC, at which point it proteolytically activates other caspases and ultimately results in apoptosis (Muzio et al., Cell 85: 817–827, 1996, Boldin et al., 85: 803–815 1996). Dominant-negative mutants of FADD block apoptosis through either Fas or TNF-R1, indicating that the FADD component is responsible for propagating the cell death signal generated through either receptor (Chinnaiyan et al., J. Biol. Chem. 271: 4961–4965, 1996).

However, TNFα binding to TNF-R1 does not result in apoptosis in all circumstances. The formation of an alternative signaling complex contributes to the pliability of the TNFα response. The "survival complex" that corresponds to the DISC consists of TRADD bound to TRAF2 (TNF receptor associated factor-2) and HIAP-2 (Hsu et al., Immunity 4: 387–389, 1996; Hsu et al., Cell 84: 299–308, 1996). HIAP-2 is complexed to TRAF2 prior to TNF-R1 stimulation (Hsu et al., Cell 84: 299–308, 1996). This protein interaction may enhance the affinity of TRAF2 for binding to TRADD, thereby favoring the formation of TRADD/TRAF2 complexes rather than the TRADD/FADD/FLICE DISC. Alternatively, HIAP-2 may interact with other components of the apoptotic pathway, such as the caspases, in ways which suppress the apoptotic signals that would otherwise be generated.

We have now demonstrated that XAF family members interact with IAPs and are clearly involved in apoptotic and NF-κB inducing signaling pathways in mammalian cells. Overexpression of XAF-1 causes cell death in transformed cells. Interestingly, overexpression in non-transformed cells merely leads to growth (cell cycle) arrest. The distinct functions transformed and merely proliferating cells is surprising and significant. Our Western and Northern blot analyses indicate that XAF-1 is expressed in a variety of tissues and cell types. Since apoptosis is an event non-specific to any particular cell or tissue type, these findings are in keeping with the involvement of the XAF-1 protein in apoptosis in a variety of contexts.

We have also discovered a second XAF family member, XAF-2L. XAF-2L, like XAF-1, also has seven zinc finger binding domains. A second shorter XAF-2 splice variant, XAF-2S, has also been discovered.

I. The XAF-1 Gene

A yeast 2-hybrid screen of a human placenta cDNA library with XIAP as the 'bait' protein identified a 37 kDa zinc finger protein termed XAF-1 (XIAP Associated Factor 1). XAF-1 displays significant homology to members of the TRAF family, particularly TRAF6, but lacks the TRAF-C and TRAF-N domains.

II. Synthesis of XAF Proteins

The characteristics of the cloned XAF gene sequences may be analyzed by introducing the sequence into various cell types or using in vitro extracellular systems. The function of XAF proteins may then be examined under different physiological conditions. For example, the XAF-1-encoding DNA sequence may be manipulated in studies to understand the expression of the XAF-1 gene and gene product. Alternatively, cell lines may be produced which over-express the XAF gene product allowing purification of XAF for biochemical characterization, large-scale production, antibody production, and patient therapy.

For protein expression, eukaryotic and prokaryotic expression systems may be generated in which XAF gene sequences are introduced into a plasmid or other vector which is then used to transform living cells. Constructs in which the XAF cDNAs containing the entire open reading frames inserted in the correct orientation into an expression plasmid may be used for protein expression. Alternatively, portions of the XAF gene sequences, including wild-type or mutant XAF sequences, may be inserted. Prokaryotic and eukaryotic expression systems allow various important functional domains of the XAF proteins to be recovered as fusion proteins and then used for binding, structural and functional studies and also for the generation of appropriate antibodies. Since XAF-1 protein expression increases apoptosis in immortalized cells, it may be desirable to express the protein under the control of an inducible promoter.

Typical expression vectors contain promoters that direct the synthesis of large amounts of mRNA corresponding to the inserted XAF nucleic acid in the plasmid bearing cells. They may also include eukaryotic or prokaryotic origin of replication sequences allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced which have integrated the vector into the genomic DNA, and in this manner the gene product is produced on a continuous basis.

Expression of foreign sequences in bacteria such as *Escherichia coli* requires the insertion of the XAF nucleic acid sequence into a bacterial expression vector. This plasmid vector contains several elements required for the propagation of the plasmid in bacteria, and expression of inserted DNA of the plasmid by the plasmid-carrying bacteria. Propagation of only plasmid-bearing bacteria is achieved by introducing in the plasmid selectable marker-encoding sequences that allow plasmid-bearing bacteria to grow in the presence of otherwise toxic drugs. The plasmid also bears a transcriptional promoter capable of producing large amounts of mRNA from the cloned gene. Such promoters may or may not be inducible promoters which initiate transcription upon induction. The plasmid also preferably contains a polylinker to simplify insertion of the gene in the correct orientation within the vector. In a simple E. coli expression vector utilizing the lac promoter, the expression vector plasmid contains a fragment of the E. coli chromosome containing the lac promoter and the neighboring lacZ gene. In the presence of the lactose analog IPTG, RNA polymerase normally transcribes the lacZ gene producing lacZ mRNA which is translated into the encoded protein, β-galactosidase. The lacZ gene can be cut out of the expression vector with restriction endonucleases and replaced by a XAF gene sequence, or fragment, fusion, or mutant thereof. When this resulting plasmid is transfected into E. coli, addition of IPTG and subsequent transcription from the lac promoter produces XAF mRNA, which is translated into a XAF polypeptide.

Once the appropriate expression vectors containing a XAF gene, or fragment, fusion, or mutant thereof, are constructed they are introduced into an appropriate host cell by transformation techniques including calcium phosphate transfection, DEAE-dextran transfection, electroporation, micro-injection, protoplast fusion and liposo-memediated transfection. The host cell which are transfected with the vectors of this invention may be selected from the group consisting of E. coli, pseudomonas, Bacillus subtilus, or other bacilli, other bacteria, yeast, fungi, insect (using, for example, baculoviral vectors for expression), mouse or other animal or human tissue cells. Mammalian cells can also be used to express the XAF-1 protein using a vaccinia virus expression system described in Ausubel et al. (*Current Protocols in Molecular Biology*, John Wiley & Sons, New York, N.Y., 1994).

In vitro expression of XAF proteins, fusions, polypeptide fragments, or mutants encoded by cloned DNA is also possible using the T7 late-promoter expression system. This system depends on the regulated expression of T7 RNA polymerase which is an enzyme encoded in the DNA of bacteriophage T7. The T7 RNA polymerase transcribes DNA beginning within a specific 23-bp promoter sequence called the T7 late promoter. Copies of the T7 late promoter are located at several sites on the T7 genome, but none is present in E. coli chromosomal DNA. As a result, in T7 infected cells, T7 RNA polymerase catalyzes transcription of viral genes but not of E. coli genes. In this expression system recombinant E. coli cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed E. coli cells, large amounts of T7 RNA polymerase are produced. The polymerase then binds to the T7 late promoter on the plasmid expression vectors, catalyzing transcription of the inserted cDNA at a high rate. Since each E. coli cell contains many copies of the expression vector, large amounts of mRNA corresponding to the cloned cDNA can be produced in this system and the resulting protein can be radioactively labeled. Plasmid vectors containing late promoters and the corresponding RNA polymerases from related bacteriophages such as T3, T5, and SP6 may also be used for in vitro production of proteins from cloned DNA. E. coli can also be used for expression by infection with M13 Phage mGPI-2. E. coli vectors can also be used with phage lambda regulatory sequences, by fusion protein vectors, by maltose-binding protein fusions, and by glutathione-S-transferase fusion proteins.

Eukaryotic expression systems permit appropriate post-translational modifications to expressed proteins. Transient transfection of a eukaryotic expression plasmid allows the transient production of a XAF polypeptide by a transfected host cell. XAF proteins may also be produced by a stably-transfected mammalian cell line. A number of vectors suitable for stable transfection of mammalian cells are available to the public (e.g., see Pouwels et al., *Cloning Vectors: A Laboratory Manual*, 1985, Supp. 1987), as are methods for constructing such cell lines (see e.g., Ausubel et al., supra). In one example, cDNA encoding a XAF-1 protein, fusion, mutant, or polypeptide fragment is cloned into an expression vector that includes the dihydrofolate reductase (DHFR) gene. Integration of the plasmid and, therefore, integration of the XAF-1-encoding gene into the host cell chromosome is selected for by inclusion of 0.01–300 $\mu$M methotrexate in the cell culture medium (as described, Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra). These methods generally involve extended culture in medium containing gradually increasing levels of methotrexate. The most commonly used DHFR-containing expression vectors are pCVSEII-DHFR and pAdD26SV(A) (described in Ausubel et al., supra). The host cells described above or, preferably, a DHFR-deficient CHO cell line (e.g., CHO DHFR cells, ATCC Accession No. CRL 9096) are among those most preferred for DHFR selection of a stably-transfected cell line or DHFR-mediated gene amplification.

Eukaryotic cell expression of XAF proteins allows for studies of the XAF genes and gene products including determination of proper expression and post-translational modifications for biological activity, identifying regulatory elements located in the 5' region of XAF genes and their roles in tissue regulation of XAF protein expression. It also permits the production of large amounts of normal and mutant proteins for isolation and purification, and the use of cells expressing XAF proteins as a functional assay system for antibodies generated against the protein. Eukaryotic cells expressing XAF proteins may also be used to test the effectiveness of pharmacological agents on XAF associated apoptosis, or as means by which to study XAF proteins as components of a signal transduction system. Expression of XAF proteins, fusions, mutants, and polypeptide fragments in eukaryotic cells also enables the study of the function of the normal complete protein, specific portions of the protein, or of naturally occurring polymorphisms and artificially produced mutated proteins. The XAF DNA sequences can be altered using procedures known in the art, such as restriction endonuclease digestion, DNA polymerase fill-in, exonuclease deletion, terminal deoxynucleotide transferase extension, ligation of synthetic or cloned DNA sequences and site-directed sequence alteration using specific oligonucleotides together with PCR.

Another preferred eukaryotic expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (Mol. Cell Biol. 5:3610–3616, 1985).

Once the recombinant protein is expressed, it can be isolated from the expressing cells by cell lysis followed by protein purification techniques, such as affinity chromatography. In this example, an anti-XAF antibody, which may be produced by the methods described herein, can be attached to a column and used to isolate the recombinant XAF proteins. Lysis and fractionation of XAF protein-harboring cells prior to affinity chromatography may be performed by standard methods (see e.g., Ausubel et al., supra). Once isolated, the recombinant protein can, if desired, be purified further by e.g., by high performance liquid chromatography (HPLC; e.g., see Fisher, *Laboratory Techniques In Biochemistry And Molecular Biology,* Work and Burdon, Eds., Elsevier, 1980).

Polypeptides of the invention, particularly short XAF-1 fragments and longer fragments of the N-terminus and C-terminus of the XAF-1 protein, can also be produced by chemical synthesis (e.g., by the methods described in *Solid Phase Peptide Synthesis,* 2nd ed., 1984, The Pierce Chemical Co., Rockford, Ill.). These general techniques of polypeptide expression and purification can also be used to produce and isolate useful XAF-1 polypeptide fragments or analogs, as described herein.

Those skilled in the art of molecular biology will understand that a wide variety of expression systems may be used to produce the recombinant XAF proteins. The precise host cell used is not critical to the invention. The XAF proteins may be produced in a prokaryotic host (e.g., *E. coli*) or in a eukaryotic host (e.g., *S. cerevisiae,* insect cells such as Sf9 cells, or mammalian cells such as COS-1, NIH 3T3, or HeLa cells). These cells are commercially available from, for example, the American Type Culture Collection, Rockville, Md. (see also Ausubel et al., supra). The method of transformation and the choice of expression vehicle (e.g., expression vector) will depend on the host system selected. Transformation and transfection methods are described, e.g., in Ausubel et al. (supra), and expression vehicles may be chosen from those provided, e.g., in Pouwels et al., supra.

III. Testing for the Presence of XAF Biological Activity

Identification of XAF-1 and XAF-2 splice variants allow the study of XAF biological activity in apoptosis-associated cellular events. For example, administration of a XAF-1 protein, or polypeptide fragment thereof, may have an ability to induce apoptosis, as measured by apoptosis assays known in the art and described herein. An apoptosis-inhibiting amount of a XAF reagent (e.g., a compound that reduced the biological function of XAF-1, such as a XAF-1 neutralizing antibody or antisense XAF-1 nucleic acid) may be similarly assessed. Such assays may be carried out in a cell which either expresses endogenous XAF-1, or a cell to which is introduced a heterologous amount of a XAF-1 polypeptide. Preferably, the cell is capable of undergoing apoptosis. Apoptosis or inhibition thereof may be assessed in these XAF expressing cells, whereby such apoptosis inducing or inhibiting activity is evaluated based upon the level of expression of the XAF polypeptide.

Another approach, which utilizes the activation of the nuclear transcription factor, NF-κB (Kunkel et al., Crit. Rev. Immunol. 9: 93–117, 1989) in TNF-mediated signal transduction. In this system the role of a XAF in NF-κB activation may be readily elucidated in various assays known in the art, such as the I-κB degradation assay. Another method of rapidly measuring NF-κB activity is through the use of a reporter gene whose expression is directed by a NF-κB binding site containing promoter (Zeichner et al., J. Virol. 65: 2436–2444, 1991). The expression vector is preferably inserted by artifice into a cell capable of undergoing apoptosis or is responsive to TNF-receptor family-mediated signal transduction. By detecting a change in the level of expression of the reporter gene, an NF-κB-inducing ability of a XAF may be readily assessed. This method may also be used to detect an NF-κB-inhibiting ability of a XAF wherein NF-κB activation is stimulated by another component of the TNF-receptor signalling pathway (e.g., TRAF6).

It will be understood that these analyses may be undertaken with XAF-1 or other XAF proteins (e.g., XAF-2L).

IV. Cellular Distribution of XAF-1

We have looked at the distribution of XAF-1 mRNA expression using radiolabeled antisense XAF-1 DNA and have found that XAF-1 mRNA is expressed in at least the following adult tissues: heart, brain, placenta, liver, skeletal muscle, kidney, pancreas, spleen, thymus, prostate, testis, ovary, appendix, trachea, small intestine, submucosal lining of the colon, and peripheral blood leukocytes. XAF-1 mRNA was further found to be expressed in fetal tissue, including fetal brain, fetal heart, fetal kidney, fetal liver, fetal spleen, fetal thymus, and fetal lung.

V. XAF Fragments

Polypeptide fragments which incorporate various portions of XAF proteins are useful in identifying the domains important for the biological activities of XAF proteins. Methods for generating such fragments are well known in the art (see, for example, Ausubel et al., supra) using the nucleotide sequences provided herein. For example, a XAF protein fragment may be generated by PCR amplifying the desired fragment using oligonucleotide primers designed based upon the XAF-1 (SEQ ID NO.: 1) nucleic acid sequences. Preferably the oligonucleotide primers include unique restriction enzyme site which facilitate insertion of the fragment into the cloning site of a mammalian expression vector. This vector may then be introduced into a mammalian cell by artifice by the various techniques known in the art and described herein, resulting in the production of a XAF gene fragment.

In one approach, XAF-1 polypeptide fragments have been useful in evaluating the portions of the protein involved in NF-κB regulation. In particular, polypeptide fragments of the amino- and carboxyl-termini of XAF-1 protein were used to induce or prevent activity induction by various other components of the TNF-receptor signalling pathway (e.g., TRAF6).

In an alternative approach, polypeptide fragments of various portions of the XAF-1 protein are useful in modulating XAF-1 mediated apoptosis, as may be assessed in the various apoptosis assays known in the art and described herein. XAF1 polypeptide fragments may be used to alter XAF-1 mediated apoptosis by inhibiting binding of the full length XAF-1 to, for example, itself to form XAF-1:XAF-1 homodimers, to another XAF protein (e.g., XAF-2) to form XAF-1:XAF-2 heterodimers, or to XIAP to form XAF-1:XIAP heterodimers. Preferably, such fragments may include the XAF-1:XAF-1 binding domain, the XAF-1:XAF-2 binding domain or the XAF-1:XIAP binding domain.

VI. XAF Antibodies

In order to prepare polyclonal antibodies, YAF proteins, fragments of XAF proteins, or fusion proteins containing defined portions of XAF proteins can be synthesized in bacteria by expression of corresponding DNA sequences in a suitable cloning vehicle. Fusion proteins are commonly used as a source of antigen for producing antibodies. Two widely used expression systems for *E. coli* are lacZ fusions using the pUR series of vectors and trpE fusions using the pATH vectors. The proteins can be purified, and then coupled to a carrier protein and mixed with Freund's adjuvant (to help stimulate the antigenic response by the animal of choice) and injected into rabbits or other laboratory animals. Alternatively, protein can be isolated from XAF expressing cultured cells. Following booster injections at bi-weekly intervals, the rabbits or other laboratory animals are then bled and the sera isolated. The sera can be used directly or can be purified prior to use, by various methods including affinity chromatography employing reagents such as Protein A-Sepharose, Antigen Sepharose, and Anti-mouse-Ig-Sepharose. The sera can then be used to probe protein extracts from XAF expressing tissues run on a polyacrylamide gel to identify XAF proteins. Alternatively, synthetic peptides can be made that correspond to the antigenic portions of the protein and used to innoculate the animals.

In order to generate peptide or full-length protein for use in making, for example, XAF-1 -specific antibodies, a XAF-1 coding sequence can be expressed as a C-terminal fusion with glutathione S-transferase (GST; Smith et al., Gene 67: 31–40, 1988). The fusion protein can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titers are monitored by Western blot and immunoprecipitation analyses using the thrombin-cleaved XAF-1 fragment of the GST-XAF-1 fusion protein. Immune sera are affinity purified using CNBr-Sepharose-coupled XAF-1 protein. Antiserum specificity is determined using a panel of unrelated GST proteins (including GSTp53, Rb, HPV-16 E6, and E6-AP) and GST-trypsin (which was generated by PCR using known sequences).

It is also understood by those skilled in the art that monoclonal XAF antibodies may be produced by using as antigen XAF protein isolated from XAF expressing cultured cells or XAF protein isolated from tissues. The cell extracts, or recombinant protein extracts, containing XAF protein, may for example, be injected with Freund's adjuvant into mice. After being injected, the mice spleens may be removed and resuspended in phosphate buffered saline (PBS). The spleen cells serve as a source of lymphocytes, some of which are producing antibody of the appropriate specificity. These are then fused with a permanently growing myeloma partner cells, and the products of the fusion are plated into a number of tissue culture wells in the presence of a selective agent such as hypoxanthine, aminopterine, and thymidine (HAT). The wells are then screened by ELISA to identify those containing cells making antibody capable of binding a XAF protein or polypeptide fragment or mutant thereof. These are then re-plated and after a period of growth, these wells are again screened to identify antibody-producing cells. Several cloning procedures are carried out until over 90% of the wells contain single clones which are positive for antibody production. From this procedure a stable line of clones which produce the antibody is established. The monoclonal antibody can then be purified by affinity chromatography using Protein A Sepharose, ion-exchange chromatography, as well as variations and combinations of these techniques. Truncated versions of monoclonal antibodies may also be produced by recombinant methods in which plasmids are generated which express the desired monoclonal antibody fragment(s) in a suitable host.

As an alternate or adjunct immunogen to GST fusion proteins, peptides corresponding to relatively unique hydrophilic regions of, for example, XAF-1 may be generated and coupled to keyhole limpet hemocyanin (KLH) through an introduced C-terminal lysine. Antiserum to each of these peptides is similarly affinity purified on peptides conjugated to BSA, and specificity is tested by ELISA and Western blotting using peptide conjugates, and by Western blotting and immunoprecipitation using XAF-1 expressed as a GST fusion protein.

Alternatively, monoclonal antibodies may be prepared using the XAF proteins described above and standard hybridoma technology (see, e.g., Kohler et al., Nature 256: 495, 1975; Kohler et al., Eur. J. Immunol. 6:511, 1976; Kohler et al., Eur. J. Immunol. 6: 292, 1976; Hammerling et al., In *Monoclonal Antibodies and T Cell Hybridomas*, Elsevier, New York, N.Y., 1981; Ausubel et al., supra). Once produced, monoclonal antibodies are also tested for specific XAF protein recognition by Western blot or immunoprecipitation analysis (by the methods described in Ausubel et al., supra).

Monoclonal and polyclonal antibodies that specifically recognize a XAF protein (or fragments thereof), such as those described herein containing a XAF-1 C-terminal domain, are considered useful in the invention. They may, for example, be used in an reporter gene assay to monitor the NF-κB inducing effects (via TRAF6) of a XAF protein. Antibodies that inhibit a XAF-1 described herein may be especially useful in preventing apoptosis in cells undergoing undesirable cell death or growth arrest.

Antibodies of the invention may be produced using XAF amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (CABIOS 4:181, 1988). These fragments can be generated by standard techniques, e.g., by the PCR, and cloned into the pGEX expression vector (Ausubel et al., supra). GST fusion proteins are expressed in *E. coli* and purified using a glutathione agarose affinity matrix as described in Ausubel et al. (supra). To generate rabbit polyclonal antibodies, and to minimize the potential for obtaining antisera that is non-specific, or exhibits low-affinity binding to a XAF, two or three fusions are generated for each protein, and each fusion is injected into at least two rabbits. Antisera are raised by injections in series, preferably including at least three booster injections.

In addition, antibodies of the invention may be produced using XAF amino acid sequences that do reside within highly conserved regions. For example, amino acid sequences from the N-terminal 150 amino acids of either XAF-1 or XAF-2 may be used as antigen to generate antibodies specific toward both XAF-1 and XAF-2, and possibly specific toward other members of the XAF family of proteins. These antibodies may be screened as described above.

In addition to intact monoclonal and polyclonal anti-XAF-1 antibodies, the invention features various genetically engineered antibodies, humanized antibodies, and antibody fragments, including F(ab')2, Fab', Fab, Fv and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., Nature Genetics 7: 13–21, 1994).

Ladner (U.S. Pat. Nos. 4,946,778 and 4,704,692) describes methods for preparing single polypeptide chain antibodies. Ward et al. (Nature 341: 544–546, 1989) describe the preparation of heavy chain variable domains, which they term "single domain antibodies," which have high antigen-binding affinities. McCafferty et al. (Nature 348: 552–554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies.

VII. Use of XAF Antibodies

Antibodies to XAF proteins may be used, as noted above, to detect XAF proteins or to inhibit the biological activities of XAF proteins. In addition, the antibodies may be coupled to compounds for diagnostic and/or therapeutic uses such as radionucleotides for imaging and therapy and liposomes for the targeting of compounds to a specific tissue location.

VIII. Detection of XAF Gene Expression

As noted, the antibodies described above may be used to monitor XAF protein expression. In addition, in situ hybridization is a method which may be used to detect the expression of XAF genes. In situ hybridization techniques, such as fluorescent in situ hybridization (FISH), rely upon the hybridization of a specifically labeled nucleic acid probe to the cellular RNA in individual cells or tissues. Therefore, it allows the identification of mRNA within intact tissues, such as the heart. In this method, oligonucleotides or cloned nucleotide (RNA or DNA) fragments corresponding to unique portions of XAF genes are used to detect specific mRNA species, e.g., in the heart. Numerous other gene expression detection techniques are known to those of skill in the art and may be employed here.

IX. Identification of Compounds that Modulate XAF Protein Expression

Based on our experimental results, we have developed a number of screening procedures for identifying therapeutic compounds (e.g., anti-apoptotic or apoptotic-inducing) which can be used in human patients. In particular examples, compounds that down regulate expression of XAF proteins are considered useful in the invention for treatment of diseases hallmarked by an excessive amount of apoptosis, such as neurodegenerative disorders. Similarly, compounds that up regulate or activate XAF proteins are also considered useful as drugs for the treatment of diseases hallmarked by impaired apoptosis, such as cancer. In general, the screening methods of the invention involve screening any number of compounds for therapeutically active agents by employing any number of in vitro or in vivo experimental systems.

The methods of the invention simplify the evaluation, identification, and development of active agents for the treatment and prevention of conditions involving an inappropriate amount of apoptosis, which may be excessive or insufficient, depending upon the condition. These screening methods provide a facile means for selecting natural product extracts or compounds of interest from a large population which are further evaluated and condensed to a few active and selective materials. Constituents of this pool are then purified and evaluated in the methods of the invention to determine their anti-apoptotic or apoptotic-inducing activities.

In general, novel drugs for the treatment of conditions involving an appropriate level of apoptosis are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, NH) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-apoptotic or apoptotic-inducing activities should be employed whenever possible.

When a crude extract is found to have anti-apoptotic or apoptotic-inducing activities or both, further fractionation of the positive lead extract is necessary to isolate chemical constituents responsible for the observed effect. Thus, the goal of the extraction, fractionation, and purification process is the careful characterization and identification of a chemical entity within the crude extract having anti-apoptotic or apoptotic-inducing activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of degenerative disease or cancer known in the art.

Below we describe screening methods for identifying and evaluating the efficacy of a compound as an anti-apoptotic or apoptotic-inducing agent. These methods are intended to illustrate, not limit, the scope of the claimed invention.

a) Screens for Compounds Affecting XAF Protein Expression

XAF cDNAs may be used to facilitate the identification of compounds that increase or decrease XAF protein expression. In one approach, candidate compounds are added, in varying concentrations, to the culture medium of cells expressing XAF mRNA. The XAF mRNA expression is then measured, for example, by Northern blot analysis (Ausubel et al., supra) using a XAF DNA, or cDNA or RNA fragment, as a hybridization probe. The level of XAF mRNA expression in the presence of the candidate compound is compared to the level of XAF mRNA expression in the absence of the candidate compound, all other factors (e.g., cell type and culture conditions) being equal.

The effect of candidate compounds on XAF-mediated apoptosis may, instead, be measured at the level of translation by using the general approach described above with standard protein detection techniques, such as Western blotting or immunoprecipitation with a XAF-specific antibody (for example, the XAF-1 specific antibody described herein).

In an alternative approach to detecting compounds which regulate XAF at the level of transcription, candidate compounds may be tested for an ability to regulate a reporter gene whose expression is directed by a XAF gene promoter. For example, a cell unlikely to undergo apoptosis may be transfected with a expression plasmid that includes a luciferase reporter gene operably linked to the XAF-1 promoter. Candidate compounds may then be added, in varying concentrations, to the culture medium of the cells. Luciferase expression levels may then be measured by subjecting the compound-treated transfected cells to standard luciferase assays known in the art, such as the luciferase assay system kit used herein that is commercially available from Promega, and rapidly assessing the level of luciferase activity on a luminometer. The level of luciferase expression in the presence of the candidate compound is compared to the level of luciferase expression in the absence of the candidate compound, all other factors (e.g., cell type and culture conditions) being equal.

Compounds that modulate the level of XAF protein expression may be purified, or substantially purified, or may be one component of a mixture of compounds such as an extract or supernatant obtained from cells, from mammalian serum, or from growth medium in which mammalian cells have been cultured (Ausubel et al., supra). In an assay of a mixture of compounds, XAF protein expression is tested against progressively smaller subsets of the compound pool (e.g., produced by standard purification techniques such as HPLC or FPLC) until a single compound or minimal number of effective compounds is demonstrated to modulate XAF protein expression.

b) Screens for Compounds Affecting XAF Biological Activity

Compounds may also be screened for their ability to modulate, for example, XAF-1 apoptosis inducing activity. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the apoptosis-inducing activity of XAF has been to screen for compounds that interact physically with a given XAF polypeptide, e.g., XAF-1. These compounds were detected by adapting yeast two-hybrid expression systems known in the art. These systems detected protein interactions using a transcriptional activation assay and are generally described by Gyuris et al. (Cell 75:791–803, 1993) and Field et al. (Nature 340:245–246, 1989), and are commercially available from Clontech (Palo Alto, Calif.). In addition, PCT Publication WO 95/28497 describes a yeast two-hybrid assay in which proteins involved in apoptosis, by virtue of their interaction with BCL-2, were detected. A similar method has been used to identify proteins and other compounds that interacted with XAF-1, and is used to identify XAF-2 splice variant interactors.

A compound that promotes an increase in the expression or biological activity of the XAF protein, e.g., XAF-1, is considered particularly useful in the invention; such a molecule may be used, for example, as a therapeutic to increase cellular levels of XAF-1 and thereby exploit the ability of XAF-1 polypeptides to induce apoptosis. This would be advantageous in the treatment of diseases involving insufficient apoptosis (e.g., cancer).

A compound that decreases XAF-1 activity (e.g., by decreasing XAF-1 gene expression or biological activity) may also be used to increase cellular proliferation. This would be advantageous in the treatment of degenerative diseases, such as neurodegenerative diseases (e.g., Alzheimer's disease, Huntington's disease) or other tissue-specific degenerative diseases (e.g., cirrhosis of the liver, T-lymphocyte depletion in AIDS, hair loss).

Molecules that are found, by the methods described above, to effectively modulate XAF gene expression or polypeptide activity may be tested further in animal models. If they continue to function successfully in an in vivo setting, they may be used as therapeutics to either inhibit or enhance apoptosis, as appropriate.

X. Therapies

Therapies may be designed to circumvent or overcome a XAF gene defect or inadequate XAF gene expression, and thus modulate and possibly alleviate conditions involving an inappropriate amount of apoptosis. XAF-1 is expressed in the every tissue looked at thus far. Hence, in considering various therapies, it is understood that such therapies may be targeted at any tissues demonstrated to express XAF-1. In particular, therapies to enhance XAF-1 gene expression are useful in promoting apoptosis in cancerous cells. Apoptosis-inducing XAF-1 reagents may include, without limitation, full length or fragment XAF-1 polypeptides, XAF-1 mRNA, or any compound which increases XAF-1 apoptosis-inducing activity.

a) Protein Therapy

Treatment or prevention of inappropriate apoptosis can be accomplished by replacing mutant or surplus XAF protein with normal protein, by modulating the function of mutant protein, or by delivering normal XAF protein to the appropriate cells. It is also be possible to modify the pathophysiologic pathway (e.g., a signal transduction pathway) in which the protein participates in order to correct the physiological defect.

To replace a mutant protein with normal protein, or to add protein to cells which no longer express sufficient XAF, it is necessary to obtain large amounts of pure XAF protein from cultured cell systems which can express the protein. Delivery of the protein to the affected tissues (e.g., cancerous tissues) can then be accomplished using appropriate packaging or administrating systems. Alternatively, small molecule analogs may be used and administered to act as XAF agonists and in this manner produce a desired physiological effect. Methods for finding such molecules are provided herein.

b) Gene Therapy Gene therapy is another potential therapeutic approach in which normal copies of the XAF gene or nucleic acid encoding XAF antisense RNA are introduced into selected tissues to successfully encode for normal and abundant protein or XAF antisense RNA in cells which inappropriately either suppress cell death (e.g., cancerous ovarian cells) or enhance the rate of cell death (e.g., neuronal cell death leading to disease), respectively. The gene must be delivered to those cells in a form in which it can be taken up and encode for sufficient protein to provide effective function. Alternatively, in some mutants it may be possible to promote apoptosis by introducing another copy of the homologous gene bearing a second mutation in that gene or to alter the mutation, or use another gene to block any negative effect.

Transducing retroviral vectors can be used for somatic cell gene therapy especially because of their high efficiency of infection and stable integration and expression. The targeted cells however must be able to divide and the expression levels of normal protein should be high. For example, the full length XAF-1 gene, or portions thereof, can be cloned into a retroviral vector and driven from its endogenous promoter or from the retroviral long terminal repeat or from a promoter specific for the target cell type of interest (such as neurons). Other viral vectors which can be used include adenovirus, adeno-associated virus, vaccinia virus, bovine papilloma virus, or a herpes virus such as Epstein-Barr Virus.

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are lower efficiency.

Transplantation of normal genes into the affected cells of a patient can also be useful therapy. In this procedure, a normal XAF gene is transferred into a cultivatable cell type, either exogenously or endogenously to the patient. These cells are then injected serotologically into the targeted tissue(s).

Retroviral vectors, adenoviral vectors, adenovirus-associated viral vectors, or other viral vectors with the appropriate tropism for cells likely to be involved in apoptosis (for example, epithelial cells) may be used as a gene transfer delivery system for a therapeutic XAF gene construct. Numerous vectors useful for this purpose are generally known (Miller, Human Gene Therapy 15–14, 1990; Friedman, Science 244:1275–1281, 1989; Eglitis and Anderson, BioTechniques 6: 608–614, 1988; Tolstoshev and Anderson, Curr. Opin. Biotech. 1: 55–61, 1990; Sharp, The Lancet 337: 1277–1278, 1991; Cornetta et al., Nucl. Acid Res. and Mol. Biol. 36: 311–322, 1987; Anderson, Science 226: 401–409, 1984; Moen, Blood Cells 17: 407–416, 1991; Miller et al., Biotech. 7: 980–990, 1989; Le Gal La Salle et al., Science 259: 988–990, 1993; and Johnson, Chest 107: 77S-83S, 1995). Retroviral vectors are particularly well developed and have been used in clinical settings (Rosenberg et al., N. Engl. J. Med 323: 370, 1990; Anderson et al., U.S. Pat. No. 5,399,346). Non-viral approaches may also be employed for the introduction of therapeutic DNA into cells otherwise predicted to undergo apoptosis. For example, XAF may be introduced into a neuron or a T cell by lipofection (Felgner et al., Proc. Natl. Acad. Sci. USA 84: 7413, 1987; Ono et al., Neurosci. Lett. 117: 259, 1990; Brigham et al., Am. J. Med. Sci. 298: 278, 1989; Staubinger et al.; Meth. Enz. 101:512, 1983, asialorosonucoid-polylysine conjugation (Wu et al., J. Biol. Chem. 263: 14621, 1988; Wu et al., J. Biol. Chem. 264: 16985, 1989); or, less preferably, micro-injection under surgical conditions (Wolff et al., Science 247: 1465, 1990).

In another approach that may be utilized with all of the above methods, a therapeutic XAF DNA construct is preferably applied to the site of the desired apoptosis event (for example, by injection). However, it may also be applied to tissue in the vicinity of the desired apoptosis event or to a blood vessel supplying the cells (e.g., cancerous cells) desired to undergo apoptosis.

In the constructs described, XAF cDNA expression can be directed from any suitable promoter (e.g., the human cytomegalovirus (CMV), simian virus 40 (SV40), or met-allothionein promoters), and regulated by any appropriate mammalian regulatory element. For example, if desired, enhancers known to preferentially direct gene expression in neural cells, lymphocytes, or muscle cells may be used to direct XAF expression. The enhancers used could include, without limitation, those that are characterized as tissue- or cell-specific in their expression. Alternatively, if a XAF genomic clone is used as a therapeutic construct (for example, following isolation by hybridization with the XAF cDNA described above), regulation may be mediated by the cognate regulatory sequences or, if desired, by regulatory sequences derived from a heterologous source, including any of the promoters or regulatory elements described above.

Antisense based strategies have employed to explore XAF gene function and as a basis for therapeutic drug design. The principle is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target XAF mRNA. Antisense strategies may use a variety of approaches including the use of antisense oligonucleotides and injection of antisense RNA. For our analysis of XAF-1 gene function, we employed the method of transfection of antisense RNA expression vectors into targeted cells. Antisense effects can be induced by control (sense) sequences, however, the extent of phenotypic changes are highly variable. Phenotypic effects induced by antisense effects are based on changes in criteria such as protein levels, protein activity measurement, and target mRNA levels.

For example, XAF-1 gene therapy may also be accomplished by direct administration of antisense XAF-1 mRNA to a cell that is expected to undergo undesired apoptosis. The antisense XAF-1 mRNA may be produced and isolated by any standard technique, but is most readily produced by in vitro transcription using an antisense XAF-1 cDNA under the control of a high efficiency promoter (e.g., the T7 promoter). Administration of antisense XAF-1 mRNA to cells can be carried out by any of the methods for direct nucleic acid administration described above.

Another therapeutic approach within the invention involves administration of recombinant XAF polypeptide, either directly to the site of a desired apoptosis event (for example, by injection) or systemically (for example, by any conventional recombinant protein administration technique). The dosage of XAF depends on a number of factors, including the size and health of the individual patient, but, generally, between 0.1 mg and 100 mg inclusive are administered per day to an adult in any pharmaceutically acceptable formulation.

XI. Administration of XAF Polypeptides, XAF Genes, or Modulators of XAF Synthesis or Function A XAF protein, gene, or modulator may be administered within a pharmaceutically-acceptable diluent, carrier, or excipient, in unit dosage form. Conventional pharmaceutical practice may be employed to provide suitable formulations or compositions to administer neutralizing XAF antibodies or XAF-inhibiting compounds (e.g., antisense XAF-1 or a XAF-1 dominant negative mutant) to patients suffering from a disease (e.g., a degenerative disease) that is caused by excessive apoptosis. Administration may begin before the patient is symptomatic. Any appropriate route of administration may be employed, for example, administration may be parenteral, intravenous, intra-arterial, subcutaneous, intramuscular, intracranial, intraorbital, ophthalmic, intraveutricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington's Pharmaceutical Sciences,* (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for XAF modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a XAF protein, gene, or modulatory compound may be combined with more traditional therapies for the disease involving excessive apoptosis, such as surgery, steroid therapy, or chemotherapy for autoimmune disease; antiviral therapy for AIDS; and tissue plasminogen activator (TPA) for ischemic injury. Likewise, treatment with a XAF protein, gene, or modulatory compound may be combined with more traditional therapies for the disease involving insufficient apoptosis, such as surgery, radiation therapy, and chemotherapy for cancer.

XII. Detection of Conditions Involving Altered Apoptosis

XAF polypeptides and nucleic acid sequences find diagnostic use in the detection or monitoring of conditions involving aberrant levels of apoptosis. For example, decreased expression of XAF-1 may be correlated with decreased apoptosis in humans. Accordingly, a decrease or increase in the level of XAF-1 production may provide an indication of a deleterious condition. Levels of XAF expression may be assayed by any standard technique. For example, XAF expression in a biological sample (e.g., a biopsy) may be monitored by standard Northern blot analysis or may be aided by PCR (see, e.g., Ausubel et al., supra; *PCR Technology: Principles and Applications for DNA Amplification,* H. A. Ehrlich, Ed. Stockton Press, NY; Yap et al. Nucl. Acids. Res. 19: 4294, 1991).

Alternatively, a biological sample obtained from a patient may be analyzed for one or more mutations in XAF nucleic acid sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant XAF detection, and each is well known in the art; examples of particular techniques are described, without limitation, in Orita et al. (Proc. Natl. Acad. Sci. USA 86: 2766–2770, 1989) and Sheffield et al. (Proc. Natl. Acad. Sci. USA 86: 232–236, 1989).

In yet another approach, immunoassays are used to detect or monitor XAF protein expression in a biological sample. XAF-specific polyclonal or monoclonal antibodies (produced as described above) may be used in any standard immunoassay format (e.g., ELISA, Western blot, or RIA) to measure XAF polypeptide levels. These levels would be compared to wild-type XAF levels. For example, a decrease in XAF-1 production may indicate a condition involving insufficient apoptosis. Examples of immunoassays are described, e.g., in Ausubel et al., supra. Immunohistochemical techniques may also be utilized for XAF detection. For example, a tissue sample may be obtained from a patient, sectioned, and stained for the presence of XAF using an anti-XAF antibody and any standard detection system (e.g., one which includes a secondary antibody conjugated to horseradish peroxidase). General guidance regarding such techniques can be found in, e.g., Bancroft and Stevens (*Theory and Practice of Histological Techniques,* Churchill Livingstone, 1982) and Ausubel et al. (supra).

In one preferred example, a combined diagnostic method may be employed that begins with an evaluation of XAF protein production (for example, by immunological techniques or the protein truncation test (Hogerrorst et al., Nature Genetics 10: 208–212, 1995) and also includes a nucleic acid-based detection technique designed to identify more subtle XAF mutations (for example, point mutations). As described above, a number of mismatch detection assays are available to those skilled in the art, and any preferred technique may be used. Mutations in XAF may be detected that either result in loss of XAF expression or loss of normal XAF biological activity. In a variation of this combined diagnostic method, XAF-1 biological activity is measured as apoptotic-inducing activity using any appropriate apoptosis assay system (for example, those described herein).

Mismatch detection assays also provide an opportunity to diagnose a XAF-mediated predisposition to diseases caused by inappropriate apoptosis. For example, a patient heterozygous for a XAF-1 mutation that induces a XAF-1 overexpression may show no clinical symptoms and yet possess a higher than normal probability of developing one or more types of neurodegenerative, myelodysplastic or having severe sequelae to an ischemic event. Given this diagnosis, a patient may take precautions to minimize their exposure to adverse environmental factors (for example, UV exposure or chemical mutagens) and to carefully monitor their medical condition (for example, through frequent physical examinations). This type of XAF-1 diagnostic approach may also be used to detect XAF-1 mutations in prenatal screens. The XAF-1 diagnostic assays described above may be carried out using any biological sample (for example, any biopsy sample or other tissue) in which XAF-1 is normally expressed. Identification of a mutant XAF-1 gene may also be assayed using these sources for test samples.

Alternatively, a XAF mutation, particularly as part of a diagnosis for predisposition to XAF-associated degenerative disease, may be tested using a DNA sample from any cell, for example, by mismatch detection techniques. Preferably, the DNA sample is subjected to PCR amplification prior to analysis.

XIII. Preventative Anti-Apoptotic Therapy

In a patient diagnosed to be heterozygous for a XAF mutation or to be susceptible to XAF mutations or aberrant XAF expression (even if those mutations or expression patterns do not yet result in XAF overexpression or increased XAF biological activity), or a patient diagnosed with a degenerative disease (e.g., motor neuron degenerative diseases such as SMA or ALS diseases), or diagnosed as HIV positive, any of the above therapies may be administered before the occurrence of the disease phenotype. For example, the therapies may be provided to a patient who is HIV positive but does not yet show a diminished T cell count or other overt signs of AIDS. In particular, compounds shown to decrease XAF-1 expression or XAF-1 biological activity may be administered to patients diagnosed with degenerative diseases by any standard dosage and route of administration (see above). Alternatively, gene therapy using a antisense XAF-1 mRNA expression construct may be undertaken to reverse or prevent the cell defect prior to the development of the degenerative disease.

The methods of the instant invention may be used to reduce or diagnose the disorders described herein in any mammal, for example, humans, domestic, pets, or livestock. Where a non-human mammal is treated or diagnosed, the XAF polypeptide, nucleic acid, or antibody employed is preferably specific for that species.

XIV. Identification of Additional XAF Genes

Standard techniques, such as the polymerase chain reaction (PCR) and DNA hybridization, may be used to clone additional XAF homologues in other species. Southern blots of murine genomic DNA hybridized at low stringency with probes specific for human XAF reveal bands that correspond to XAF and/or related family members. Thus, additional XAF sequences may be readily identified using low stringency hybridization. Furthermore, murine and human XAF-specific primers may be used to clone additional XAF related genes by RT-PCR.

Thus far, we have identified multiple ESTs in the data base that have significant homology to XAF-1. From the EST sequences, we have made oligo primers and PCR cloned "XAF-2." The N terminus of the XAF-2 protein has five of the amino-terminal zinc fingers of XAF-1, with a unique carboxy terminus that has two additional RING zinc fingers, so that the entire XAF-2 protein, like XAF-1, has seven Zinc finger binding domains.

XV. Characterization of XAF Activity and Intracellular Localization Studies

The ability of XAF proteins to modulate apoptosis can be defined in in vitro systems in which alterations of apoptosis can be detected. Mammalian expression constructs carrying XAF cDNAs, which are either full-length or truncated, can be introduced into cell lines such as CHO, NIH 3T3, HL60, Rat-1, or Jurkat cells. In addition, SF9 insect cells may be used, in which case the XAF gene is preferentially expressed using an insect baculovirus expression system. Following transfection, apoptosis can be induced by standard methods, which include serum withdrawal, or application of staurosporine, menadione (which induces apoptosis via free radical formation), or anti-Fas or anti-TNF-R1 antibodies. As a control, cells are cultured under the same conditions as those induced to undergo apoptosis, but either not transfected, or transfected with a vector that lacks a XAF insert. The ability of each XAF construct to induce or inhibit apoptosis upon expression can be quantified by calculating the survival index of the cells, i.e., the ratio of surviving transfected cells to surviving control cells. These experiments can confirm the presence of apoptosis inducing activity of the full length XAF-1 protein and, as discussed below, can also be used to determine the functional region(s) of XAF-1 protein. These assays may also be performed in combination with the application of additional compounds in order to identify compounds that modulate apoptosis via XAF expression.

XVI. Examples of Additional Apoptosis Assays

Specific examples of apoptosis assays are also provided in the following references. Assays for apoptosis in lymphocytes are disclosed by: Li et al., "Induction of apoptosis in uninfected lymphocytes by HIV-1 Tat protein", Science 268: 429–431, 1995; Gibellini et al., "Tat-expressing Jurkat cells show an increased resistance to different apoptotic stimuli, including acute human immunodeficiency virus-type 1 (HIV-1) infection", Br. J. Haematol. 89: 24–33, 1995; Martinet al., "HIV-1 infection of human $CD4^+T$ cells in vitro. Differential induction of apoptosis in these cells." J. Immunol. 152:330–342, 1994; Terai et al., "Apoptosis as a mechanism of cell death in cultured T lymphoblasts acutely infected with HIV-1", J. Clin. Invest. 87: 1710–1715, 1991; Dhein et al., "Autocrine T-cell suicide mediated by APO-1/(Fas/CD95)", Nature 373: 438–441, 1995; Katsikis et al., "Fas antigen stimulation induces marked apoptosis of T lymphocytes in human immunodeficiency virus-infected individuals", J. Exp. Med. 1815:2029–2036, 1995; Westendorp et al., "Sensitization of T cells to CD95-mediated apoptosis by HIV-1 Tat and gp120", Nature 375:497, 1995; DeRossi et al., Virology 198:234–244, 1994.

Assays for apoptosis in fibroblasts are disclosed by: Vossbeck et al., "Direct transforming activity of TGF-beta on rat fibroblasts", Int. J. Cancer 61:92–97, 1995; Goruppi et al., "Dissection of c-myc domains involved in S phase induction of NIH3T3 fibroblasts", Oncogene 9:1537–44, 1994; Fernandez et al., "Differential sensitivity of normal and Ha-ras transformed C3H mouse embryo fibroblasts to tumor necrosis factor: induction of bcl-2, c-myc, and manganese superoxide dismutase in resistant cells", Oncogene 9:2009–2017, 1994; Harrington et al., "c-Myc-induced apoptosis in fibroblasts is inhibited by specific cytokines", EMBO J. 13:3286–3295, 1994; Itoh et al., "A novel protein domain required for apoptosis. Mutational analysis of human Fas antigen", J. Biol. Chem. 268:10932–10937, 1993.

Assays for apoptosis in neuronal cells are disclosed by: Melino et al., "Tissue transglutaminase and apoptosis: sense and antisense transfection studies with human neuroblastoma cells", Mol. Cell Biol. 14:6584–6596, 1994; Rosenbaum et al., "Evidence for hypoxia-induced, programmed cell death of cultured neurons", Ann. Neurol. 36:864–870, 1994; Sato et al., "Neuronal differentiation of PC12 cells as a result of prevention of cell death by bcl-2", J. Neurobiol. 25:1227–1234, 1994; Ferrari et al., "N-acetylcysteine D- and L-stereoisomers prevents apoptotic death of neuronal cells", J. Neurosci. 1516:2857–2866, 1995; Talley et al., "Tumor necrosis factor alpha-induced apoptosis in human neuronal cells: protection by the antioxidant N-acetylcysteine and the genes bcl-2 and crmA", Mol. Cell Biol. 1585:2359–2366, 1995; Talley et al., "Tumor Necrosis Factor Alpha-Induced Apoptosis in Human Neuronal Cells: Protection by the Antioxidant NAcetylcysteine and the Genes bcl-2 and crmA", Mol. Cell. Biol. 15:2359–2366, 1995; Walkinshaw et al., "Induction of apoptosis in catecholaminergic PC12 cells by L-DOPA. Implications for the treatment of Parkinson's disease.", J. Clin. Invest. 95:2458–2464, 1995.

Assays for apoptosis in insect cells are disclosed by: Clem et al., "Prevention of apoptosis by a baculovirus gene during infection of insect cells", Science 254:1388–1390, 1991; Crook et al., "An apoptosis-inhibiting baculovirus gene with a zinc finger-like motif", J. Virol. 67:2168–2174, 1993; Rabizadeh et al., "Expression of the baculovirus p35 gene inhibits mammalian neural cell death", J. Neurochem. 61:2318–2321, 1993; Birnbaum et al., "An apoptosis inhibiting gene from a nuclear polyhedrosis virus encoding a polypeptide with Cys/His sequence motifs", J. Virol. 68:2521–2528, 1994; Clem et al., Mol. Cell. Biol. 14:5212–5222, 1994.

XVII. Construction of a Transgenic Animal

Characterization of XAF genes provides information that is necessary for XAF knockout animal models to be developed by homologous recombination. Preferably, the model is a mammalian animal, most preferably a mouse. Similarly, an animal model of XAF overproduction may be generated by integrating one or more XAF sequences into the genome, according to standard transgenic techniques.

A replacement-type targeting vector, which would be used to create a knockout model, can be constructed using an isogenic genomic clone, for example, from a mouse strain such as 129/Sv (Stratagene Inc., LaJolla, Calif.). The targeting vector will be introduced into a suitably-derived line of embryonic stem (ES) cells by electroporation to generate ES cell lines that carry a profoundly truncated form of a AAF gene. To generate chimeric founder mice, the targeted cell lines will be injected into a mouse blastula stage embryo. Heterozygous offspring will be interbred to homozygosity. Knockout mice would provide the means, in vivo, to screen for therapeutic compounds that modulate apoptosis via a XAF-dependent pathway. Making such mice may require use of loxP sites if there are multiple copies of XAF genes (i.e., genes encoding XAF-1 and another XAF polypeptide) on the chromosome (see Sauer and Henderson, Nucleic Aids Res. 17: 147–61, 1989).

The following examples are to illustrate the invention. They are not meant to limit the invention in any way.

EXAMPLE I cDNA and Predicted Amino Acid Sequences of Cloned Human XAF-1

Yeast 2-hybrid analysis (see U.S. Ser. No. 08/511,485 and related applications) with XIAP as the 'bait' protein identified a 37 kDa, RING zinc finger protein termed XAF-1 (XIAP associated factor 1).

Methods

The plasmid pAS2-XIAP, which encodes the GAL4 DNA-binding domain fused to full-length XIAP, was constructed by inserting the coding region of full length XIAP into the pAS2 plasmid which is commercially available from Clontech. PAS2-XIAP was then used as bait (DNA-binding domain hybrid) in yeast two-hybrid screens of the human placenta cDNA library commercially available from Clontech. The yeast two-hybrid assay and isolation of positive clones and subsequent interaction analyses were carried out as described (PCT Publication WO 95/28497). DNA sequence was performed on an Applied Biosytems model 373A automated DNA sequencer.

Results

Shown in FIG. 1 is the complete nucleotide sequence of XAF-1 cDNA determined for the coding strand (SEQ ID NO: 1; EMBL accession number X99699) and is shown with its encoded protein below in single letter code (SEQ ID NO.: 2). The asterisk indicates the stop codon. The entire XAF-1 protein is predicted to have seven Zinc finger binding domains, six of which are located in the N-terminal 178 amino acids. XAF-1 displays significant homology to members of the TRAF family, particularly TRAF6, but lacks the TRAF-C and TRAF-N domains.

EXAMPLE II

Predicted Zinc Fingers of XAF-1 Amino-Terminus

Results

Shown on FIG. 2 is a schematic of the six predicted Zinc finger binding domains corresponding to the N-terminal 178 amino acids of XAF-1 (SEQ ID NO.: 6).

EXAMPLE III

Northern Blot Analysis of XAF-1 mRNA in Multiple Human Tissues

Methods

Using methods described in the art (see, for example, Ausubel, et al., supra), mRNA was collected from tissues from heart, brain, placenta, lunch, liver, skeletal muscle, kidney, pancreas, spleen, thymus, prostate, testis, ovary, small intestine, mucosal lining of the colon, and peripheral blood leukocytes. mRNA was also collected from the following cell lines:

HL-60. a promyelocytic leukemia;
HeLa/S3, a cervix epitheliod carcinoma;
K-562, a chronic myelogenous leukemia;
MOLT-4, a lymphobastic leukemia;
Raji, a Burkitt's lymphoma;
SW480, a colorectal adenocarcinoma;
A549, a lung carcinoma; and
G361, a melanoma.

The mRNA samples were electrophoretically resolved and transferred to a nitrocellulose membrane, which was then subjected to Northern blot analysis for the presence and expression levels of XAF-1 mRNA using radioisotope labeled XAF-1 cDNA as a probe (as described in Ausubel, et al., supra).

Additional mRNA was also collected from lung, trachea, and placenta, as well as various subunits of the brain, heart, testis, kidney, and fetal tissue. RNA from yeast and E. coli bacteria was also collected. This RNA, as well as DNA collected from human, E. coli bacteria, and yeast, was dot-blotted on a dot-blot apparatus, electrophoretically transferred to a nitrocellulose membrane, and probed with radioisotope labeled XAF-1 cDNA for the presence and expression levels of XAF-1 mRNA.

Figure 3:
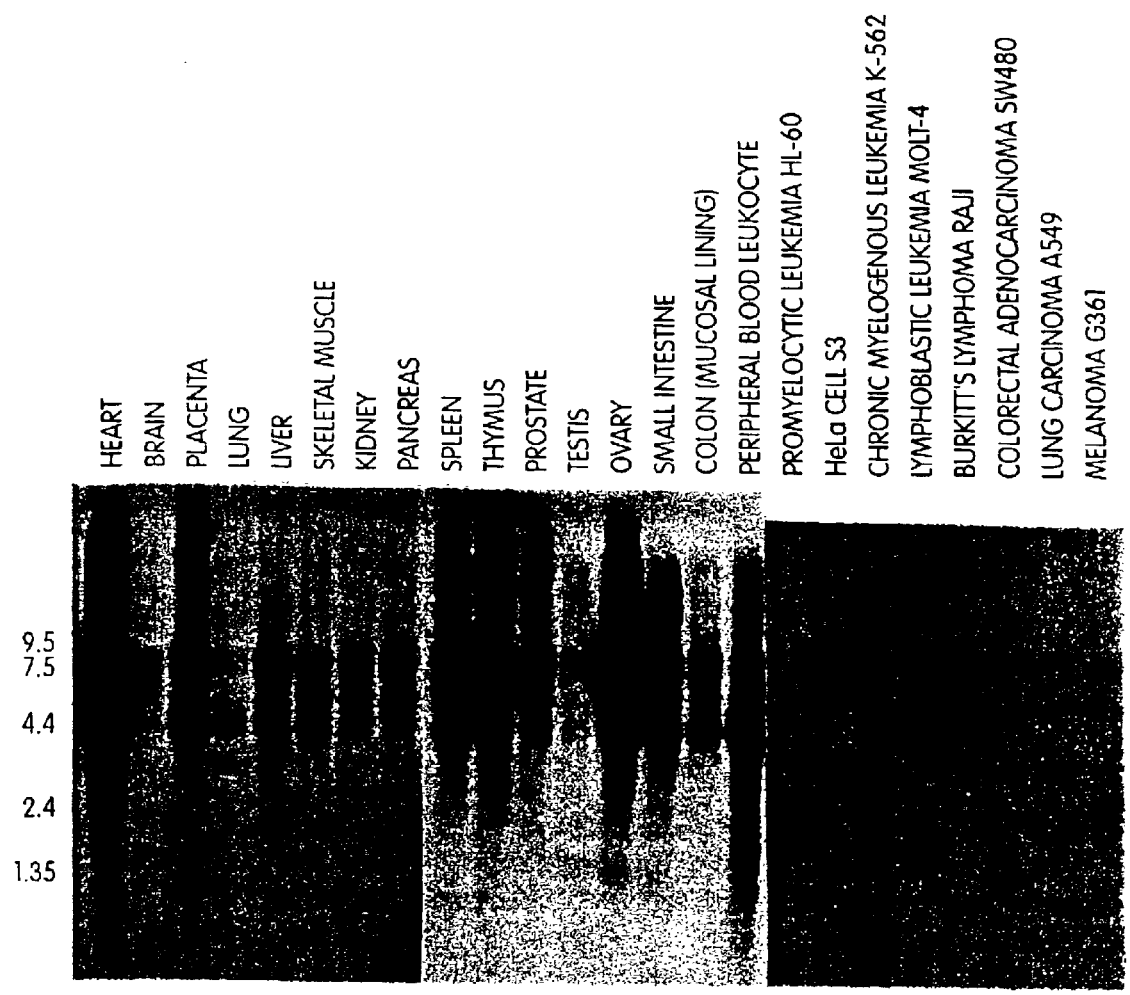
FIG. 3 is a Northern blot analysis of XAF-1 mRNA in multiple human tissues and various cell lines.

Results mRNA encoding XAF-1 is clearly expressed in normal cells in various tissues. FIG. 3 shows a Northern blotting analysis reveals XAF-1 mRNA to be widely distributed among the various tissues tested, with expression levels highest in the heart, placenta, spleen, thymus, ovary, small intestine, mucosal lining of the colon, and peripheral blood leukocytes. XAF-1 mRNA is also present in K-562 and MOLT-4 leukemic cell lines.

The dot-blot analysis of various tissues shown in FIG. 4 reveals that XAF-1 mRNA is widely distributed among the various indicated regions of the brain, heart, testes, kidney, lung, trachea, placenta, and fetal tissue. XAF-1 mRNA is not found, however, in yeast or the E. coli strain of bacteria.

EXAMPLE IV

Genomic Southern Blot Analysis of XAF-1

Methods

Genomic DNA was prepared from HEC38-0 human endometrial adenocarcinoma cells available from the ATCC (Bethesda, Md.) and Raji cells, digested with BamH1, EcoR1 and HindIII restriction endonucleases, electrophoretically resolved and transferred to a nitrocellulose membrane. Membrane bound DNA was subjected to Southern blot analysis using radioisotope labeled XAF-1 cDNA as a probe.

Results

Figure 5:
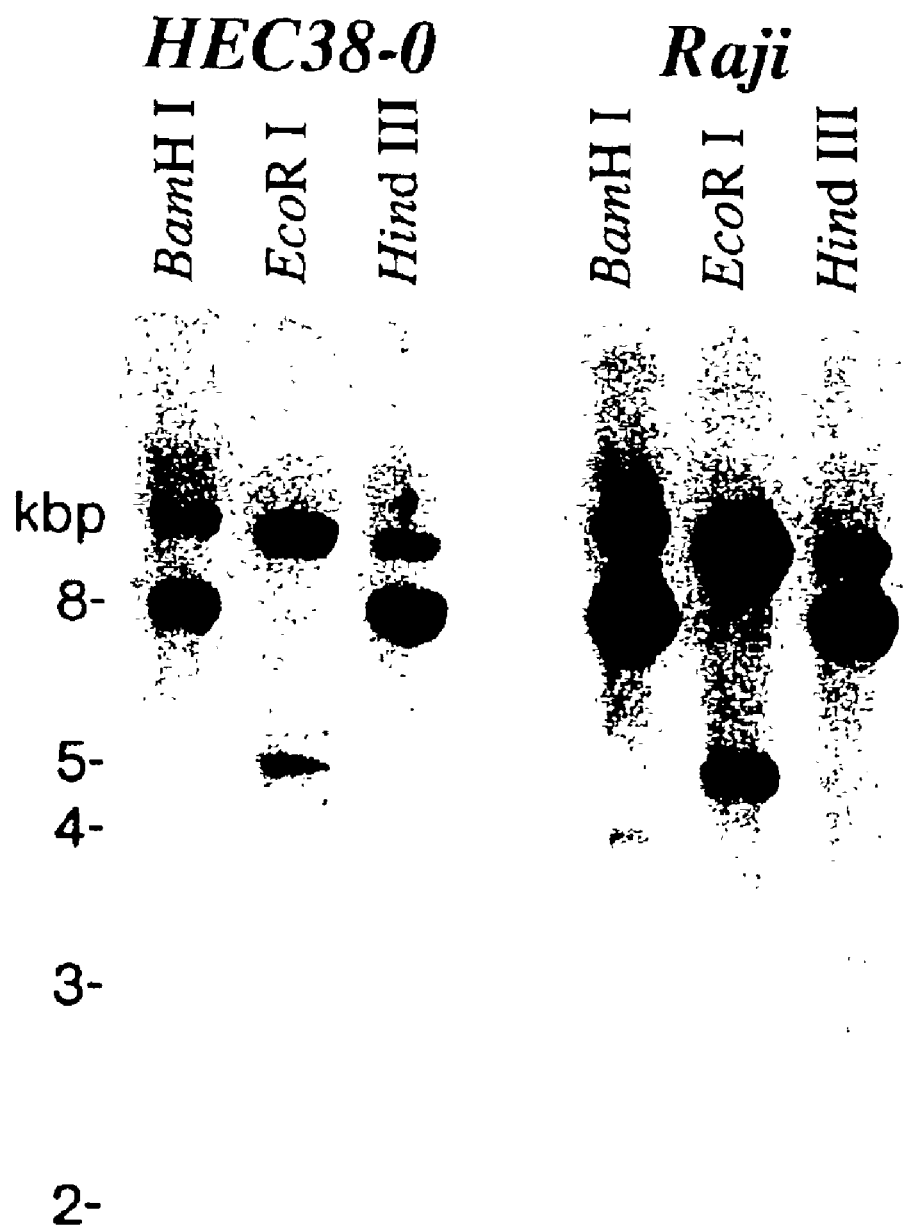
FIG. 5 is a genomic Southern blot analysis of XAF-1.

As shown in FIG. 5, the gene encoding XAF-1 appears to be limited in copy number in the human genome and is the same in both HEC38-0 and Raji cells, indicating that there is most likely only one gene encoding XAF-1, and that this gene is the same in the two cell lines assayed.

EXAMPLE V

Western Blot Analysis of XAF-1 Protein in Various Cell Lines

Methods

A number of transformed, immortalized and a primary cell line were tested by Western blot analysis for the presence and expression levels of XAF-1 protein using mouse polyclonal anti-XAF-1 antisera, which were obtained by providing GST-fusion proteins of XAF-1 and XIAP to the MBL Co., Ltd. (Japan) for use as immunogens. Cells were lysed, and lysates SDS-PAGE resolved, electrophoretically transferred to a nylon membrane, and immunoblotted with anti-XAF-1 polyclonal antisera. The membrane-bound proteins were then blotted with commercially available horseradish peroxidase conjugated anti-mouse secondary antibody and visualized with a chemiluminescent substrate.

The cell lines used in Western blotting analysis were:

HeLa: Epitheliod carcinoma, cervix, human;
A431: Epidermoid carcinoma, human;
SUDHL6: Hodgkin's lymphoma, human;
P19: Embryonal carcinoma, mouse;
cos-7: Kidney fibroblast, SV40 transformed, African green monkey;
293T: Adenovirus type 5 transformed primary embryonal kidney, human;
CHO: Chinese hamster ovary;

For use as a positive control for Western blotting analysis, 293T cells transiently expressing a myc-tagged XAF-1 protein were generated by the following method:

293T cells ($2 \times 10^5$) were transfected with 4 $\mu$g of plasmid DNA encoding XAF-1 by standard lipofection methods using Trans-IT lipofection reagent commercially available from Mirus.

Results

Figure 6:
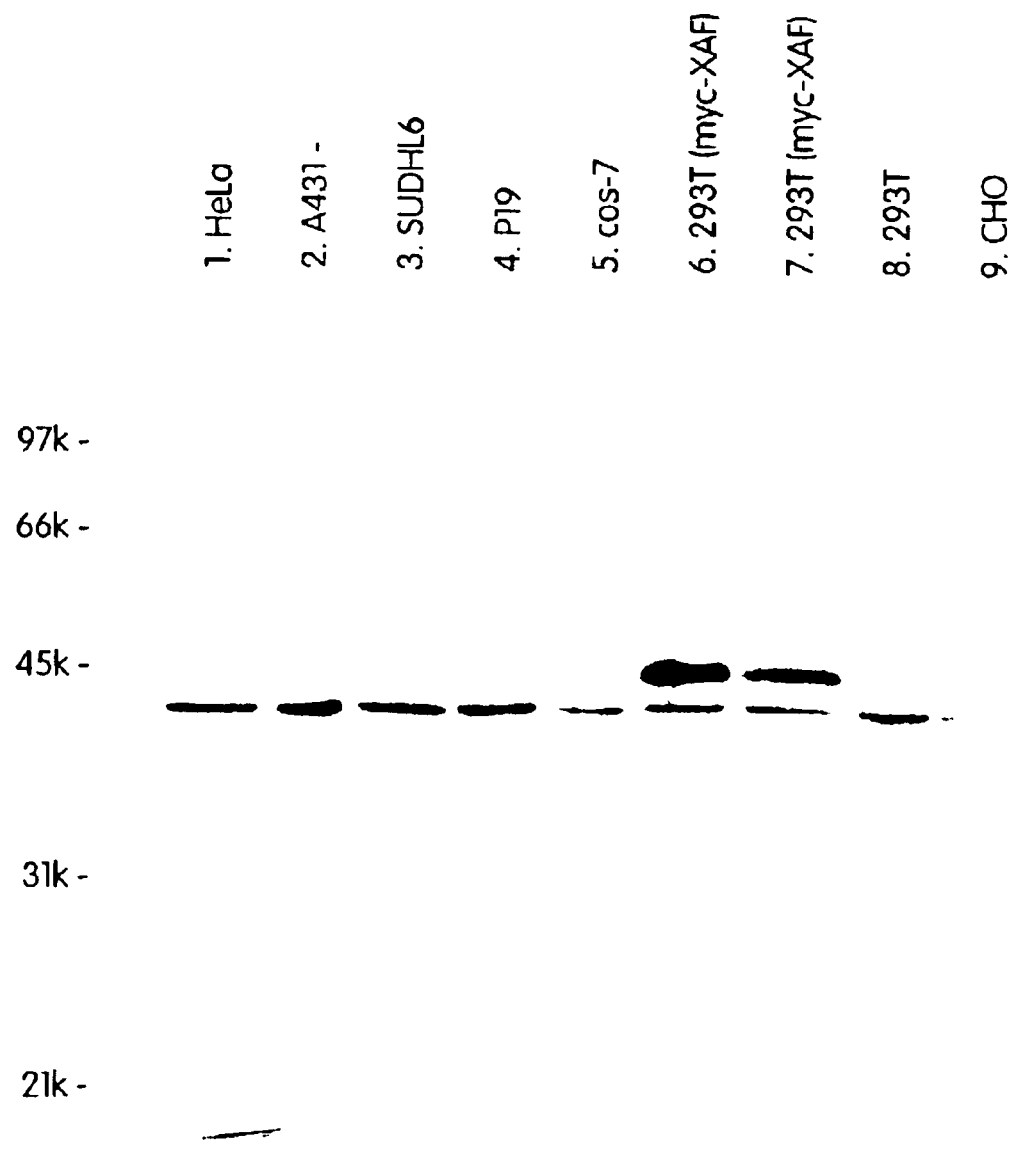
FIG. 6 is a Western blotting analysis of XAF-1 protein expression level in various cell lines.

Shown in FIG. 6 is the Western blotting analysis of the various cell lines for XAF-1 expression. By this type of analysis, XAF-1 expression appears to be ubiquitous, with low levels seen in a number of transformed cell lines.

EXAMPLE VI

XAF-1 Constructs and Expression

Methods

Mammalian expression vectors encoding full length XAF-1, the N-terminal 173 amino acids of XAF-1 containing six potential zinc fingers, including the region with significant homology to TRAF4 and TRAF6 (XAF-1N; SEQ ID NO.: 7), the C-terminal 173–317 amino acids of XAF-1 containing a single potential zinc finger domain (XAF-1C; SEQ ID NO.: 8) were constructed by insertion of each coding region into the pcDNA3-myc expression vector which contains an N-terminal c-myc epitope sequence (similar vectors are commercially available from Invitrogen). To generate the XAF-1 antisense construct, a 720 bp fragment of XAF-1 corresponding to 723-1 nucleotides (non-coding orientation) was cloned into the pcDNA3 expression vector (Invitrogen).

293T cells ($2 \times 10^5$) were transiently transfected with 4 $\mu$g of plasmid DNA encoding XAF-1, XAF-1N, or XAF-1C by standard lipofection methods using Trans-IT lipofection reagent commercially available from Mirus. About 48 hours following transfection, the cells were lysed, and $10^6$ cell equivalents were resolved by SDS-PAGE and electrophoretically transferred to a nylon membrane. The membrane-bound proteins were then immunoblotted with an anti-myc monoclonal antibody (9E10) (commercially available from Amersham Life Sciences), followed by a commercially available horseradish peroxidase conjugated secondary anti-mouse antibody. Immunoreactive proteins were visualized by chemluminescence following addition of substrate.

Results

Figure 7:
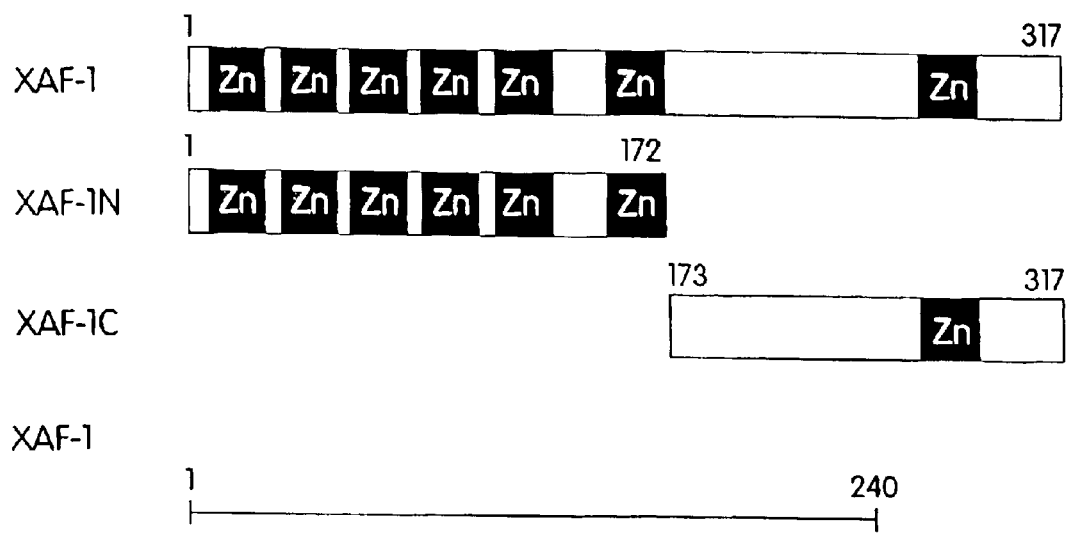
FIG. 7 are schematic diagrams of XAF-1 constructs.

Shown in FIG. 7 are schematic diagrams of the polypeptides encoded for by the various XAF-1 constructs. Although XAF-1 antisense is shown here in the "coding" orientation, in the vector, it inserted and expressed in the "non-coding" orientation.

Figure 8:
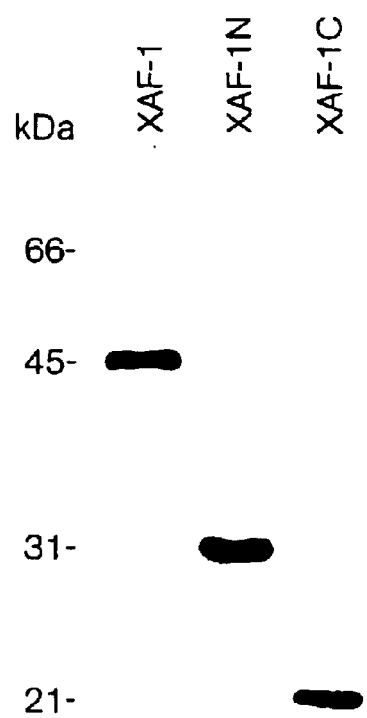
FIG. 8 is a Western blotting analysis of XAF-1, XAF-1N (SEQ ID NO.: 7) and XAF-1C (SEQ ID NO.: 8) protein expression levels when transiently expressed in 293T cells.

Shown in FIG. 8 is the Western blot analysis of 293T cells transiently transfected with XAF-1, XAF-1N and XAF-1C probed with anti-c-myc antibody. The expressed proteins show correct electrophoretic mobility predicted from the amino acid sequences.

EXAMPLE VII

Effect of XAF-1 Overexpression on Cell Survival

Methods

Recombinant adenoviruses were constructed that overexpress either the LacZ protein (negative control), p53 (positive control for cell cycle arrest), or the XAF-1 protein. HeLa (cervical carcinoma, available from the ATCC, Bethesda, Md.) and HEL (human embryonic in lung epithelial cells, available from the ATCC, Bethesda, Md.) were infected with recombinant adenovirus at a multiplicity of infection (MOI) of 10. Triplicate samples of infected cells were harvested at t=0, 24, 48, 72, and 96 hours post infection. Cell viability was assessed using standard MTT assays. Briefly, the media was removed from the well and replaced with $\frac{1}{10}$ volume of MTT (3-[4,5-dimethylthiazol-2-yl]-2,5-diphenyltetrazoleum bromide, available from Sigma) in phosphate buffered saline and incubated at 37° C. for 4 hours. Converted dye was then extracted using acidic isopropanol (0.1 N HCl in 100% isopropanol) and absorbance determined at 570 nm in a spectrophotometer. Conversion of the substrate to the 570 nm absorbing dye is carried out by mitochondrial enzymes active in living, but not dead cells.

The methods are further described in: Carmichael, J. et al., (1987) Cancer Res. 47:936–942 and Miyake, S et al., (1996) Proc. Natl. Acad. Sci. USA 93:1320–1324.

Results

Figure 9:
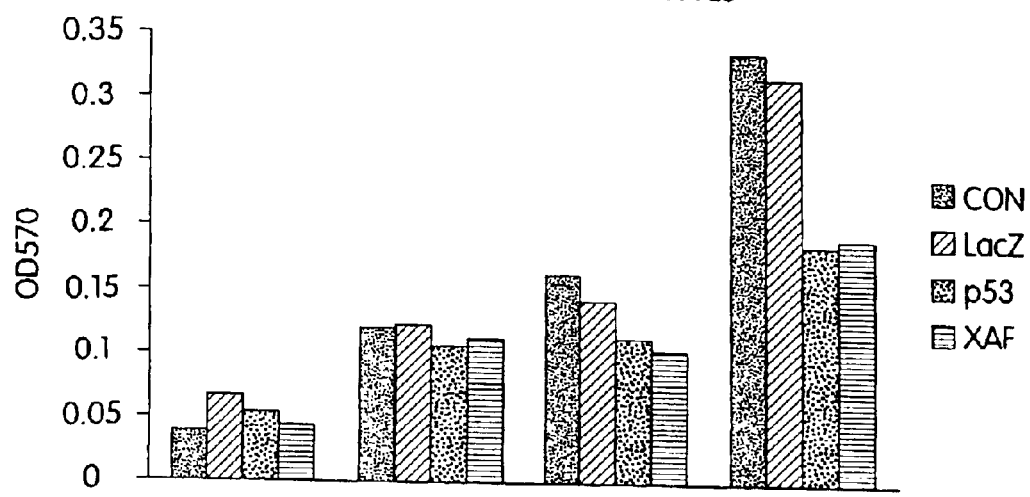
FIG. 9 is a graph of showing the effect of p53 and XAF overexpression on survival of HEL cells.
Figure 10:
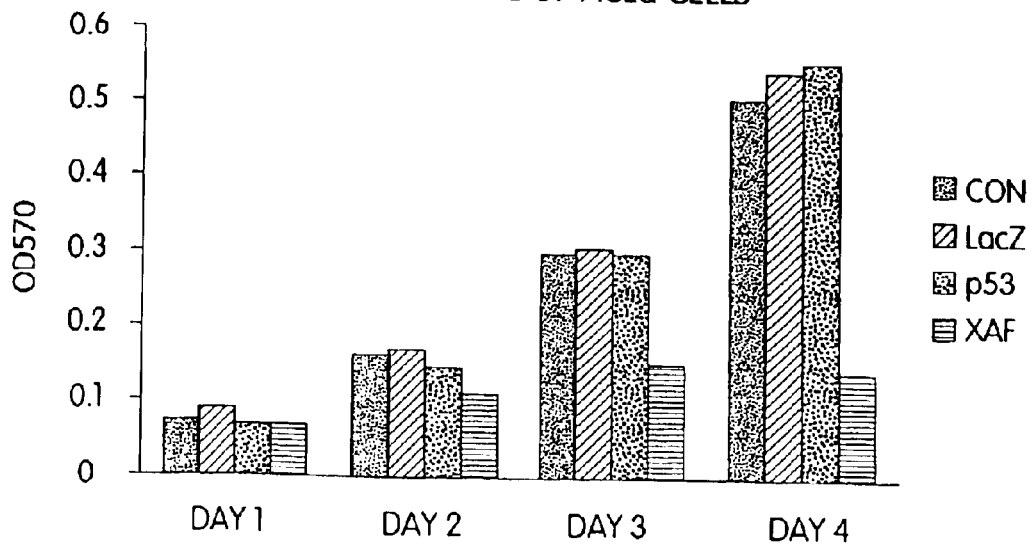
FIG. 10 shows the effect of p53 and XAF overexpression on survival of HeLa cells.

As seen in FIGS. 9 and 10, adenovirus-LacZ had no effect on cell viability (compare to the control, CON, which were not infected). In contrast, p53 induced a profound decrease in the number of viable cells when primary HEL cells are used (FIG. 9), but not in the HeLa cancer cell line (FIG. 10).

Figure 11A:
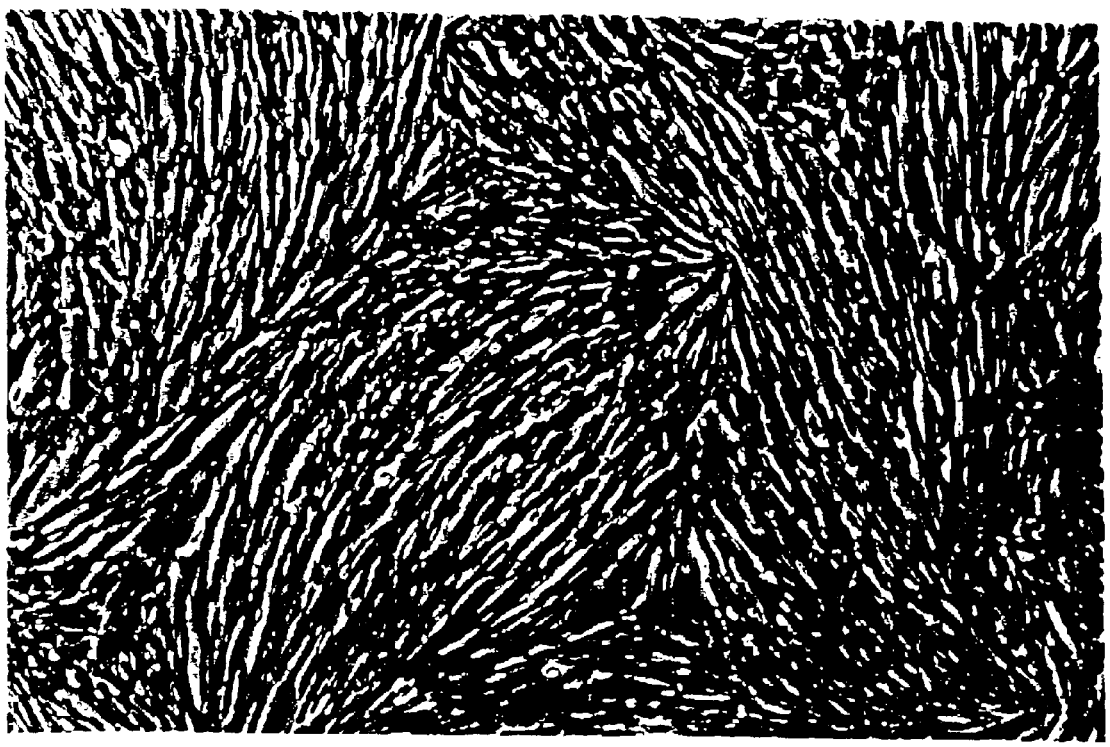
FIGS. 11A, 11B, and 11C show photographs of HEL cells infected with adeno-LacZ, adeno-p53 and adeno-XAF-1, respectively.
Figure 11B:
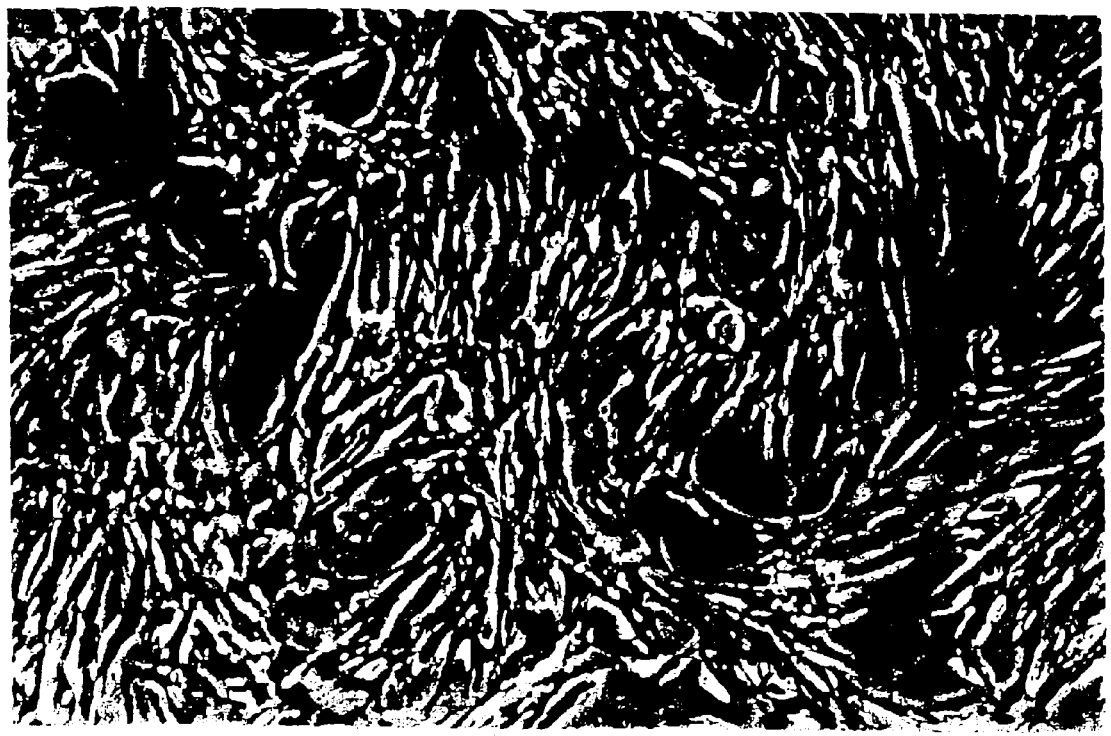
Figure 11C:
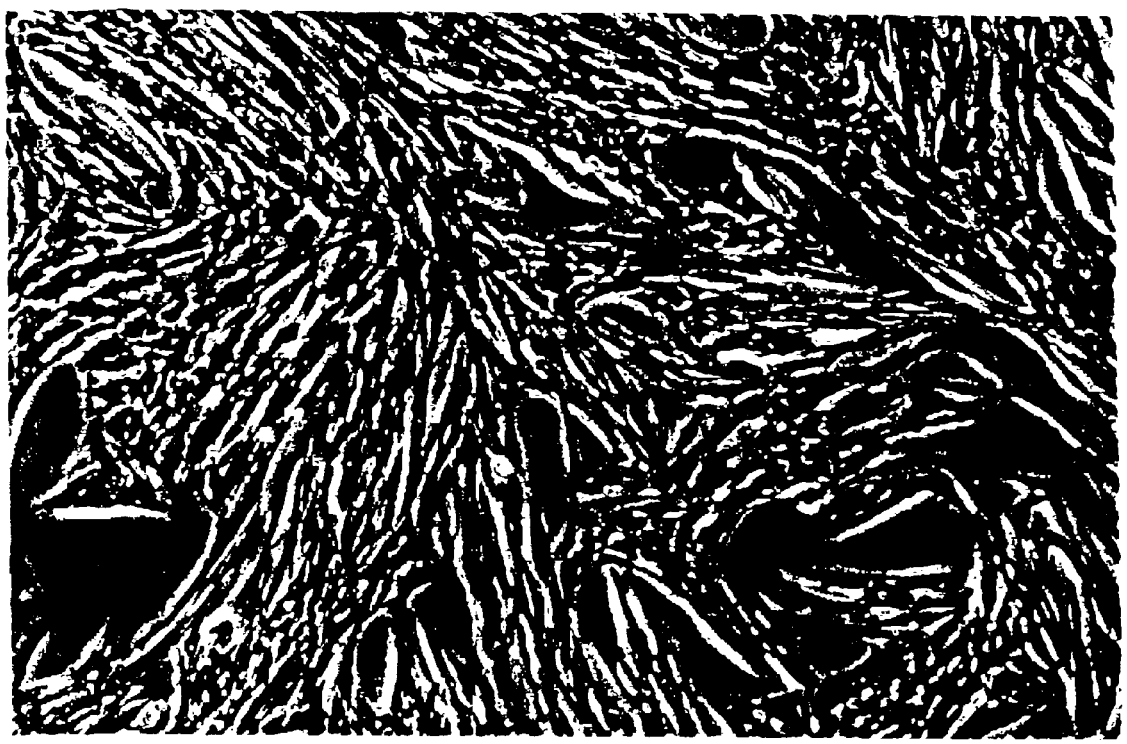
Figure 12A:
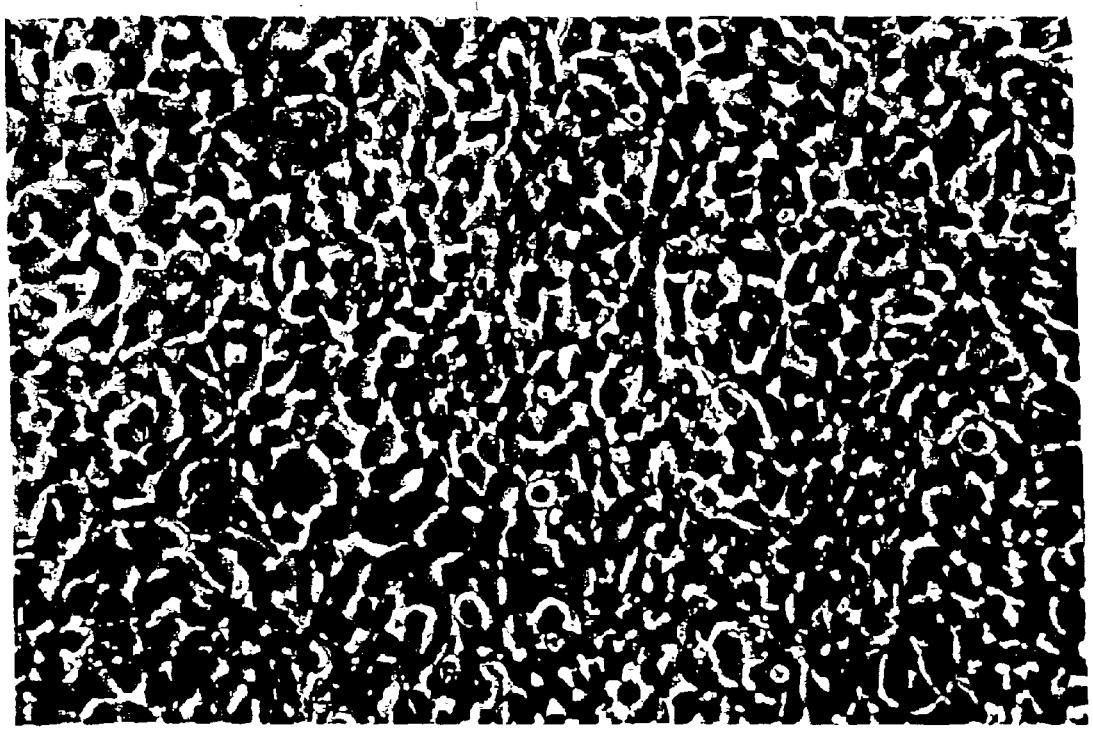
FIGS. 12A, 12B, and 12C show photographs of HeLa cells infected with adeno-LacZ, adeno-p53 and adeno-XAF-1, respectively.
Figure 12B:
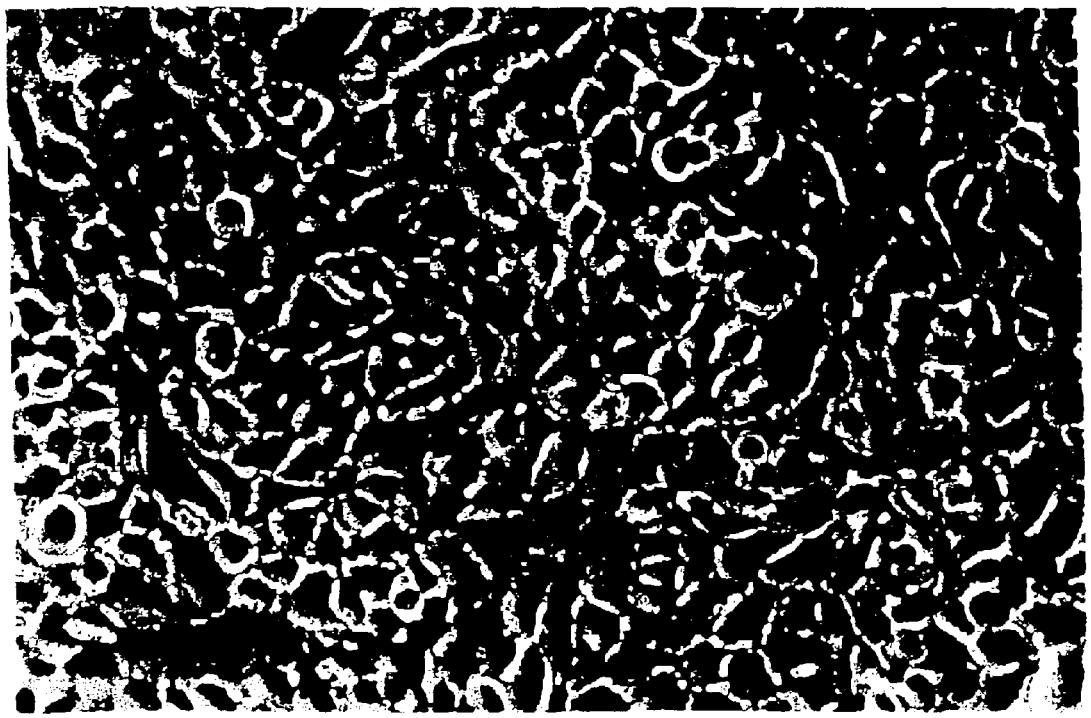
Figure 12C:
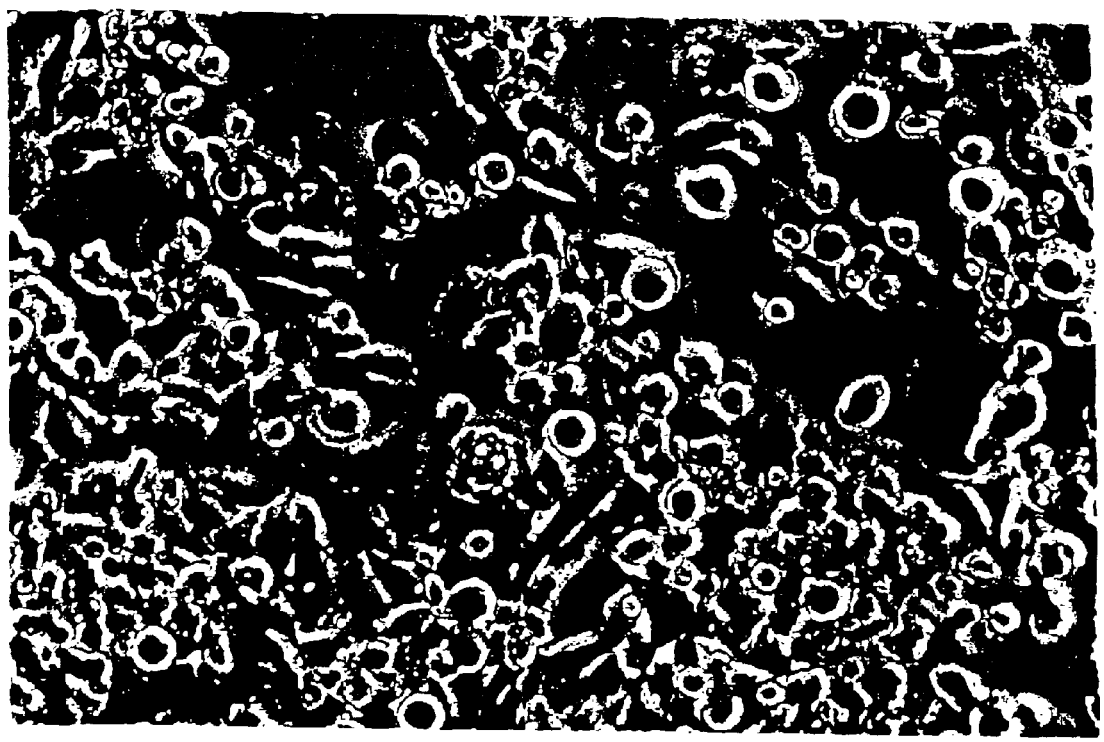

The XAF-1 expressing adenovirus resulted in a similar decrease in the number of viable cells in both HEL and HeLa cell lines. The decrease ill viability in the HeLa cell lines would therefore seem to be p53a independent. Photographs of adeno-LacZ infected, adeno-p53 infected and adeno-XAF-1 infected HEL (FIGS. 11A, 11B, 11C) and HeLa cells (FIGS. 12A, 12B, 12C) are included. The morphology of the XAF-1 overexpressing HEL cells is consistent with cell cycle arrest. In contrast, the XAF-1 overexpressing HeLa cells demonstrate classical features of apoptosis, including pyknotic nuclei and extensive blebbing. Photographs were taken four days post-infection using a standard phase-contrast, inverted tissue culture microscope.

EXAMPLE VIII

Cell Cycle Analysis on XAF-1 Overexpressing HEL and HeLa Cells

Methods $1 \times 10^5$ HeLa or HEL cells were infected at an MOI of 10 with recombinant adenoviruses expressing either LacZ (negative control), p53 (positive control for cell cycle arrest) or XAF-1. Cell were harvested at 96 hours post-infection, rinsed with PBS and fixed with 100% ethanol. Fixed cells were centrifuged 5 min at 1000 RPM, the ethanol removed, and the cells resuspended in 1 ml PBS. 100 µl of 0.1 mg/ml RNAse was added and the cells incubated at 37° C. for 30 minutes. 100 µl of 1 mg/ml propidium iodide was added to stain for DNA content. Cells were then analyzed on a FACS machine and cell cycle effects examined.

Results

Figure 13A:
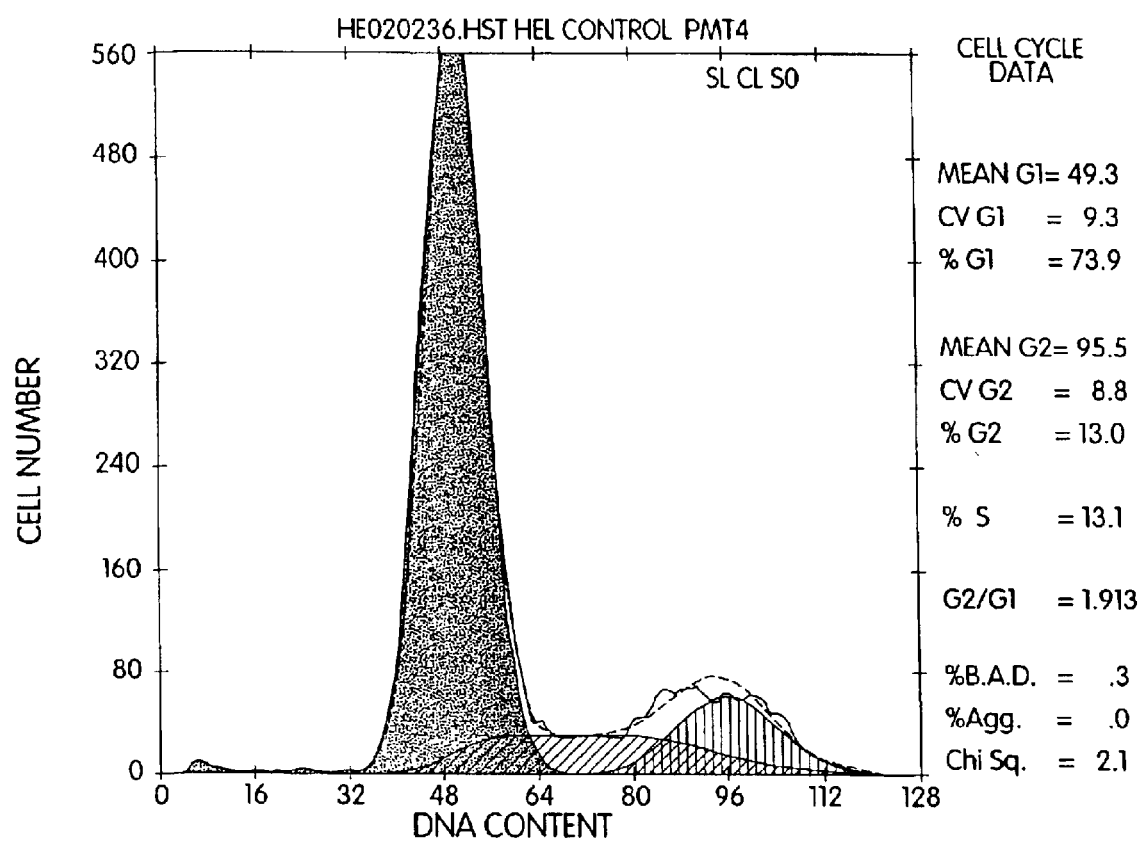
FIGS. 13A, 13B, 13C, and 13D are graphs showing cell cycle profiles of HEL cells transfected with nothing, adeno-LacZ, adeno-p53, and adeno-XAF-1, respectively.
Figure 13B:
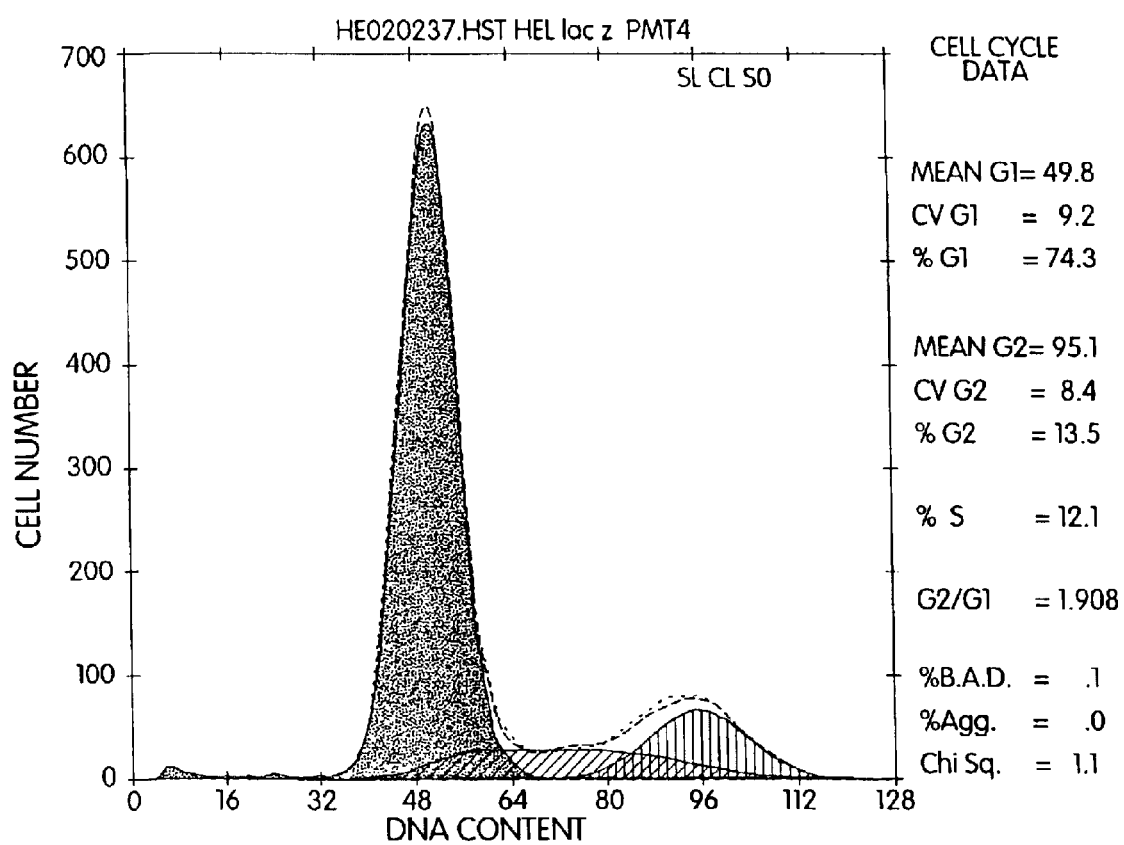
Figure 13C:
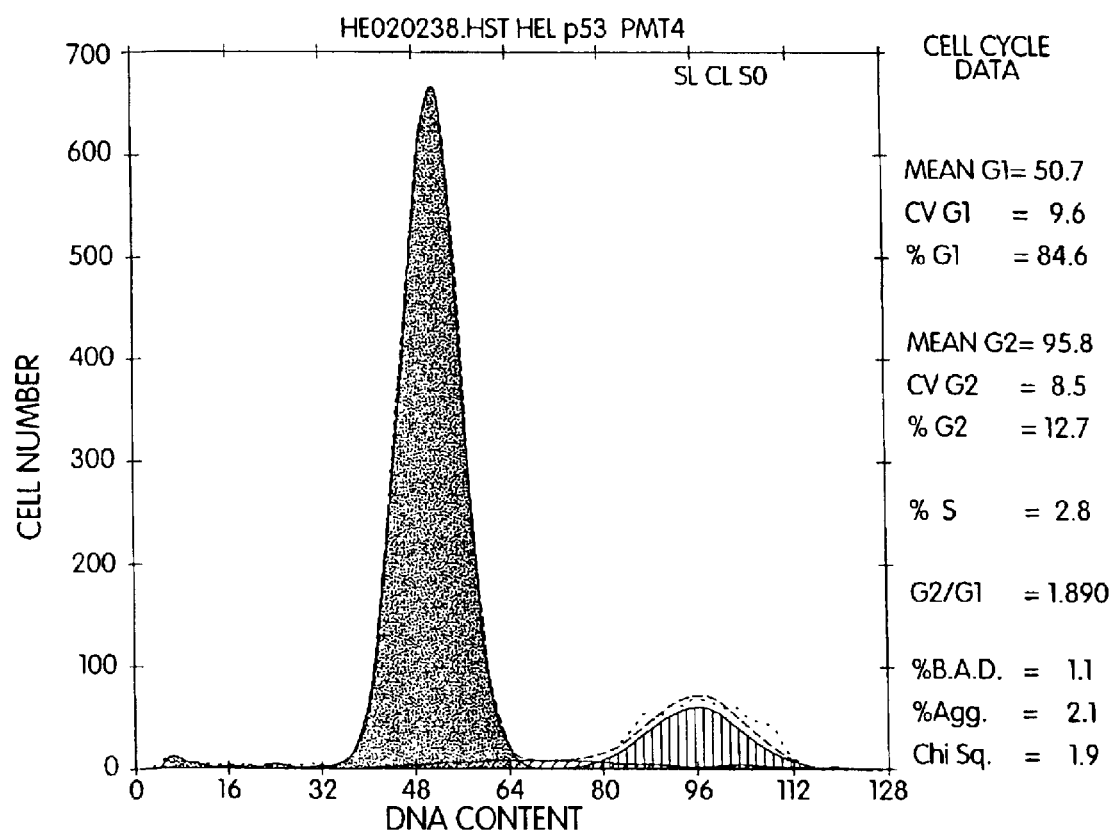
Figure 13D:
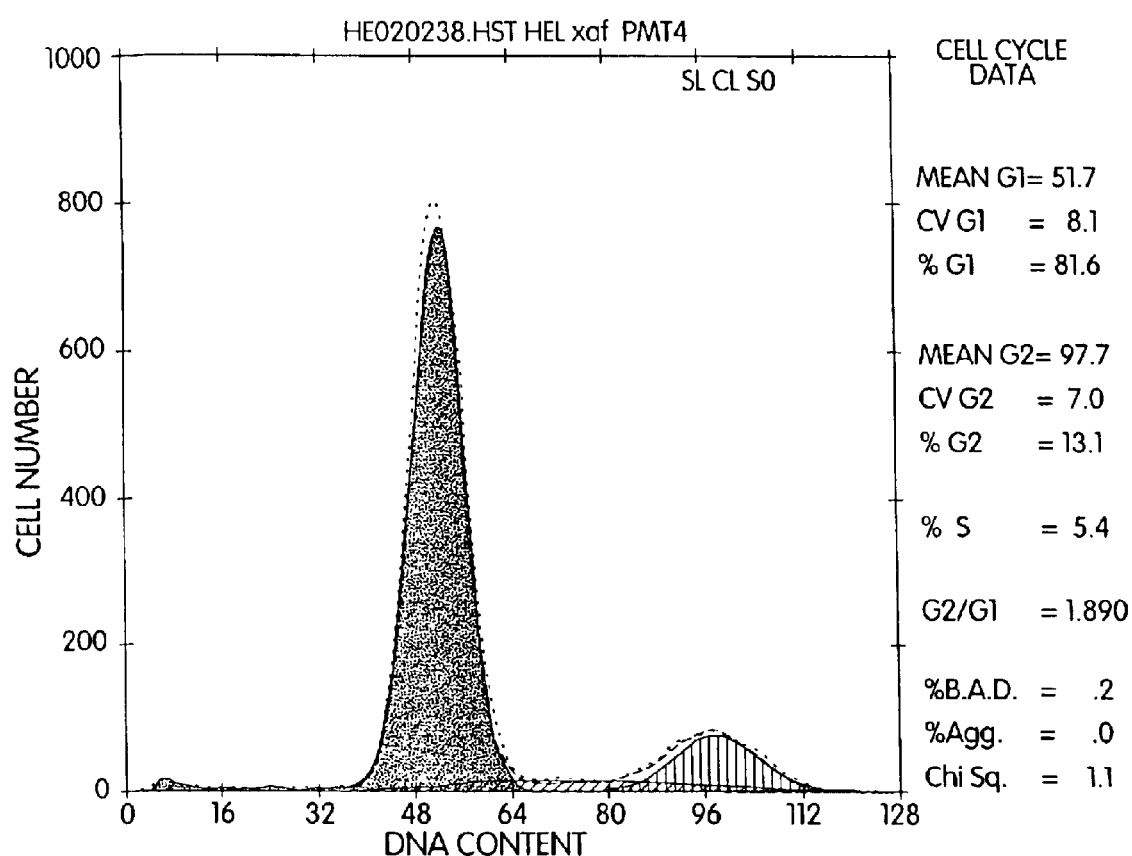
Figure 14A:
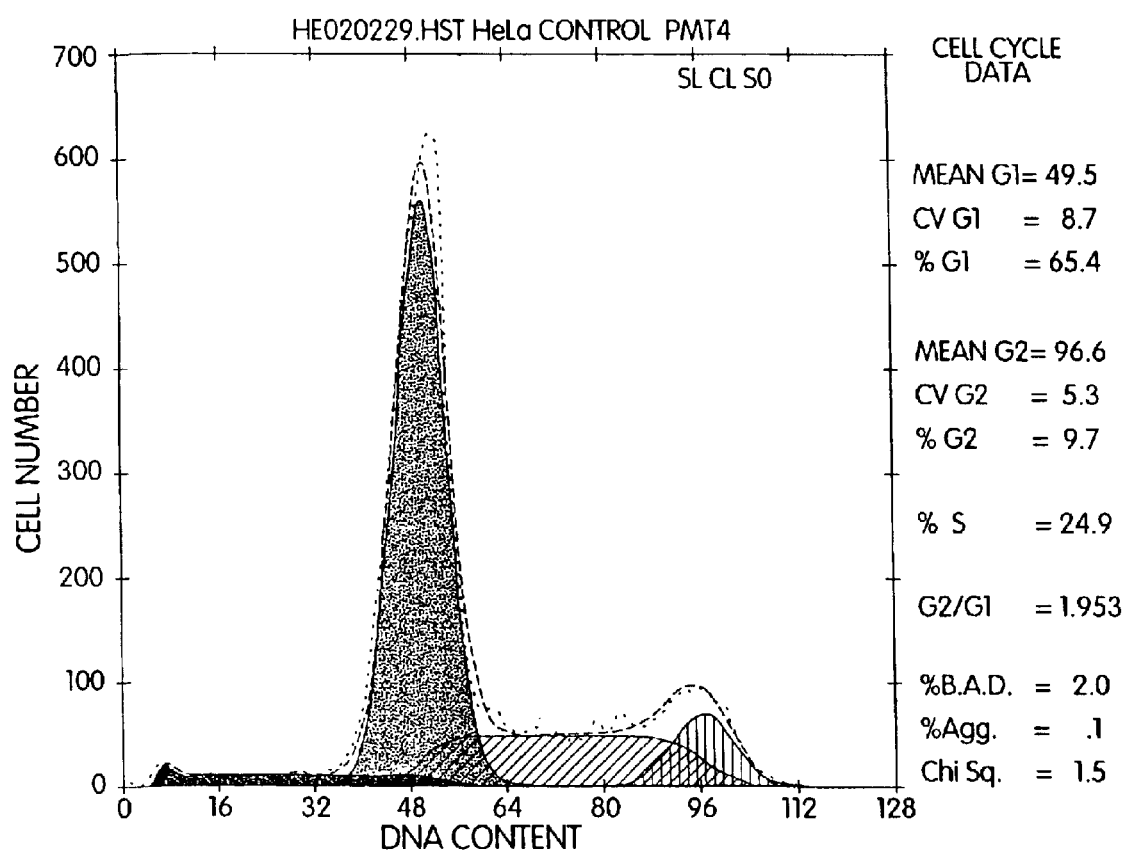
FIGS. 14A, 14B, 14C, and 14D are graphs showing cell cycle profiles of HeLa cells transfected with nothing, adeno-LacZ, adeno-p53, and adeno-XAF-1, respectively.
Figure 14B:
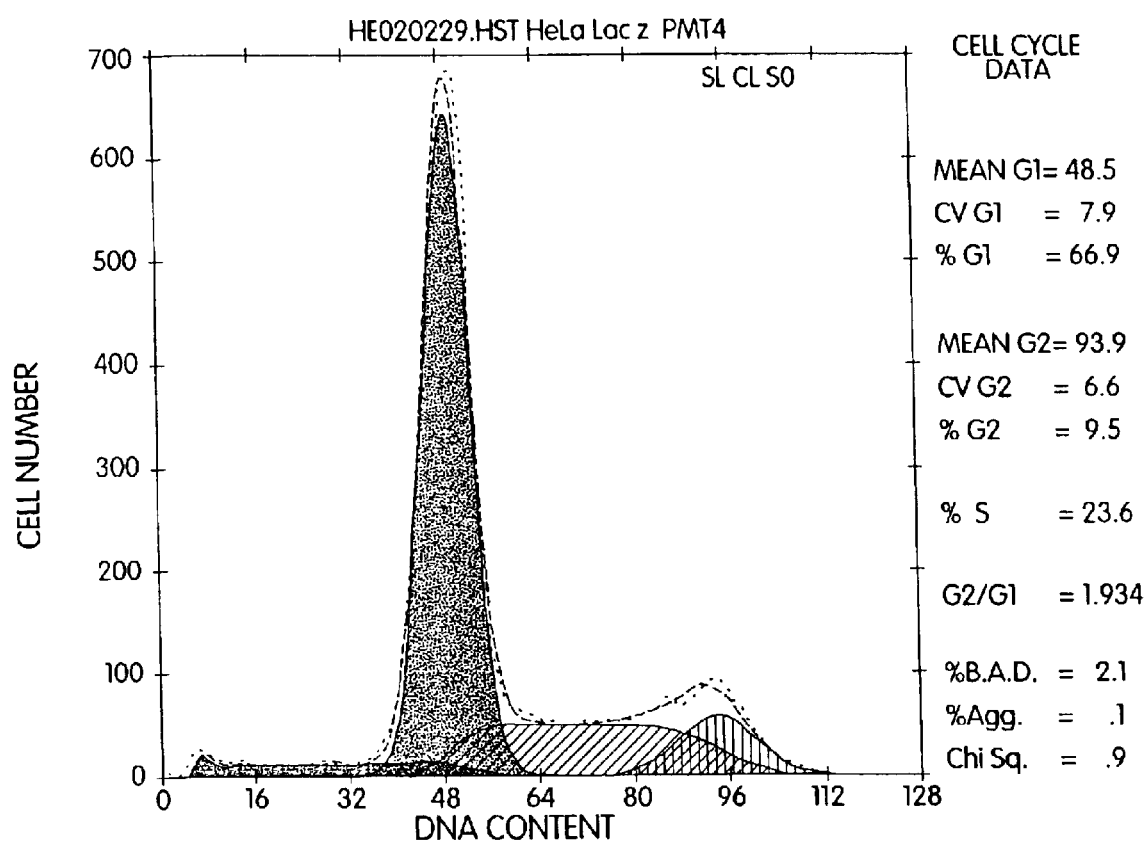
Figure 14C:
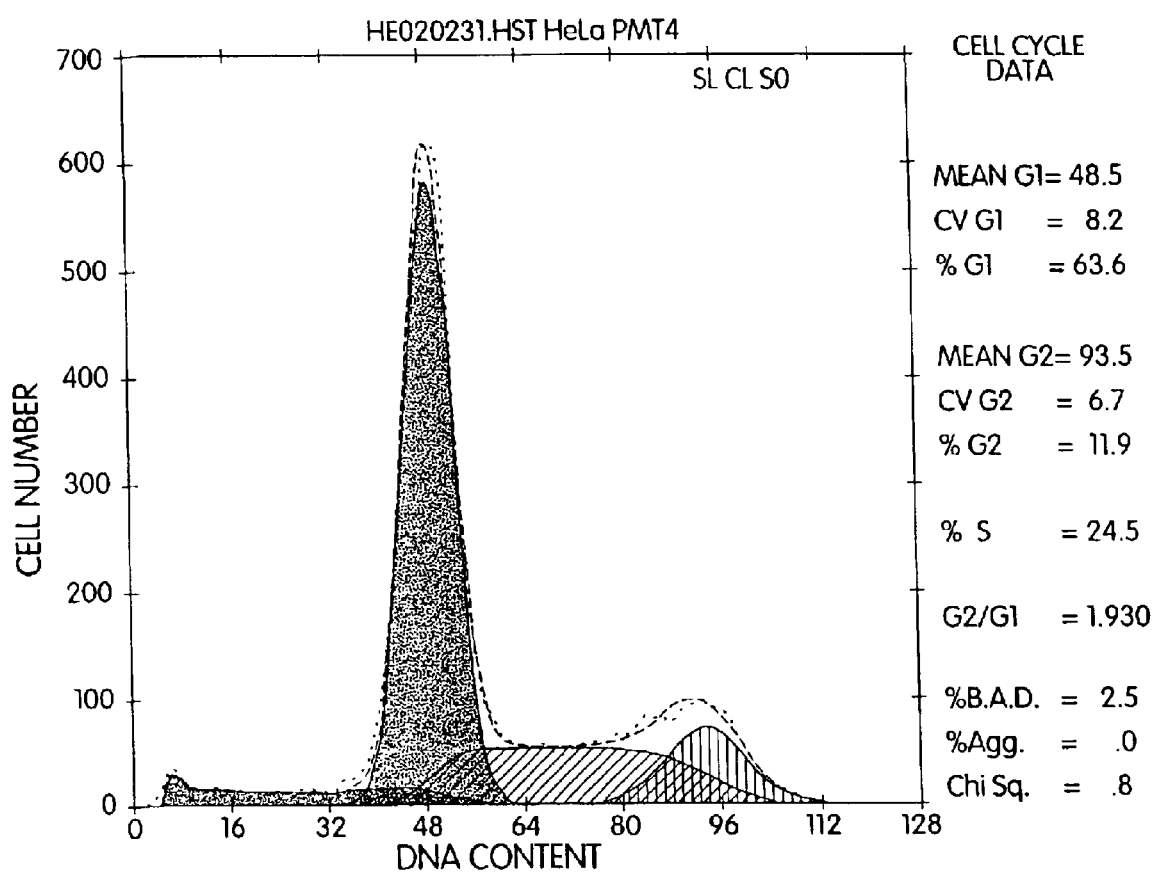
Figure 14D:
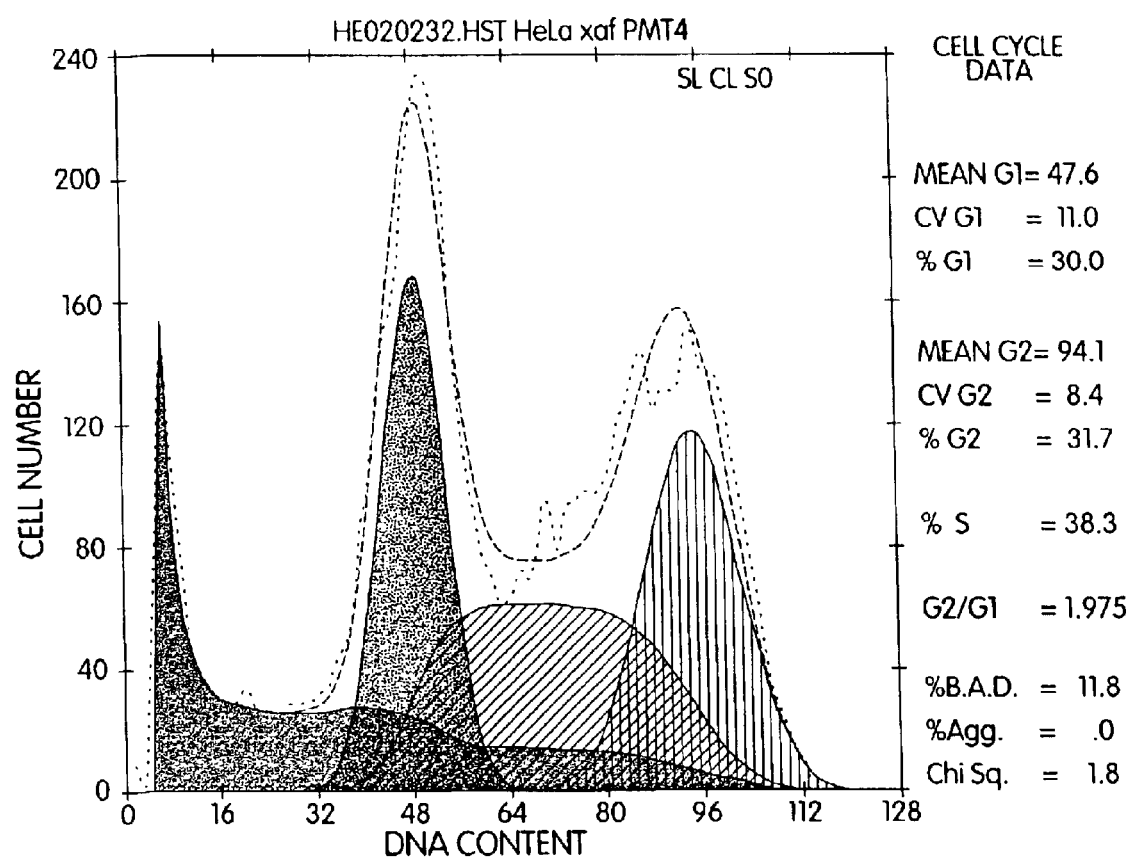

In HEL cells, adeno-LacZ infection had no effect on the cell cycle profiles (compare FIG. 13A [uninfected] with FIG. 13B [LacZ infected]). In contrast, both p53 (FIG. 13C) and XAF-1 (FIG. 13D) expressing adenoviruses caused a virtually complete cessation of cell cycle and a GI arrest (note absence of S phase cells and accumulation of G1 arrested cells). The effects of p53 and XAF-1 were identical. Infection of BeLa cells with the LacZ virus had no effect, as seen in FIGS. 14A and 14B). In contrast to the HEL cells, HeLa cells did not arrest when infected with the adeno-p53 virus (FIG. 14C). With the adeno-XAF-1 virus, HeLa cells did not arrest in G1, but instead underwent apoptosis (FIG. 14C). (Note: the changing scales on the FACS outputs give the impression of a G2 arrest [i.e., cell with 2n DNA]. In fact, the numbers of cells in S and G2 did not change significantly). There is a loss of G1 cells and an increase in the number of cells with less than In DNA content, indicating apoptosis.

EXAMPLE IX

Chromosomal Localization of the XAF-1 Gene by Fluorescent In Situ Hybridization (FISH)

Methods

Figure 15A:
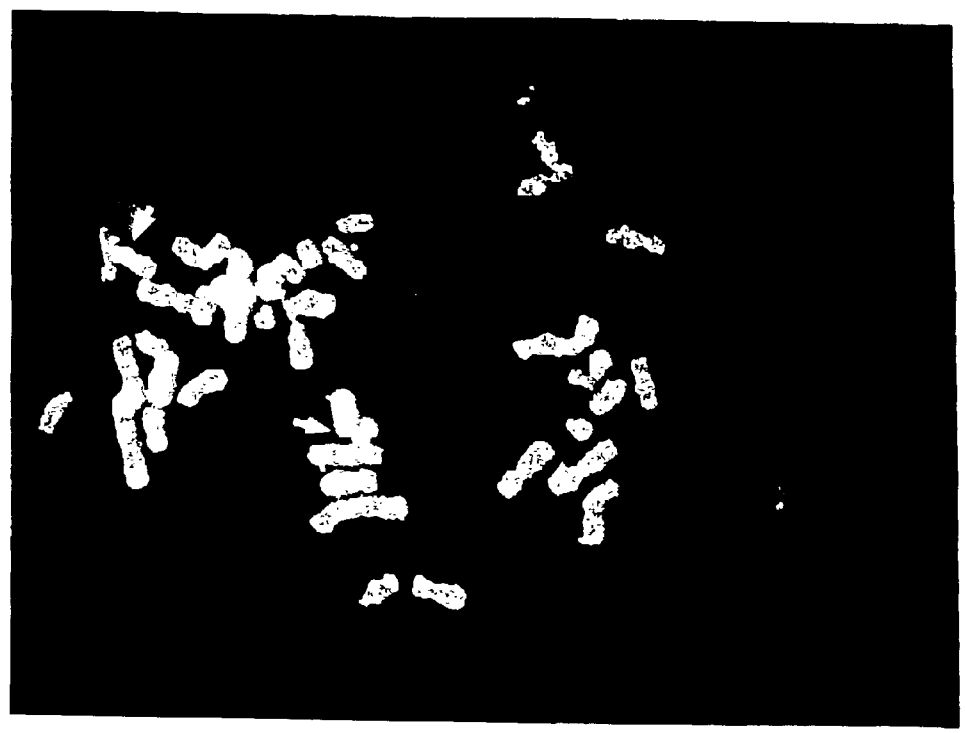
FIGS. 15A and 15B show localization of human XAF-1 by FISH.
Figure 15B:

FISH was performed on freshly isolated mouse spleen lymphocytes cultured in RPMI 1640 media containing 15% fetal calf serum, 3 µg/ml concanavalin A, 10 µg/ml lipopolysaccharide, and 50 nM mercaptoethanol. Lymphocytes were synchronized with 180 µg/ml BrdU for 14 hours followed by 4 hr growth in α-MEM containing 2.5 µg/ml thymidine. Chromosome spreads were prepared on slides using hypotonic lysis, after which the chromosomes were fixed and air dried. 1 µg of DNA probe derived from a XAF-1 specific genomic phage clone was labeled with biotinylated dATP using the BRL BioNick labeling kit at 15° C. for 1 hr (Gibco BRL). Slides were baked at 55° C. for 1 hr, RNAse A treated, and the chromosomes denatured in 70% formamide in 2×SSC for 2 min at 70° C., followed by ethanol dehydration. Probe hybridization to the denatured chromosomes was performed overnight in 50% formamide, 10% dextran sulphate, 1 µg/ml mouse cot I DNA. Slides were washed with 2×SSC/50% formamide followed by 2×SSC at 42° C. Biotin labeled DNA was amplified and detected using fluorescein isothiocyanate conjugated avidin and antiavidin antibodies (FIG. 15A). Chromosomes were counterstained with Giemsa and photographed (FIG. 15B).

Results

The XAF-1 gene was found to map to the extreme end of chromosome 17, in the p13.3 region. This region is known to encode an as yet unidentified tumor suppressor gene(s). This tumor suppressor gene is believed to be involved in a large number of tumor types, including uterine cervical carcinoma (Park et al., Cancer Genet. Cytogenet. 79: 74–78, 1995), breast tumors (Cornelis et al., Cancer Res. 54: 4200–4206, 1994, Merlo et al., Cancer Genet. Cytogenet. 76: 106–111, 1994), gastric carcinoma (Kim et al., Lab. Invest. 72: 232–236, 1995), ovarian epithelial cancer (Wertheim et al., Oncogene 12: 2147–2153, 1996), pediatric medulloblastoma (McDonald et al., Genomics 23: 229–232, 1994, reviewed in Cogan and McDonald, J. of Neuro-Oncology 29: 103–112, 1996) and lung carcinoma (White et al., Br. J. Cancer 74: 863–870, 1996). Thus XAF-1 maybe a tumor suppressor and therapies designed to over-express XAF-1 in cancer cells may be effective (i.e., gene therapy, compounds that up-regulate endogenous XAF-1 or compounds that activate the XAF-1 pathway). Furthermore, the XAF-1 gene may provide an important staging/prognostic indicator in cancer diagnostics through the development of a LOH type assay using PCR based detection of microsatellites in the XAF-1 locus.

EXAMPLE X

Sub-Cellular Localization of the XAF-1 Protein

Methods

Triplicate plates of HeLa cells (ATCC, Bethesda, Md.) were infected with a recombinant adenovirus expressing the XAF-1 open reading frame under the control of the chicken β-actin promoter at a multiplicity of infection 10. At 48 hrs post infection, the cells were harvested in 5 ml of phosphate buffered saline, pelleted by low speed centrifugation (5 min, 1000 rpm in a Beckman JA-10 rotor at 4° C.), and cell extracts prepared as follows:

- cells were washed with isotonic Tris buffered saline (pH 7.0)
- cells were lysed by freeze/thawing 5 times in Cell Extraction Buffer (50 mM PIPES, 50 mM KCl, 5 mM EGTA, 2 mM $MgCl_2$, 1 mM DTT, and 20 µM cytochalasin B)
- nuclei were pelleted by centrifugation at 5000 RPM in a JA-17 rotor for 5 minutes. Nuclear pellet was resuspended in isotonic Tris pH 7.0, and frozen at −80° C.
- cytoplasmic extract was further processed by centrifugation at 60,000 RPM in a TA 100.3 rotor for 30 minutes. Supernatant (cytoplasmic extract) was frozen at −80° C. Pelleted material (membrane fraction) was resuspended in isotonic Tris pH 7.0, and frozen.
- nuclear, membrane, and cytoplasmic fractions were electrophoresed on a 12.5% SDS polyacrylamide gel, and electroblotted onto PVDF membranes.

Western blotting was first performed using rabbit polyclonal anti-XAF-1 antibody at a concentration of 1:1,500 in Tris buffered saline containing 0.5% NP-40and 3% skim milk powder. The secondary antibody was a horse radish peroxidase coupled goat anti-rabbit IgG (Amersham) used at 1:2000 dilution in the same buffer system. Chemiluminescent detection of bound antibody was performed using Amersham's ECL kit according to the manufacturer's directions. The membrane was then re-probed with polyclonal anti-XIAP antibody at 1:2000 dilution and processed as above.

Results

Figure 16A:
FIGS. 16A and 16B show subcellular localization of the XAF-1 protein.
Figure 16B:
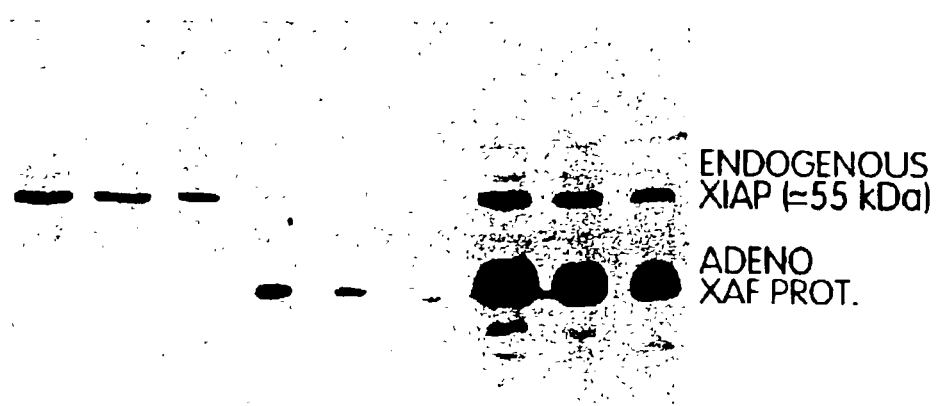

FIG. 16A demonstrates that the vast majority of the adenovirus expressed XAF-1 protein fractionates in the nuclear compartment. A very small fraction of the protein was observed in the membrane fraction, likely as a result of incomplete separation of the nuclear and membrane fractions. None of the protein was observed in the cytoplasmic fraction. FIG. 16B demonstrates that overexpression of the XAF-1 protein resulted in a re-distribution of >½ of the endogenous XIAP protein from the cytoplasmic fraction to the nuclear fraction. One explanation for this is that the function of XAF-1 is to relocate the XIAP protein to its 'real' site of action, in the nucleus. Alternatively, XIAP may be interfering with the function of XAF-1 in the nucleus.

EXAMPLE XI

XAF-1 Protein is Found in the Nucleus by GFP Staining

Methods

An expression vector called pGFP-XAF-1 was constructed that generates a fusion protein between green fluorescent protein (GFP) and XAF-1 (Clontech). The coding region of GFP was fused to the amino terminus of the full length XAF-1 coding region.

CHO-K1 cells or 3Y1 primary rat embryo fibroblast cells from Fischer rat fetus (available from the Riken gene bank, Tsukuba, Japan) were transiently transfected by standard lipofection methods using the Trans-IT lipofection reagent commercially available from Mirus with pGFP or pGFP-XAF-1. 24 hours following transfection, the cells were visualized on a fluorescent microscope with a blue filter.

All cells were counter stained with evans blue.

Results

Figure 17A:
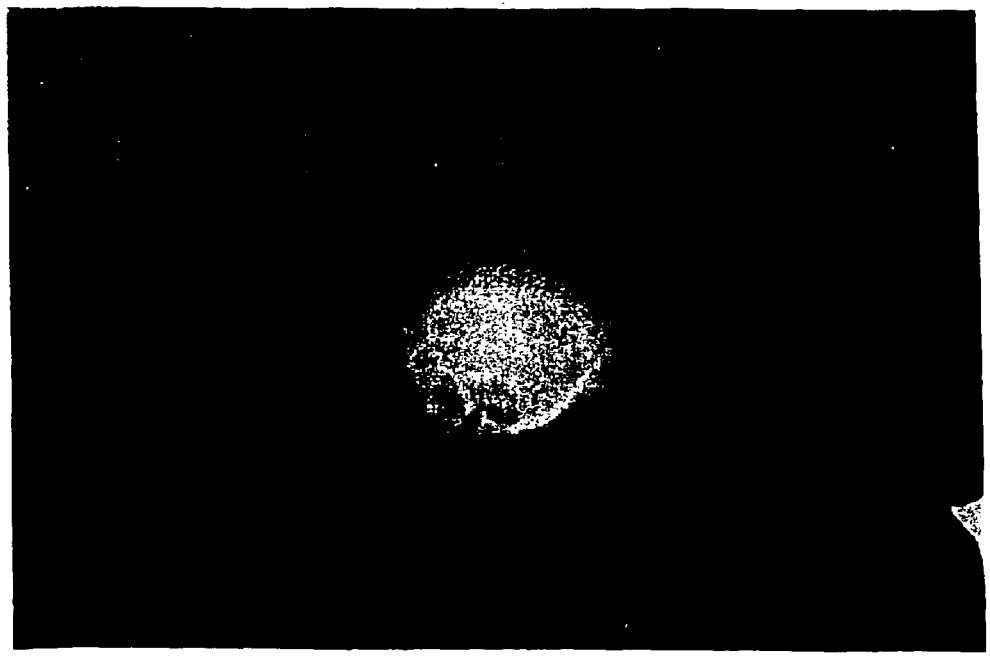
FIGS. 17A, 17B, and 17C are photographs of CHO-K1 cells expressing green fluorescent protein (GFP)-labeled XAF-1 visualized with a fluorescent microscope.
Figure 17B:
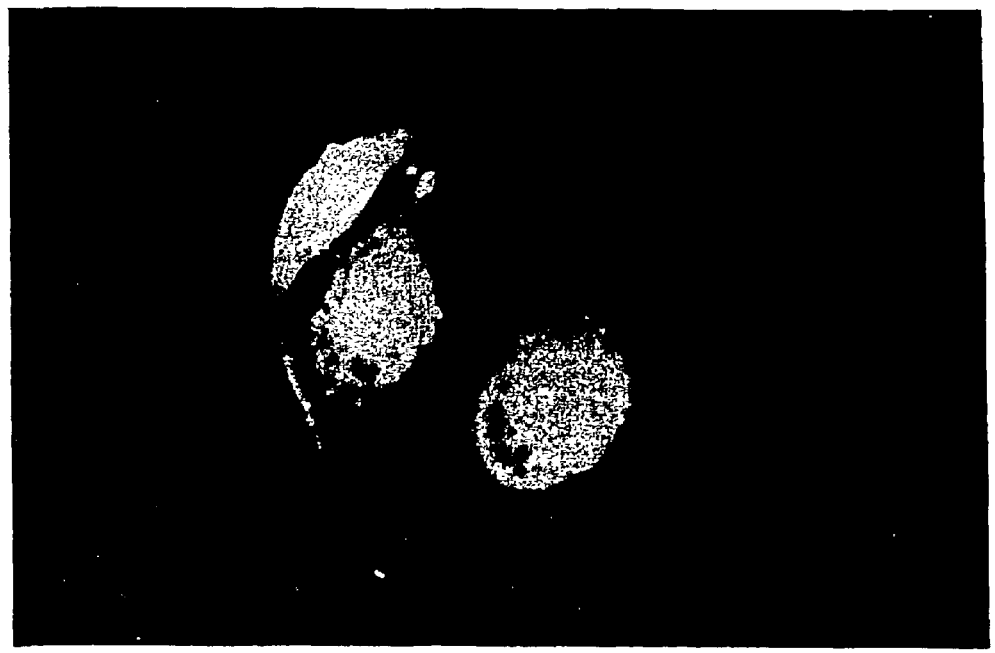
Figure 17C:

FIGS. 17A, 17B, and 17C are photographs of transfected CHO-K1 cells. FIGS. 17A and 17B shows that in CHO-K1 cells transiently transfected with pGFP-XAF-1, the GFP-labeled XAF-1 protein was localized to the nucleus. This is in contrast to the GFP homogenously distributed throughout the cytoplasm and nucleus in the CHO-K1 cells transiently transfected with pGFP shown on FIG. 17C.

Figure 18A:
FIGS. 18A and 18B are photographs of 3Y1 cells expressing GFP visualized with a fluorescent microscope.
Figure 18B:

FIGS. 18A and 18B shows the GFP homogenously distributed throughout the cytoplasm and nucleus in 3Y1 cells transiently transfected with pGFP.

Figure 19A:
FIGS. 19A and 19B are photographs of 3Y1 cells expressing GFP-labeled XAF-1 visualized with a fluorescent microscope.
Figure 19B:

FIGS. 19A and 19B shows the GFP-labeled XAF-1 protein localized to the nucleus in 3Y1 cells transiently transfected with pGFP-XAF-1.

We have furthermore found that XAF-1 expression resulted in a re-distribution of XIAP protein from the cytoplasm to the nucleus.

EXAMPLE XII

Neither XAF-1 nor Mammalian IAPs Over-Expression can Induce NF-κB Activation in 293 T Cells The members of the growing family of TRAF proteins each possesses an amino terminal RING zinc finger and/or additional zinc fingers, a leucine zipper, and a unique, conserved carboxy terminal coiled coil motif, the TRAF-C domain, which defines the family. TRAF1 and TRAF2 were first identified as components of the TNF-R2 signaling complex (Rothe et al., Cell 78: 681–692, 1994). The interaction of the TRAF proteins are complex, reflecting their putative role as adapter molecules that exhibit no apparent enzymatic activity themselves.

Methods

Mammalian expression vectors encoding XAF-1, HIAP-1, HIAP-2, XIAP, TRAF1, TRAF2, TRAF3, TRAF4, TRAF5, TRAF6, RIP, and TRADD were constructed by insertion of each coding region into the pcDNA3-myc expression vector which contains an N-terminal c-myc epitope sequence (similar vectors are commercially available from Invitrogen). The NF-κB firefly luciferase reporter plasmid pELAM-Lu was constructed by insertion of PCR-amplified E-selectin promoter sequences from position −730 to position 52 into the pGL3-Basic vector which is commercially available from Promega.

293T cells were seeded into collagen-coated six-well plates at $2\times10^5$ cells per well 24 hrs before transfection. Cells were then transfected with 0.5 µg of pELAM-Lu reporter plasmid, 0.05 µg of pRL-CMV, 1 µg of indicated expression plasmid and enough pCMV-myc control plasmid to give 4 µg of total DNA by standard lipofection methods using Trans-IT lipofection reagent commercially available from Mirus. Twenty-four hours after transfection, cells were washed with PBS and lysed in 400 µl of Passive Lysis Buffer commercially available from Promega. Lysate (20 µl) from each samples was used to measure firefly luciferase activity. Firefly luciferase activity was determined and normalized on the basis of Renilla luciferase expression level. Luciferase activity was measured in a model TD20/20 luminometer using the Dual luciferase assay system according to the manufacture's protocol (Promega).

Values shown are averages for an experiment in which each transfection was performed in duplicate.

Results

Figure 20:
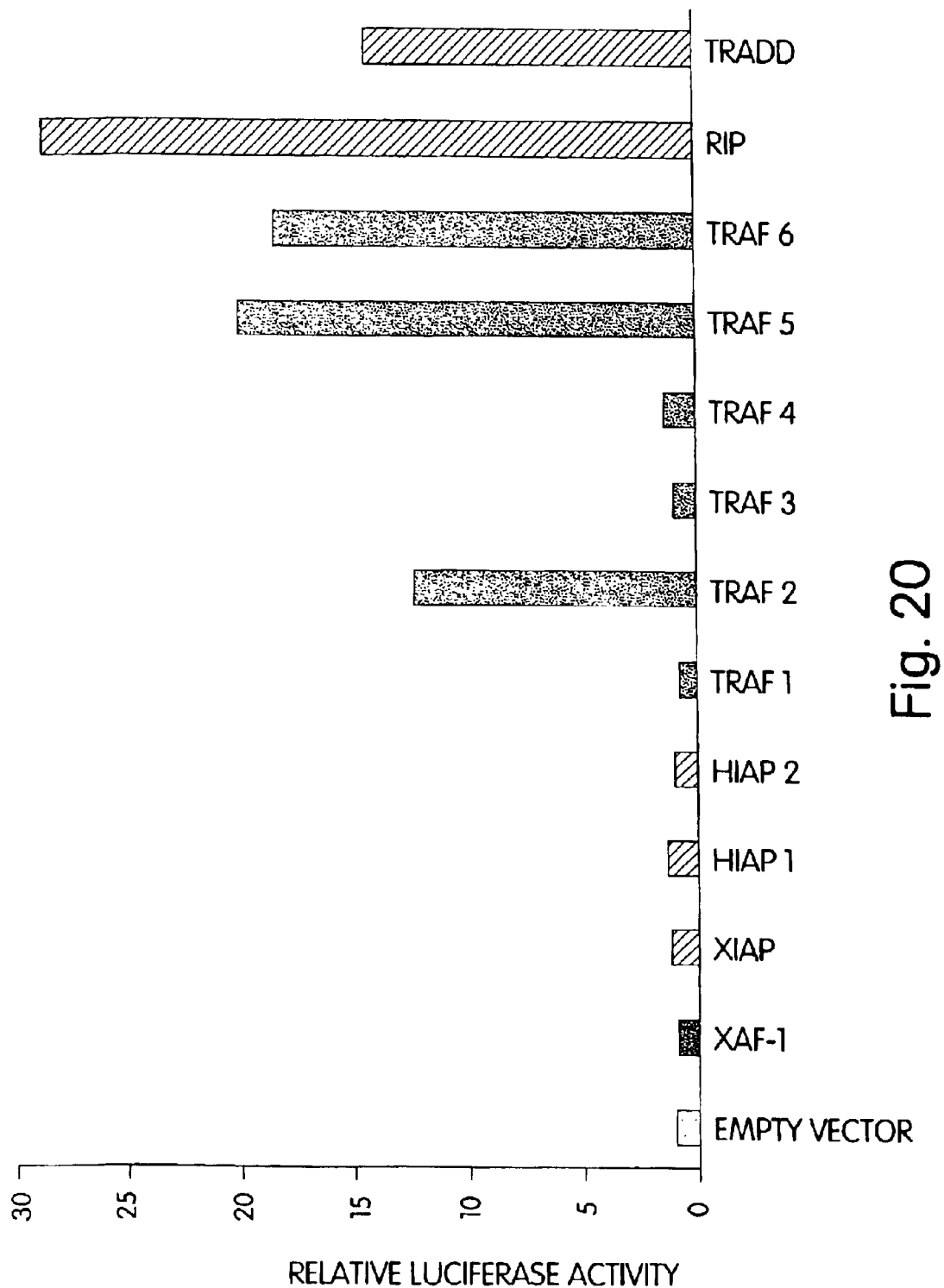
FIG. 20 is a graph of relative luciferase activity induced by NF-κB activation by expression of indicated proteins.

XAF-1, HIAP-1, HIAP-2, and XIAP do not induced NF-κB activation in 293 T cells. As shown in FIG. 20, when expressed singly in 293T cells, none of the IAPs or XAF-1 resulted in measurable activation of NF-κB, as measured by luciferase activity. TRAF2, TRAF5, TRAF6, RIP, and TRADD expression plasmids, however, all strongly transactivated the reporter gene. TRAF1, TRAF3, and TRAF4 failed to transactivate the reporter.

We have also obtained data showing that XIAP can activate NF-κB in HeLa cells.

EXAMPLE XIII

Co-Expression of XAF-1 and Mammalian IAPs do not Induce NF-κB Activation in 293 T Cells Methods 293T cells were seeded into collagen-coated six-well plates at $2\times10^5$ cells per well 24 hrs before transfection. Cells were then transfected with 0.5 µg of pELAM-Lu reporter plasmid, 0.05 µg of pRL-CMV, 4 µg of indicated expression plasmid(s) and enough pCMV-myc control plasmid to give 5 µg of total DNA by standard lipofection methods using Trans-IT lipofection reagent commercially available from Mirus. Twenty-four hours after transfection, cells were washed with PBS and lysed in 400 µl of Passive Lysis Buffer commercially available from Promega. Lysate (20 µl) from each samples was used to measure firefly luciferase activity. Firefly luciferase activity was determined and normalized on the basis of Renilla luciferase expression level. Luciferase activity was measured in a model TD20/20 luminometer using the Dual luciferase assay system according to the manufacture's protocol (Promega). Values shown are averages for an experiment in which each transfection was performed in duplicate.

Results

Figure 21:
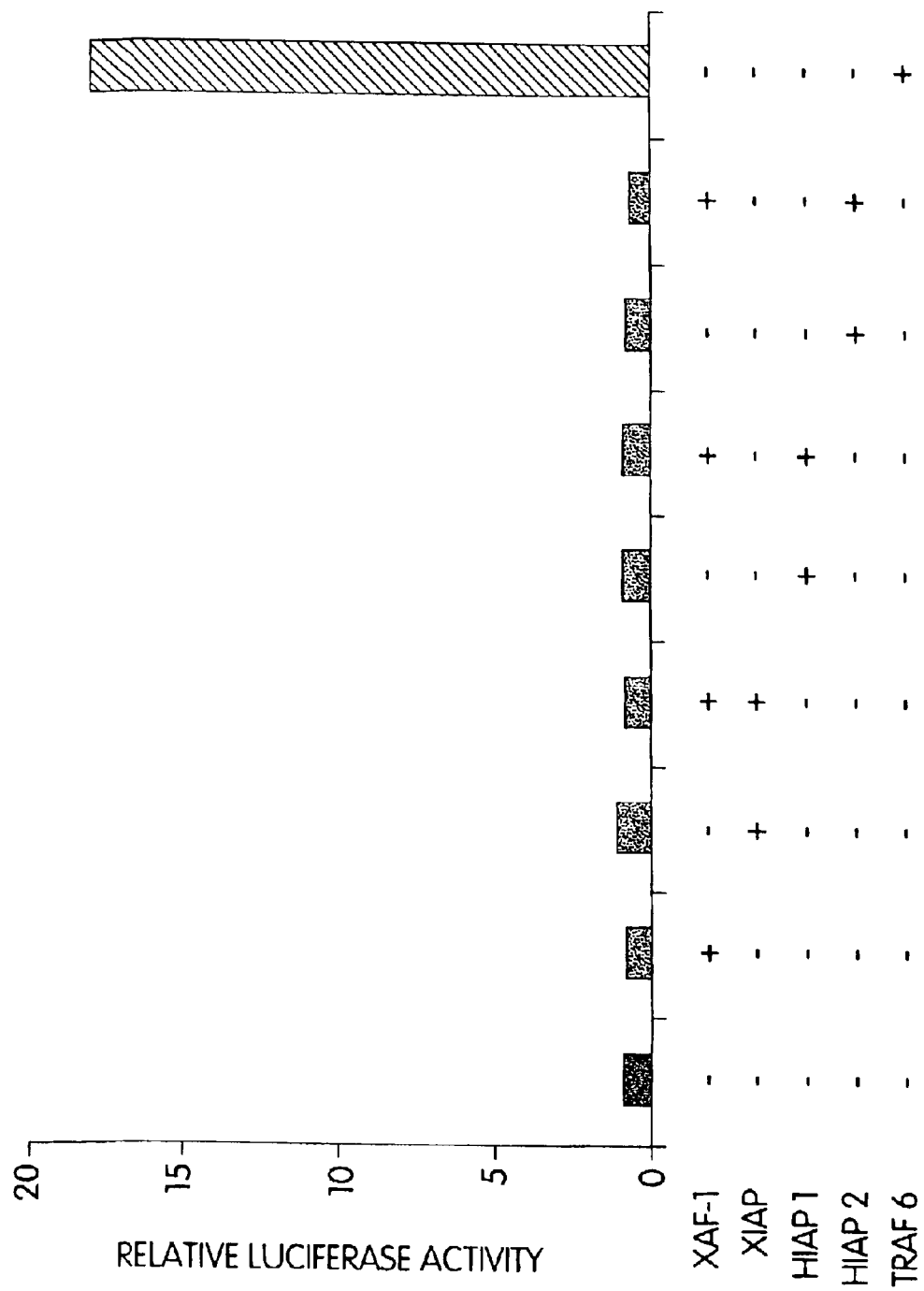
FIG. 21 is a graph of relative luciferase activity induced by NF-κB activation by co-expression of indicated proteins.

As shown in FIG. 21, none of the IAPs, alone, or in combination with XAF-1, resulted in measurable activation of NF-κB when expressed in 293T cells. Expression of TRAF6, shown here as a positive control, did induce NF-κB activation.

EXAMPLE XIV

Dose Response Effect of XAF-1 Expression on TRAF6-Mediated NF-κB Activation

Methods 293T cells were seeded into collagen-coated six-well plates at $2 \times 10^5$ cells per well 24 hrs before transfection. Cells were then transfected with 0.5 µg of pELAM-Lu reporter plasmid, 0.1 µg of pRL-CMV, 0.5 µg of pCMV-TRAF6, indicated amounts of pCMV-XAF-1 and enough pCMV-myc control plasmid to give 4 µg of total DNA by standard lipofection methods using Trans-IT lipofection reagent commercially available from Mirus. Twenty-four hours after transfection, cells were washed with PBS and lysed in 400 µl of Passive Lysis Buffer commercially available from Promega. Lysate (20 µl) from each samples was used to measure firefly luciferase activity. Firefly luciferase activity was determined and normalized on the basis of Renilla luciferase expression level. Luciferase activity was measured in a model TD20/20 luminometer using the Dual luciferase assay system according to the manufacture's protocol (Promega). Values shown are averages for an experiment in which each transfection was performed in duplicate.

Results

Figure 22:
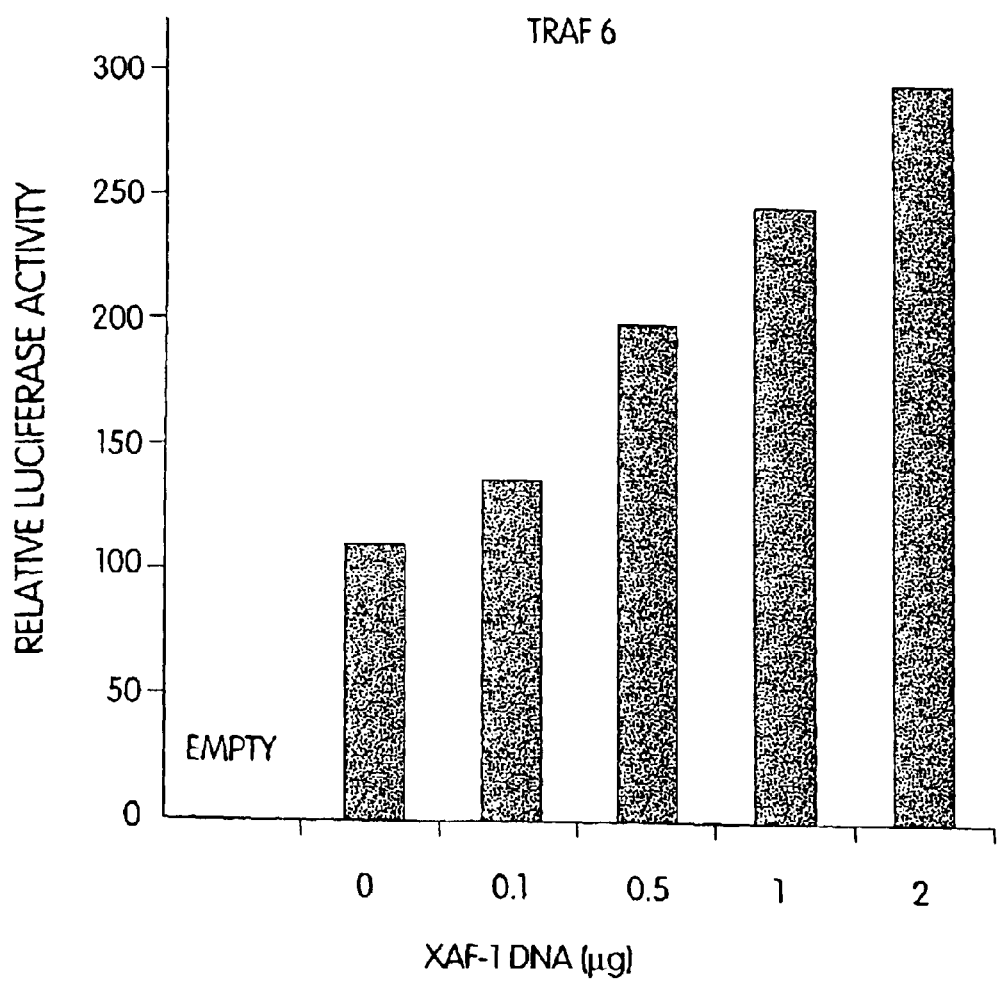
FIG. 22 is a graph of relative luciferase activity induced by NF-κB activation by TRAF6 co-expressed with indicated amounts of XAF-1 protein.

As the results shown in FIG. 22 demonstrate, although expression of TRAF6 was by itself capable of inducing NF-κB activity, co-expression of TRAF6 with XAF-1 resulted in an increased level of NF-κB activation which increased as the amount of XAF-1 expression increased. Hence, XAF-1 was able to enhance the NF-κB inducing abilities of TRAF6.

EXAMPLE XV

Dose Response Effect of XIAP Expression on TRAF6-Mediated NF-κB Activation

Methods 293T cells were seeded into collagen-coated six-well plates at $2 \times 10^5$ cells per well 24 hrs before transfection. Cells were then transfected with 0.5 µg of pELAM-Lu reporter plasmid, 0.1 µg of pRL-CMV, 0.5 µg of pCMV-TRAF6, indicated amounts of pCMV-XIAP and enough pCMV-myc control plasmid to give 4 µg of total DNA by standard lipofection methods using Trans-IT lipofection reagent commercially available from Mirus. Twenty-four hours after transfection, cells were washed with PBS and lysed in 400 µl of Passive Lysis Buffer commercially available from Promega. Lysate (20 µl) from each sample was used to measure firefly luciferase activity. Firefly luciferase activity was determined and normalized on the basis of Renilla luciferase expression level. Luciferase activity was measured in a model TD20/20 luminometer using the Dual luciferase assay system according to the manufacture's protocol (Promega). Values shown are averages for an experiment in which each transfection was performed in duplicate.

Results

Figure 23:
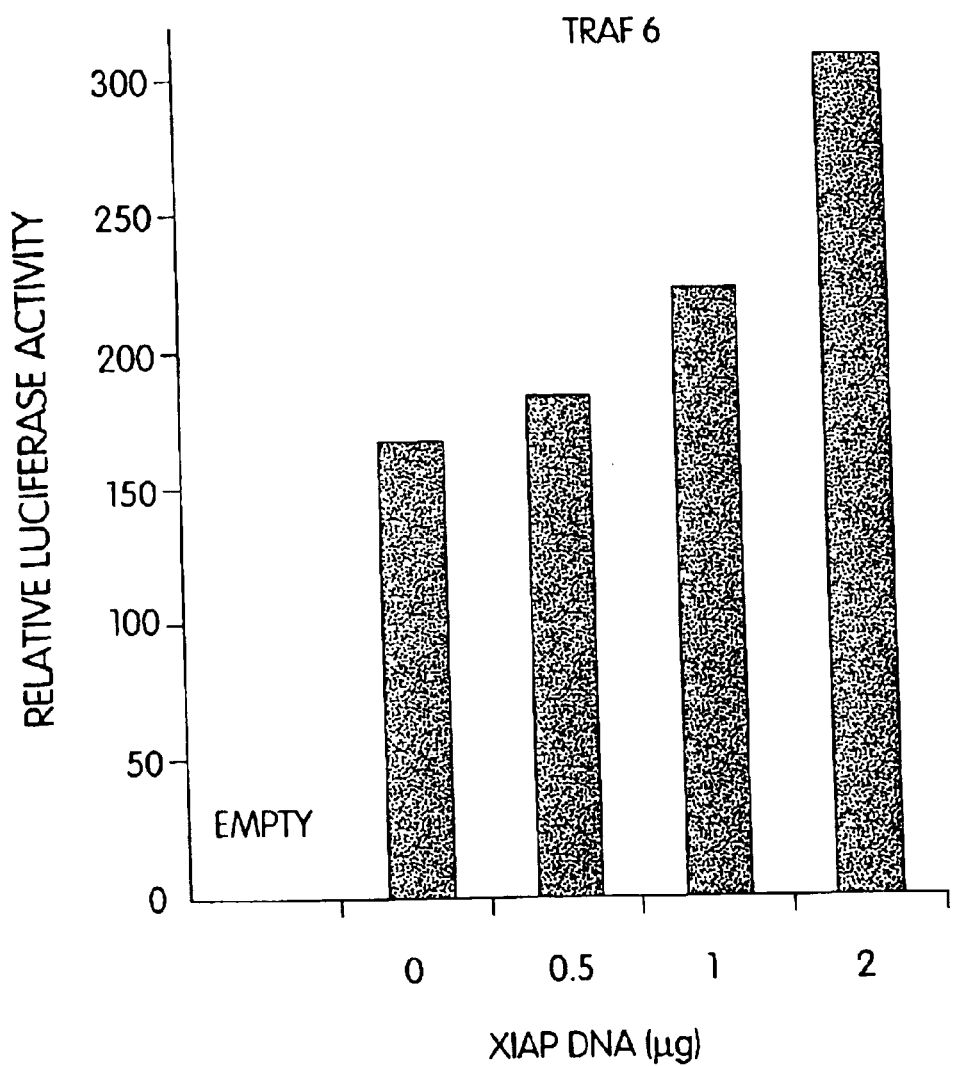
FIG. 23 is a graph of relative luciferase activity induced by NF-κB activation by TRAF6 co-expressed with indicated amounts of XIAP protein.

The results shown in FIG. 23 demonstrate that although expression of TRAF6 was by itself capable of inducing NF-κB activity, co-expression of TRAF6 with XIAP resulted in an increased level of NF-κB activation which increased as the amount of XIAP expression increased. Hence, XIAP was able to enhance the NF-κB inducing abilities of TRAF6.

EXAMPLE XVI

Synergistic Effect of XAF-1 and XIAP Expression on TRAF6- and TRAF2-Mediated NF-κB Activation Methods 293T cells were seeded into collagen-coated six-well plates at $2 \times 10^5$ cells per well 24 hrs before transfection. Cells were then transfected with 0.5 µg of pELAM-Lu (pGL3-E-selectin promoter) and 0.05 µg of pRL-CMV, 1 µg of pCMV-TRAF6 or 1 µg of pCMV-TRAF2, 1 µg of pCMV-XAF-1 and/or pCMV-XIAP, and enough pCMV-myc control plasmid to give 4 µg of total DNA by standard lipofection methods using Trans-IT lipofection reagent (Mirus). Twenty-four hours after transfection, cells were washed with PBS and lysed in 400 µl of Passive Lysis Buffer (Promega). Lysate (20 µl) from each samples was used to measure firefly luciferase, activity. Firefly luciferase activity was determined and normalized on the basis of Renilla luciferase expression level. Luciferase activity was measured in a model TD20/20 luminometer (Promega) using Dual luciferase assay system according to the manufacture's protocol (Promega). Values shown are averages for an experiment in which each transfection was performed in duplicate.

Results

Figure 24:
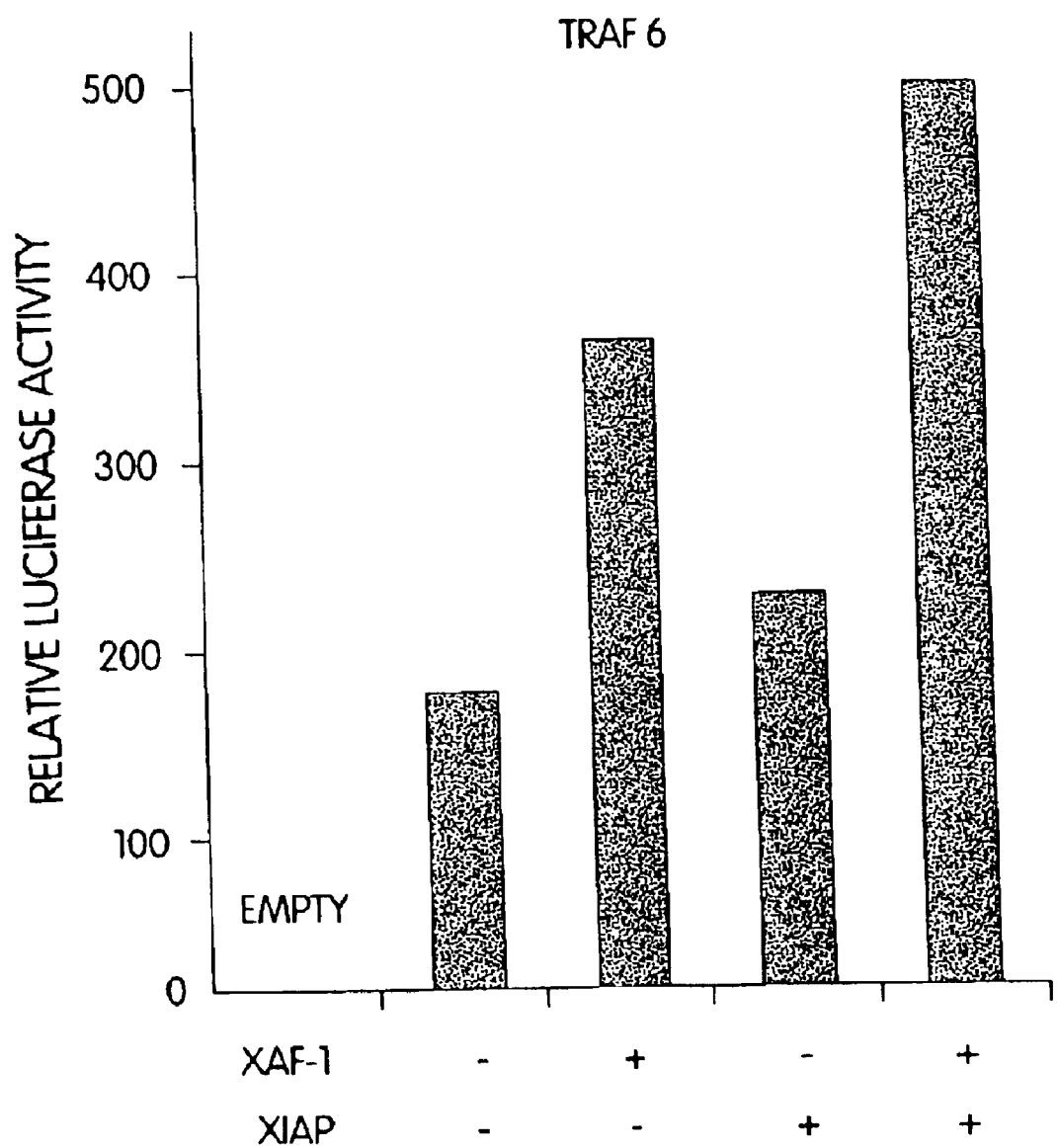
FIG. 24 is a graph of relative luciferase activity induced by NF-κB activation by TRAF6 co-expressed with XIAP and XAF-1 proteins.
Figure 25:
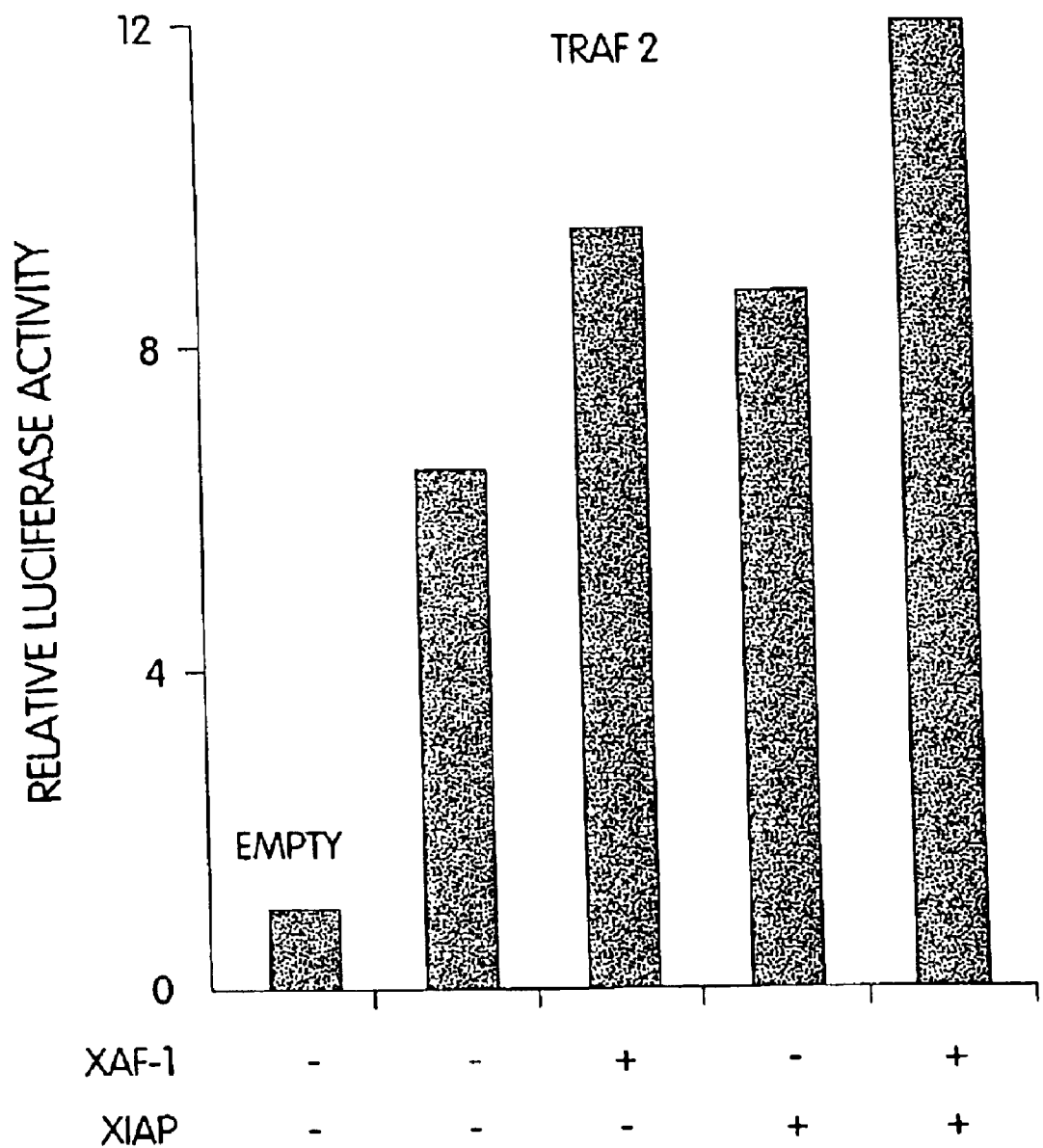
FIG. 25 is a graph of relative luciferase activity induced by NF-κB activation by TRAF2 co-expressed with XIAP and XAF-1 proteins.

XIAP and XAF-1 were additive in their effects on TRAF6 mediated NF-κB transactivation, as shown on FIG. 24. FIG. 25 indicates that XIAP and XAF-1 were also able to assist in TRAF2 mediated NF-κB transactivation, although to a lesser extent than their assistance in TRAF6 mediated NF-κB transactivation. Hence, XIAP and XAF-1 work synergistically in their signal transducing capabilities.

EXAMPLE XVII

C-Terminus of XAF-1 Enhances TRAF6-Mediated NF-κB Activation

Methods

Expression plasmids that express either the amino terminal domain of XAF-1 containing six potential zinc fingers, including the region with significant homology to TRAF4 and TRAF6 (XAF-1N) or the carboxy terminus containing a single potential zinc finger domain (XAF-1C) were tested for their capacity to augment TRAF6 mediated NF-κB activity 293T cells ($2 \times 10^5$) were transfected with 0.5 µg of pELAM-Lu reporter plasmid, 0.1 µg of pRL-TK commercially available from Promega, 0.5 µg of pCMV-TRAF6, 1 µg of indicated expression plasmid and enough pCMV-myc control plasmid to give 4 µg of total DNA. Firefly luciferase activity were determined 24 hrs after transfection and normalized on the basis of Renilla luciferase expression level. Values shown are averages for an experiment in which each transfection was performed in duplicate.

Results

Figure 26:
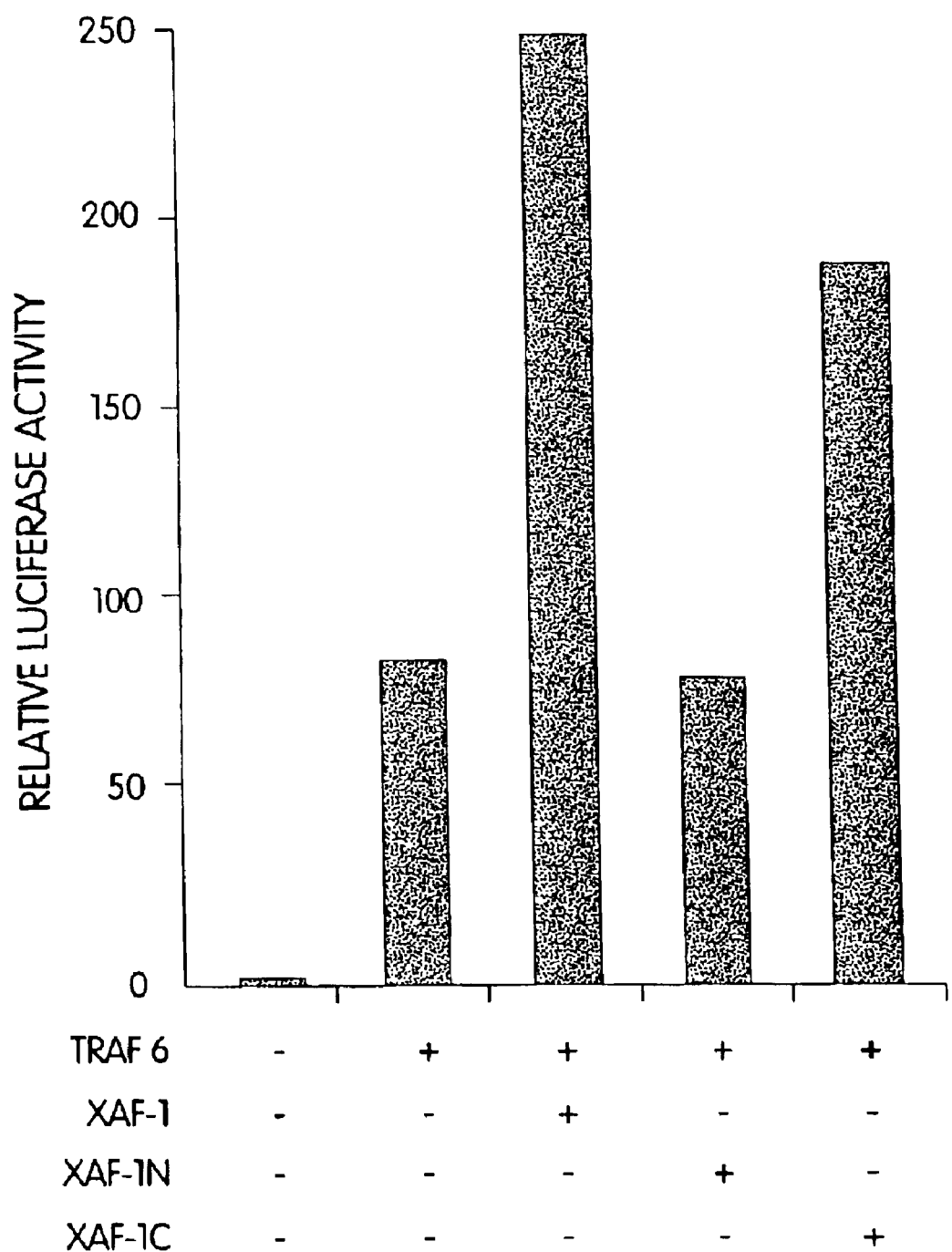
FIG. 26 is a graph of relative luciferase activity induced by NF-κB activation by TRAF6 co-expressed with either full-length XAF-1 protein, a fragment representing the N-terminus of XAF-1 protein, or a fragment representing the C-terminus of XAF1 protein.

As FIG. 26 demonstrates, we have found that the carboxy terminus of XAF-1 protein mediates the additive effect of XAF-1 on TRAF6 induction of NF-κB . XAF-1N expression did not augment the ability to TRAF6 to induce NF-κB, whereas XAF-1C augmented NF-κB induction by TRAF6 substantially. Full length XAF-1, as we showed previously in FIG. 21, clearly enhanced TRAF6 induction of NF-κB.

EXAMPLE XVIII

Inhibitory Effect of Antisense XAF-1 Expression on TRAF5- and TRAF6-Mediated NF-κB Activation in 293 T Cells Methods To generate the bcl-2 antisense construct, a 1.5 kb EcoRI fragment of bcl-2 was cloned in a non-coding orientation into the pcDNA3 plasmid commercially available from Invitrogen.

293T cells ($2 \times 10^5$) were transfected with 0.5 µg of pELAM-Lu reporter plasmid, 0.1 µg of pRL-TK commercially available from Promega, 0.5 µg of pCMV-TRAF5 or pCMV-TRAF6, 3 µg of indicated antisense plasmid: antisense XAF-1 (240-1) or antisense bcl-2 (450-23), and enough pCMV-myc control plasmid to give 5 µg of total DNA. Firefly luciferase activity were determined 24 hrs after transfection and normalized on the basis of Renilla luciferase expression level. Values shown are averages for an experiment in which each transfection was performed in duplicate.

Results

Figure 27:
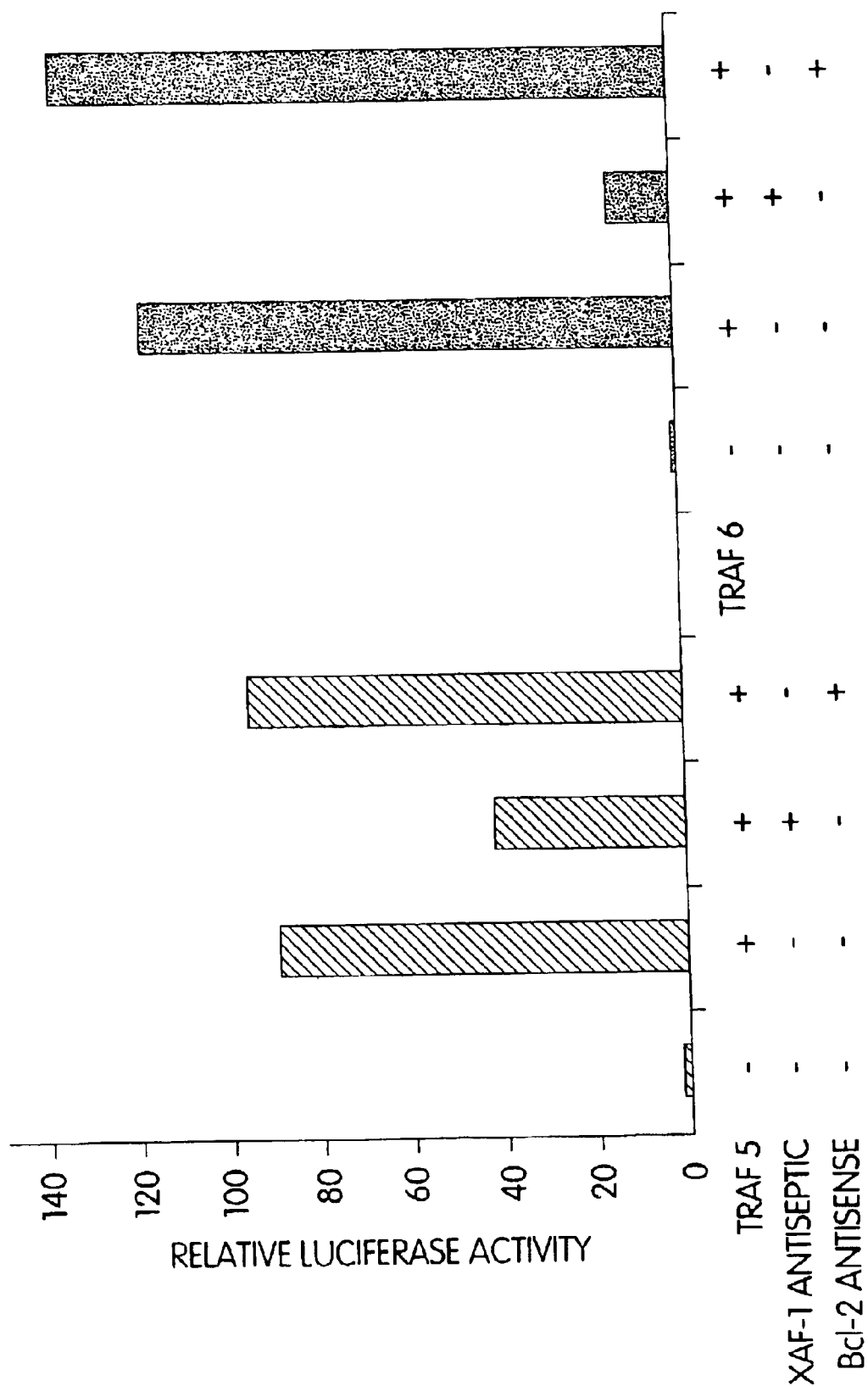
FIG. 27 is a graph of relative luciferase activity induced by NF-κB activation by either TRAF5 or TRAF6 when co-expressed with either XAF-1 antisense DNA or Bcl-2 antisense DNA.

FIG. 27 demonstrates that expression of antisense XAF-1 significantly inhibited TRAF6 induced activation of NF-κB and, to a lesser extent, TRAF5 induced activation of NF-κB. This inhibition was specific to XAF-1 since antisense bcl-2 did not have the same effect.

EXAMPLE XIX

Inhibitory Effect of Antisense XAF-1 Expression on IL-1β-Induced NF-κB Activation Methods 293T cells ($2 \times 10^5$) were transfected with 0.5 µg of pELAM-Lu reporter plasmid, 0.1 µg of pRL-TK commercially available from Promega, indicated amounts of antisense plasmid: antisense XAF-1 (240-1) or antisense bcl-2 (1486-23), and enough pCMV-myc control plasmid to give 5 µg of total DNA. 24 hrs after transfection, cells were treated for 6 hrs with 20 ng/ml of interleukin-1β (IL-1β). Firefly luciferase activity were determined after IL-1β treatment and normalized on the basis of Renilla luciferase expression level. Values shown are averages for an experiment in which each transfection was performed in duplicate.

Results

Figure 28:
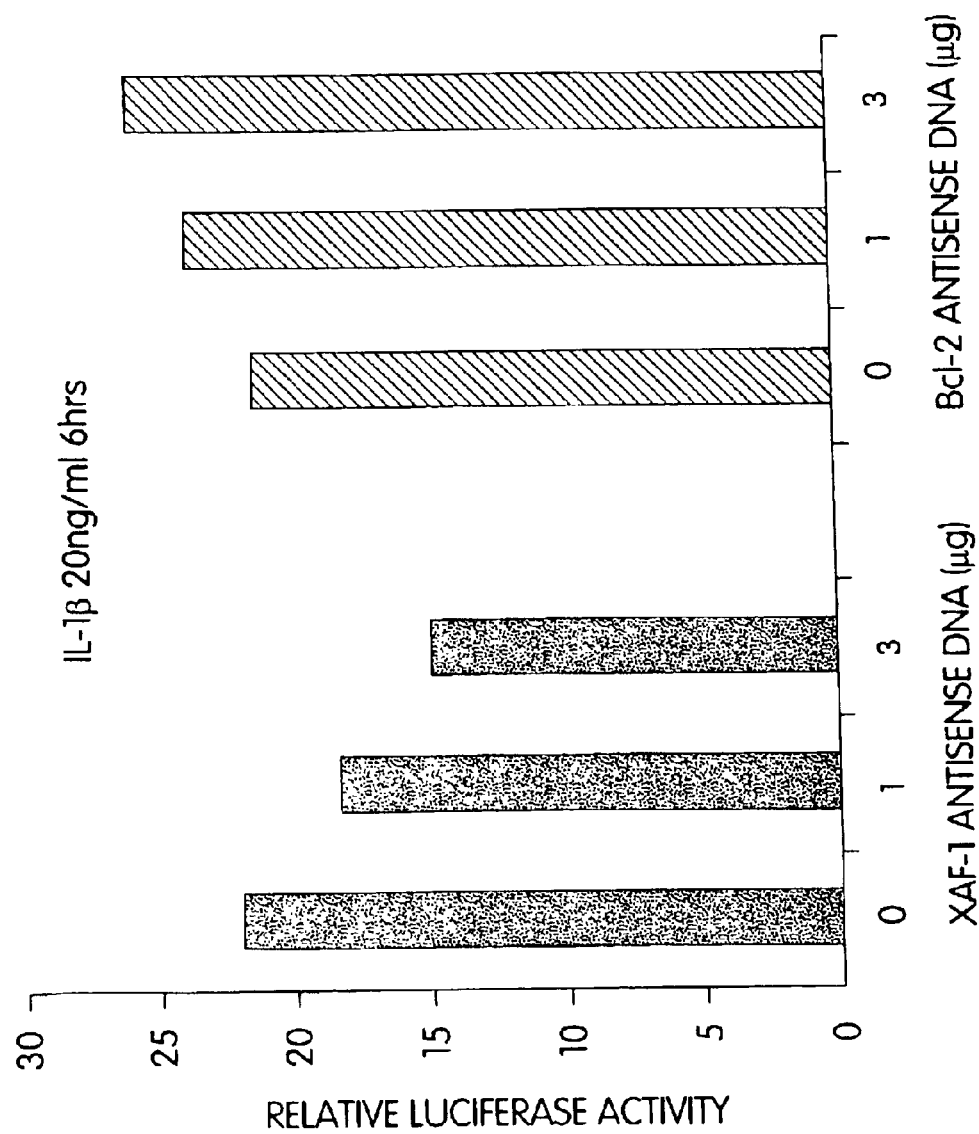
FIG. 28 is a graph of relative luciferase activity induced by NF-κB activation by interleukin-1β (IL-1β) in the presence of either XAF-1 antisense RNA or Bcl-2 antisense RNA expression.

As shown on FIG. 28, expression of antisense XAF-1 inhibited interleukin-1β induced activation of NF-κB. This inhibition was specific to XAF-1 since antisense bcl-2 does not have the same effect.

EXAMPLE XX

Dose Response Effect of XAF-1 Expression on IL-1β-Induced NF-κB Activation

Methods 293T cells ($2 \times 10^5$) were transfected with 0.5 µg of pELAM-Lu reporter plasmid, 0.1 µg of pRL-TK commercially available from Promega, indicated amounts of pCMV-XAF-1 and enough pCMV-myc control plasmid to give 5 µg of total DNA. 24 hrs after transfection, cells were treated for 6 hrs with 20 ng/ml of interleukin-1β (IL-1β). Firefly luciferase activity were determined after IL-1β treatment and normalized on the basis of Renilla luciferase expression level. Values shown are averages for an experiment in which each transfection was performed in duplicate.

Results

Figure 29:
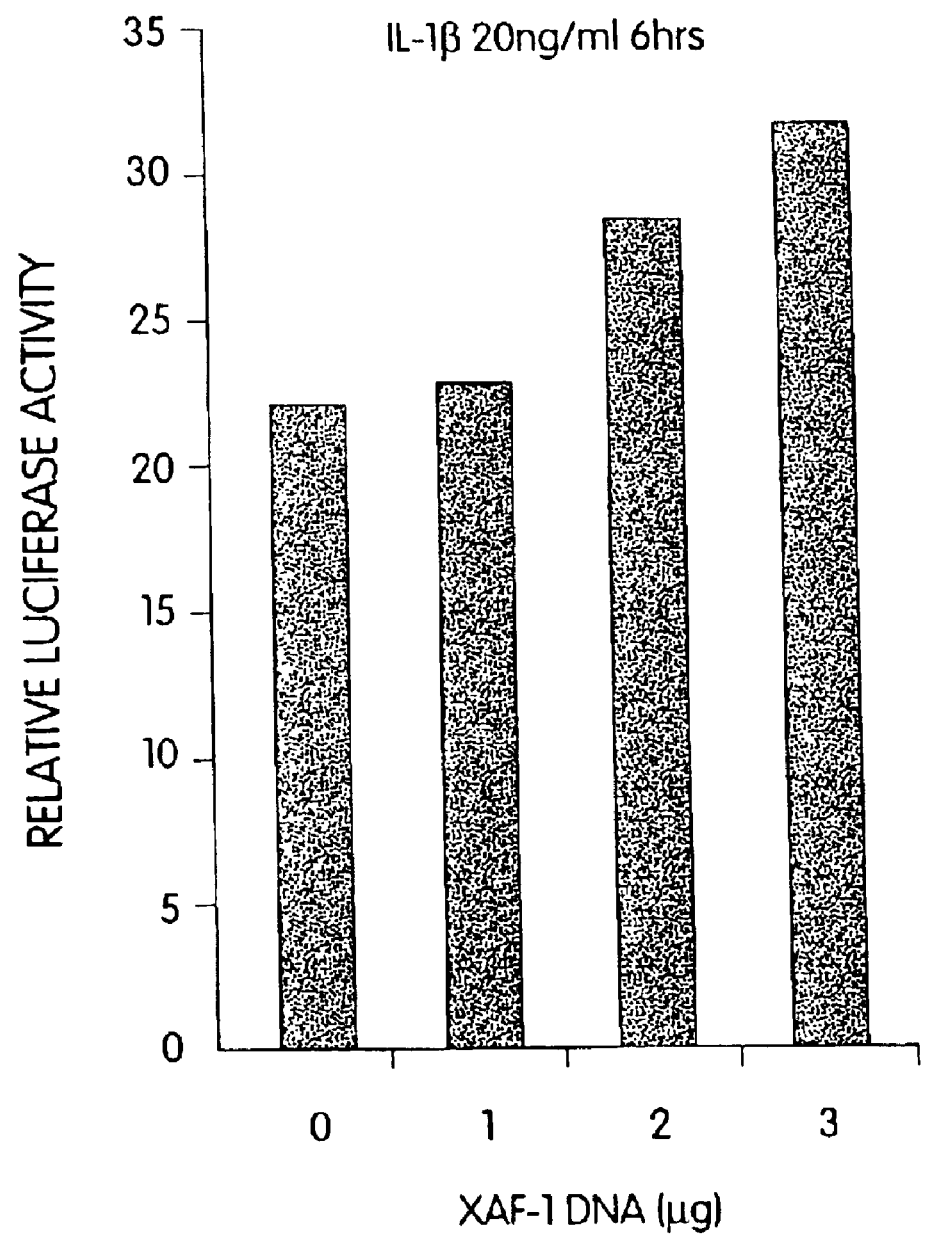
FIG. 29 is a graph of relative luciferase activity induced by NF-κB activation by interleukin-1β (IL-1β) in the presence of DNA encoding for XAF-1 protein.

Expression of full length XAF-1 augmented interleukin-1β mediated induction of NF-κB in a dose-dependent manner, as is demonstrated in FIG. 29.

EXAMPLE XXI

Inhibitory Effect of A20 Expression on TRAF2-, TRAF5- and TRAF6-Mediated NF-κB Activation The A20 protein is induced by NF-κB and binds to both TRAF1 and TRAF2, again via the TRAF-C domain. Binding of A20 to TRAF2 interferes with NF-κB activation in a negative feed-back loop (Song et al., Proc. Natl. Acad. Sci. USA 93: 6721–6725, 1996). It has previously been established that over-expression of A20 can render cells resistant to the apoptotic effects of TNFα (Opipari et al., J. Biol. Chem. 267: 12424–12427, 1992), and may also participate in rendering B cells resistant to apoptosis following CD40 signaling (Sarma et al., 270: 12353–12346, 1995).

Methods 293T cells ($2 \times 10^5$) were transfected with 0.5 µg of pELAM-Lu reporter plasmid, 0.1 µg of pRL-TK commercially available from Promega, 0.5 µg of pCMV-TRAF2, pCMV-TRAF5 or pCMV-TRAF6, 0.3 µg of pCMV-A20 and enough pCMV-myc control plasmid to give 4 µg of total DNA. Firefly luciferase activity were determined 24 hrs after transfection and normalized on the basis of Renilla luciferase expression level. Values shown are averages for an experiment in which each transfection was performed in duplicate.

Results

Figure 30:
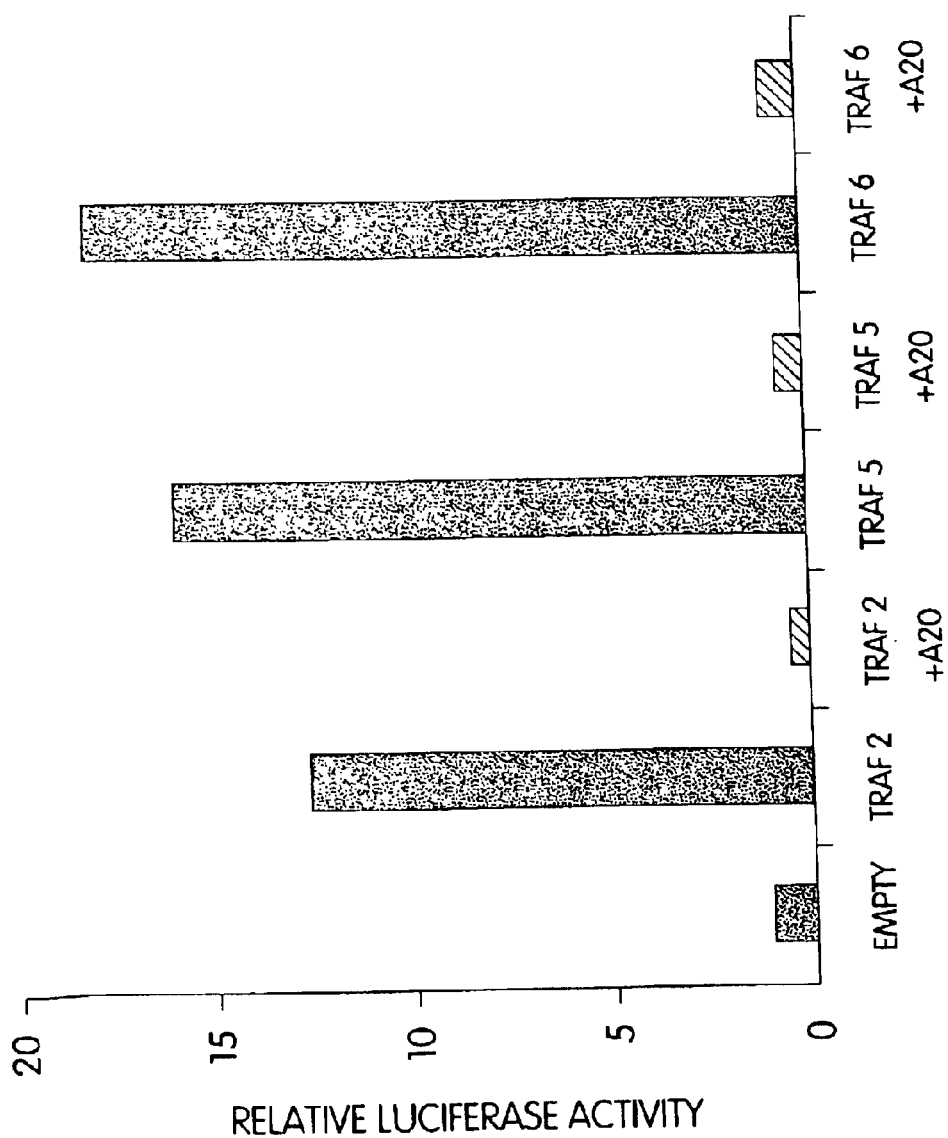
FIG. 30 is a graph of relative luciferase activity induced by NF-κB activation by TRAF2, TRAF5, or TRAF6 co-expressed with A20 protein.

In the experiments shown on FIG. 30, co-transfection of an A20 expression vector with either TRAF2, TRAF5 or TRAF6 resulted in virtually complete inhibition of NF-κB transactivation.

EXAMPLE XXII

XAF-1 Counters the Effect of A20 Expression on TRAF6 Mediated Induction of NF-κB Methods 293T cells ($2 \times 10^5$) were transfected with 0.5 µg of pELAM-Lu reporter plasmid, 0.1 µg of pRL-TK commercially available from Promega, 0.5 µg of pCMV-TRAF6, 2 µg of pCMV-XAF-1, indicated amounts of pCMV-A20 and enough pCMV-myc control plasmid to give 5 µg of total DNA. Firefly luciferase activity were determined 24 hrs after transfection and normalized on the basis of Renilla luciferase expression level. Values shown are averages for an experiment in which each transfection was performed in duplicate.

Results

Figure 31:
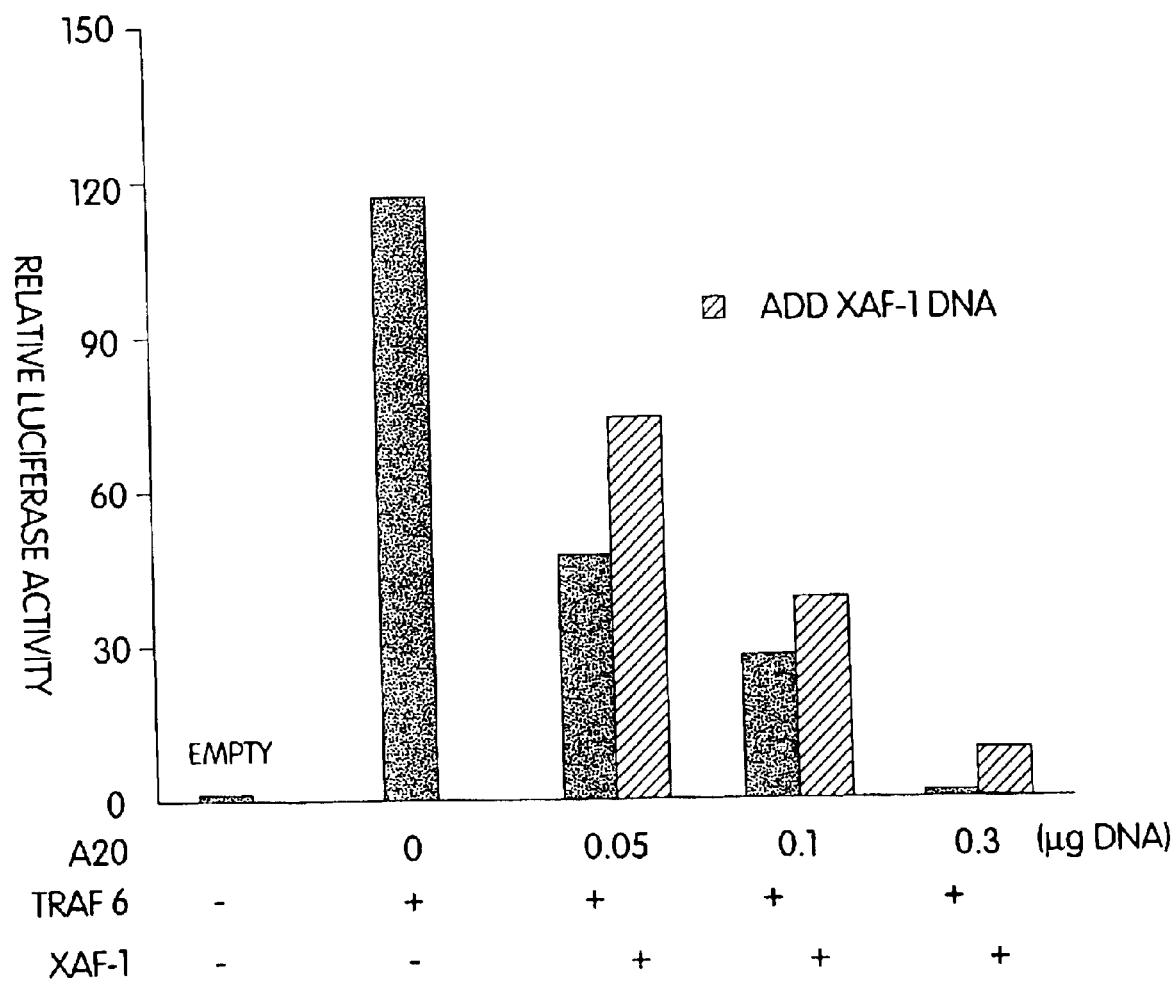
FIG. 31 is a graph of relative luciferase activity induced by NF-κB activation by increasing amounts of A20 protein co-expressed with TRAF6 alone, or in combination with XAF-1.

As shown in FIG. 31, XAF-1 expression had a partial neutralizing effect on the A20-mediated inhibitory function of TRAF6-mediated NF-κB activation.

EXAMPLE XXIII

Interaction of XAF-1 with the Various TRAFs and Mammalian IAPs

Methods

XIAP and XAF-1 coding regions were cloned in frame into the pGEX-4T-1 expression vector which is commercially available from Pharmacia. Expression and purification of GST-fusion proteins were performed essentially according to the manufacturer's protocol (Pharmacia).

293T cells were transiently transfected with myc-epitope tagged TRAFs and mammalian IAPs expression vectors (5 µg). After 36 hrs, cells were lysed and cell lysates were incubated with GST-XAF-1 fusion protein or GST-control protein (Glutathione-s-transferase from Schistosoma Japonicum) immobilized on 10 µl of glutathione beads.

Figure 32:
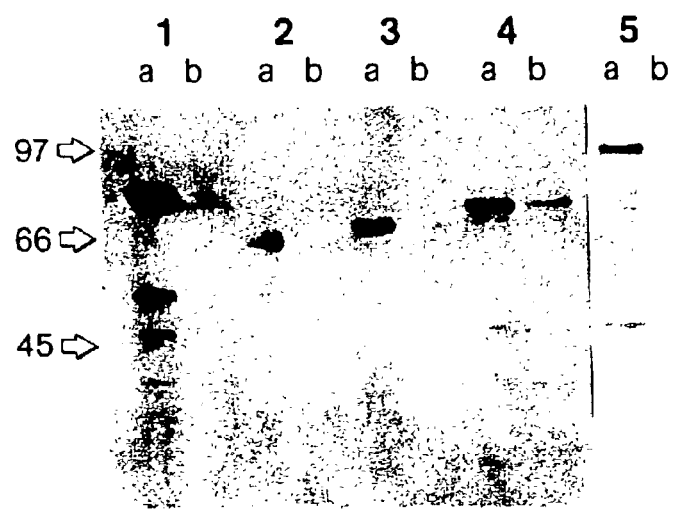
FIG. 32 is a Western blot analysis of myc-tagged proteins from affinity-purifications with GST-control and GST-XAF-1 fusion proteins.

Protein adsorbed to beads were analyzed by SDS-PAGE, followed by Western blotting using anti-c-myc monoclonal antibody (9E10). Lanes were loaded as follows:
lane 1: HIAP-2,
lane 2: TRAF1,
lane 3: TRAF2,
lane 4: TRAF3,
lane 5: A20.
Proteins in A lanes were affinity-purified with the GST-XAF-1 fusion protein.
Proteins in B lanes were affinity-purified with the GST-control protein.
Results GST interaction analysis indicated that XAF-1 can form complexes with a variety of cellular proteins, including HIAP-2, TRAF1, TRAF2, and A20, as is shown on FIG. 32. In this type of analysis, indirect interactions cannot be distinguished from direct binding. For instance, XAF-1 may bind TRAF2 directly (as shown by two-hybrid analysis) which in turn can interact with either TRAF1 or A20.

EXAMPLE XXIV

In Vitro Translated TRAF2 and HIAP-1 Bind XAF-1

Methods $^{35}$S-labeled in vitro translated proteins were generated by using the various TRAF2 and HIAP-1 expression constructs in pCDNA3-myc with the TNT T7 Coupled Reticulocyte Lysate System, according to the manufacturer's descriptions (Promega) and $^{35}$S labeled methionine, commercially available from DuPont/NEN.

Figure 33:
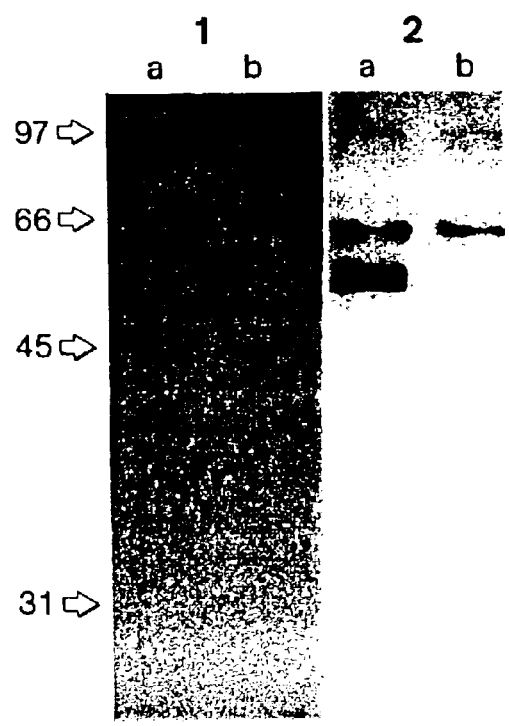
FIG. 33 is an autoradiograph of an in vitro binding assay of in vitro translated HIAP-1 and TRAF2 proteins with GST-control and GST-XAF-1 fusion proteins.

$^{35}$S-labeled in vitro translated proteins were incubated with GST-XAF-1 fusion protein or GST-control protein immobilized on 10 μl of glutathione beads. Protein adsorbed to beads were analyzed by SDS-PAGE. The protein bearing gel was then dried, and adsorbed proteins were detected by autoradiograph of the gel. The lanes were loaded as follows:
lane 1: HIAP1,
lane 2: TRAF2.
Proteins in A lanes were affinity-purified with the GST-XAF-1 fusion protein.
Proteins in B lanes were affinity-purified with the GST-control protein.
Results As shown on FIG. 33, both in vitro translated HIAP-1 and TRAF2 bound the GST-XAF-1 fusion protein, but do not bind the GST control protein. Since this experiment was done in a cell-free system, we have demonstrated that the HIAP-1:XAF-1 and the TRAF2:XAF-1 interactions are direct.

EXAMPLE XXV

XAF-1 Directly Interacts with XIAP, HIAP-1, HIAP-2, and TRAF2

Methods

The plasmids pAS2-XIAP, pAS2-HIAP-1, pAS2-HIAP-2, pAS$^2$-TRAF2, pAS2-TRAF4, pAS2-XAF-1, and pAS2 (vector only) which encode the GAL4 DNA-binding domains fused to indicated full-length proteins, were used as baits (DNA-binding domain hybrids) in two-hybrid screens of pGAD GH plasmids (commercially available from Clontech) encoding XIAP, HIAP-1, HIAP-2, TRAF2, TRAF4, and XAF-1 as preys (activation domain hybrids). The yeast two-hybrid assay and isolation of positive clones and subsequent interaction analyses were carried out as described elsewhere (PCT Publication WO 95/28497). DNA sequence was performed on an Applied Biosytems model 373A automated DNA sequencer.
Results Shown in FIG. 34 is a listing of the XAF-1 interactions with mammalian IAPs and TRAFS found in the yeast two-hybrid assay. Our results indicated that XAF-1 directly interacts with XIAP, HIAP-1, HIAP-2, and TRAF2 (but not TRAF4). As has been established in the literature, TRAF2 can interact with TRAF1 or A20. Since we have shown here in yeast two-hybrid analysis that XAF-1 binds TRAF2 directly, it may be through this interaction that XAF-1 is able to form a complex with TRAF1 and A20, as we showed in FIG. 32.

EXAMPLE XXVI

Identification and Cloning of Human XAF-2

Methods

Figure 40:
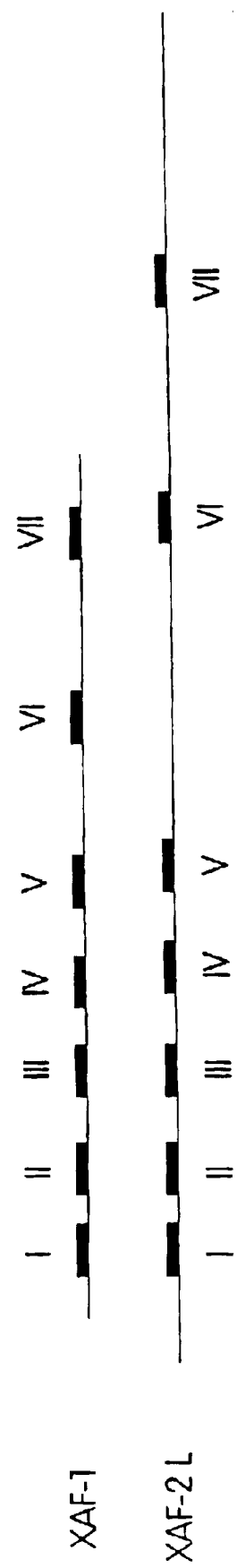
FIG. 40 is a set of two schematic drawings indicating the alignment of the zinc finger binding domains in XAF-1 (above) and XAF-2L (below).

We screened the database for ESTs that have significant homology to XAF-1. A number of such ESTs were identified. From the EST sequences, we have made oligonucleotide primers and PCR cloned a cDNA encoding a protein which we have named "XAF-2."
Results FIG. 35 shows the partial 5' nucleic acid (SEQ ID NO.: 3) and N-terminal amino acid (SEQ ID NO.: 4) sequences of the long splice variant of XAF-2. The N-terminus of XAF-2 protein has five zinc fingers in the N-terminal 150 amino acids which show 38% amino acid identity to XAF-1 (SEQ ID NO.: 2). XAF-2 also has a unique C-terminus that has two RING zinc fingers, so that the entire XAF-2 protein, like XAF-1, has seven zinc finger binding domains. FIG. 36 shows sequence of the 3' untranslated region (UTR) located approximately 250 nucleic acid residues C-terminally to the nucleic acid sequence of FIG. 35. There are at least two splice variants of XAF-2. FIG. 37A shows the full length 5' nucleotide (above; SEQ ID NO.: 9) and amino acid (below; SEQ ID NO.: 10) sequences of the long (XAF-2L) splice variant of XAF-2. The shorter splice form of XAF-2 (XAF-2S) is spliced as indicated in FIG. 37A, with the nucleic acid encoding XAF-2S indicated in FIG. 37B, lower sequence (SEQ ID NO.: 11). FIGS. 38A, 38B, and 38C show the indicated zinc finger binding domains in the amino acid sequence listings of XAF-1, XAF-2L, and XAF-2S, respectively. XAF-2L and XAF-1 shown an overall amino acid sequence identity of 27%, although the first 135 amino acids of XAF-2L and the first 131 amino acids of XAF-1 share a 40% amino acid sequence identity (FIG. 39). As indicated in FIG. 40, the alignment of the zinc finger binding domains in XAF-1 and XAF-2L is not equivalent: the sixth zinc domain of XAF-2L aligns with the seventh zinc domain of XAF-1. However, the two XAF molecules both have seven zinc finger binding domains overall.

EXAMPLE XXVII

A Screen for Candidate Compounds which Modulate XAF-1 Expression

Compounds are screened for an ability to modulate XAF-1 expression by looking at the ability of the compounds to modulate the expression of a luciferase reporter gene operably linked to the XAF-1 promoter.
Methods The XAF-1 promoter firefly luciferase reporter plasmid pXAF-1prom-Lu is constructed by insertion of PCR-amplified XAF-1 promoter sequences into a vector such as the pGL3-Basic vector which is commercially available from Promega.

COS cells are seeded into six-well plates at 2×10⁵ cells per well 24 hrs before transfection. Cells are then transfected with 1.0 μg of pXAF-1prom-Lu reporter plasmid, and 3.0 μg pCMV-myc control plasmid by standard lipofection methods using Trans-IT lipofection reagent commercially available from Mirus. Twenty-four hours after transfection, varying concentrations of different compounds are added to the culture supernatant of transfected cells, such that there is one compound, or combination thereof, per well. Twelve hours following treatment with the compound, the cells are washed with PBS and lysed in 400 μl of Passive Lysis Buffer commercially available from Promega. Lysate (20 μl) from each samples is used to measure firefly luciferase activity. Firefly luciferase activity is determined and normalized on the basis of Renilla luciferase expression level. Luciferase activity is measured in a model TD20/20 luminometer using the Dual luciferase assay system according to the manufacture's protocol (Promega).

Results

Compound-treated cells which show an increased firefly luciferase activity as compared to untreated control cells indicate a compound with an ability to increase XAF-1 activity. Compound-treated cells which show a decreased firefly luciferase activity as compared to untreated control cells indicate a compound with an ability to decrease XAF-1 activity.

OTHER EMBODIMENTS

In other embodiments, the invention includes any protein which is substantially identical to a mammalian XAF polypeptide provided in FIG. 1 (SEQ. ID NO.: 2), FIG. 35 (SEQ ID NO.: 4), FIG. 37A (SEQ ID NO.: 10) and FIG. 38C (SEQ ID NO.: 12); such homologues include other substantially pure naturally-occurring mammalian XAF proteins as well as splice variants, allelic variants; natural mutants; induced mutants; DNA sequences which encode proteins and also hybridize to the XAF DNA sequences of FIG. 1 (SEQ ID NO.: 1), FIG. 35 (SEQ ID NO.: 3), FIG. 37A (SEQ ID NO.: 9) and FIG. 37B (SEQ ID NO.: 11) under high stringency conditions (e.g., hybridizing at 2×SSC at 40° C. with a probe length of at least 40 nucleotides) or, less preferably, under low stringency conditions (e.g., hybridizing at 5×SSC at 25° C. with a probe length of at least 80 nucleotides); and proteins specifically bound by antisera directed to a XAF polypeptide. The term also includes chimeric polypeptides that include a portion derived from a XAF polypeptide.

The invention further includes analogs of any naturally-occurring XAF polypeptides. Analogs can differ from the naturally-occurring XAF proteins by amino acid sequence differences, by post-translational modifications, or by both. Analogs of the invention will generally exhibit at least 85%, more preferably 90%, and most preferably 95% or even 99% identity with all or part of a naturally occurring XAF-1, XAF-2 N-terminus, XAF-2L, or XAF-2S amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring XAF-1, XAF-2 N-terminus, XAF-2L or XAF-2S polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., B or Y amino acids. In addition to full-length polypeptides, the invention also includes XAF-1, XAF-2 N-terminus, XAF-2L and XAF-2S polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of XAF-1, XAF-2 N-terminus, XAF-2L and XAF-2S polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a XAF-1, XAF-2 N terminus, XAF-2L or XAF-2S nucleic acid or amino acid sequence in a sample to be diagnosed. Particularly useful XAF-1 fragments for this purpose include, without limitation, the amino acid fragments shown in FIG. 7.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

What is claimed is:

1. A substantially purified polypeptide comprising at least 85% amino acid sequence identity to SEQ ID NO: 2, 4, 10, or 12, and having XAF biological activity.

2. The substantially purified polypeptide of claim 1, wherein said polypeptide comprises at least 85% amino acid sequence identity to SEQ ID NO: 2.

3. The substantially purified polypeptide of claim 1, wherein said polypeptide comprises at least 85% amino acid sequence identity to SEQ ID NO: 4.

4. The substantially purified polypeptide of claim 1, wherein said polypeptide comprises at least 85% amino acid sequence identity to SEQ ID NO: 10.

5. The substantially purified polypeptide of claim 1, wherein said polypeptide comprises at least 85% amino acid sequence identity to SEQ ID NO: 12.

6. The substantially purified polypeptide of claim 1, wherein said polypeptide comprises the amino acid sequence of SEQ ID NO: 2, 4, 10, or 12.

7. The substantially purified polypeptide of claim 6, wherein said polypeptide consists of the amino acid sequence of SEQ ID NOs: 2, 4, 10, or 12.

8. The substantially purified polypeptide of claim 1, wherein said XAF biological activity is induction of apoptosis.

9. A composition comprising a substantially purified polypeptide comprising at least 85% amino acid sequence identity to SEQ ID NO: 2, 4, 10, or 12, and having XAF biological activity.

10. The composition of claim 9, wherein said polypeptide consists of the amino acid sequence of SEQ ID NOs: 2, 4, 10, or 12.

11. The composition of claim 9, wherein said XAF biological activity is induction of apoptosis.

* * * * *

UNITED STATES PATENT AND TRADEMARK OFFICE
CERTIFICATE OF CORRECTION

PATENT NO. : 6,946,544 B2 Page 1 of 1
APPLICATION NO. : 10/288273
DATED : September 20, 2005
INVENTOR(S) : Korneluk et al.

It is certified that error appears in the above-identified patent and that said Letters Patent is hereby corrected as shown below:

On the cover page,

[*] Notice: Subject to any disclaimer, the term of thi patent is extended or adjusted under 35 USC 154(b) by (194) days Delete the phrase "by 194 days" and insert – by 189 days--

Signed and Sealed this

Twenty-ninth Day of August, 2006

JON W. DUDAS
*Director of the United States Patent and Trademark Office*

SEQUENCE LISTING

<160> NUMBER OF SEQ ID NOS: 143

<210> SEQ ID NO 1
<211> LENGTH: 1326
<212> TYPE: DNA

<213> ORGANISM: Homo sapiens

<400> SEQUENCE: 1

```
atggaaggag acttctcggt gtgcaggaac tgtaaaagac atgtagtctc tgccaacttc    60
accctccatg aggcttactg cctgcggttc ctggtcctgt gtccggagtg tgaggagcct   120
gtccccaagg aaaccatgga ggagcactgc aagcttgagc accagcaggt tgggtgtacg   180
atgtgtcagc agagcatgca gaagtcctcg ctggagtttc ataaggccaa tgagtgccag   240
gagcgccctg ttgagtgtaa gttctgcaaa ctggacatgc agctcagcaa gctggagctc   300
cacgagtcct actgtggcag ccggacagag ctctgccaag ctgtggcca gttcatcatg   360
caccgcatgc tcgcccagca cagagatgtc tgtcggagtg aacaggccca gctcgggaaa   420
ggggaaagaa tttcagctcc tgaaagggaa atctactgtc attattgcaa ccaaatgatt   480
ccagaaaata gtatttcca ccatatgggt aaatgttgtc cagactcaga gtttaagaaa   540
cactttcctg ttgaaatcc agaaattctt ccttcatctc ttccaagtca agctgctgaa   600
aatcaaactt ccacgatgga gaaagatgtt cgtccaaaga caagaagtat aaacagattt   660
cctcttcatt ctgaaagttc atcaaagaaa gcaccaagaa gcaaaaacaa acccttggat   720
ccactttga tgtcagagcc aagcccagg accagctccc ctagaggaga taaagcagcc   780
tatgacattc tgaggagatg ttctcagtgt ggcatcctgc ttcccctgcc gatcctaaat   840
caacatcagg agaaatgccg gtggttagct tcatcaaaaa ggaaaacaag tgagaaattt   900
cagctagatt tggaaaagga aaggtactac aaattcaaaa gatttcactt ttaacactgg   960
cattcctgcc tacttgctgt ggtggtcttg tgaaggtga tgggttttat tcgttgggct  1020
ttaaaagaaa aggtttggca gaactaaaaa caaaactcac gtatcatctc aatagataca  1080
gaaaaggctt ttgataaaat tcaacttgac ttcatgttaa aaccctcaa caaaccaggc  1140
gtcgaaggaa catacctcaa ataataaga gccatctatg acaaaaccac agccaacatc  1200
atactgaatg agcaaaagct ggagcattac tcttgagaag tagaacaagg cacttcagtc  1260
ctattcaaca tagtactgga agtctcgcca cagcaatcag gcaagagaaa gaagtaaaag  1320
gcaccc                                                             1326
```

<210> SEQ ID NO 2
<211> LENGTH: 317
<212> TYPE: PRT
<213> ORGANISM: Homo sapiens

<400> SEQUENCE: 2

```
Met Glu Gly Asp Phe Ser Val Cys Arg Asn Cys Lys Arg His Val Val
 1               5                  10                  15

Ser Ala Asn Phe Thr Leu His Glu Ala Tyr Cys Leu Arg Phe Leu Val
            20                  25                  30

Leu Cys Pro Glu Cys Glu Glu Pro Val Pro Lys Glu Thr Met Glu Glu
        35                  40                  45

His Cys Lys Leu Glu His Gln Gln Val Gly Cys Thr Met Cys Gln Gln
    50                  55                  60

Ser Met Gln Lys Ser Ser Leu Glu Phe His Lys Ala Asn Glu Cys Gln
65                  70                  75                  80

Glu Arg Pro Val Glu Cys Lys Phe Cys Lys Leu Asp Met Gln Leu Ser
                85                  90                  95

Lys Leu Glu Leu His Glu Ser Tyr Cys Gly Ser Arg Thr Glu Leu Cys
            100                 105                 110
```

-continued

```
Gln Gly Cys Gly Gln Phe Ile Met His Arg Met Leu Ala Gln His Arg
            115                 120                 125

Asp Val Cys Arg Ser Glu Gln Ala Gln Leu Gly Lys Gly Glu Arg Ile
        130                 135                 140

Ser Ala Pro Glu Arg Glu Ile Tyr Cys His Tyr Cys Asn Gln Met Ile
145                 150                 155                 160

Pro Glu Asn Lys Tyr Phe His His Met Gly Lys Cys Cys Pro Asp Ser
                165                 170                 175

Glu Phe Lys Lys His Phe Pro Val Gly Asn Pro Glu Ile Leu Pro Ser
            180                 185                 190

Ser Leu Pro Ser Gln Ala Ala Glu Asn Gln Thr Ser Thr Met Glu Lys
        195                 200                 205

Asp Val Arg Pro Lys Thr Arg Ser Ile Asn Arg Phe Pro Leu His Ser
    210                 215                 220

Glu Ser Ser Ser Lys Lys Ala Pro Arg Ser Lys Asn Lys Thr Leu Asp
225                 230                 235                 240

Pro Leu Leu Met Ser Glu Pro Lys Pro Arg Thr Ser Ser Pro Arg Gly
                245                 250                 255

Asp Lys Ala Ala Tyr Asp Ile Leu Arg Arg Cys Ser Gln Cys Gly Ile
            260                 265                 270

Leu Leu Pro Leu Pro Ile Leu Asn Gln His Gln Glu Lys Cys Arg Trp
        275                 280                 285

Leu Ala Ser Ser Lys Arg Lys Thr Ser Glu Lys Phe Gln Leu Asp Leu
    290                 295                 300

Glu Lys Glu Arg Tyr Tyr Lys Phe Lys Arg Phe His Phe
305                 310                 315

<210> SEQ ID NO 3
<211> LENGTH: 1311
<212> TYPE: DNA
<213> ORGANISM: Homo sapiens

<400> SEQUENCE: 3
gcagctagtg tgtcatttca gcgtttctcc tctcgtccct ggaagagcta agatggctg       60 aatttctaga tgaccaggaa actcgactgt gtgacaactg caaaaaagaa attcctgtgt     120
ttaactttac catccatgag atccactgtc aaaggaacat tggtatgtgt cctacctgta     180
aggaaccatt tcccaaatct gacatggaga ctcacatggc tgcagaacac tgtcaggtga     240
cctgcaaatg taacaagaag ttggagaaga ggctgttaaa gaagcatgag agactgagt      300 gcccttttgcg gcttgctgtc tgccagcact gtgatttaga actttccatt ctcaaactga     360
aggaacatga agattattgt ggtgcccgga cggaactatg tggcaactgt ggtcgcaatg     420
tccttgtgaa agatctgaag actcaccctg aagtttgtgg gagagagggg gaggaaaaga     480
gaaatgaggt tgccatacct cctaatgcat atgatgaatc ttggggtcag atgaatct       540 ggattgcatc ccaactcctc agacaaattg aggctctgga cccacccatg aggctgccgc     600
gaaggcccct gagagccttt gaatcagatg ttttccacaa tagaactacc aaccaaagga     660
acattacagc ccaggtttca attcagaata atctgtttga agaacaagag aggcaggaaa     720
ggaatagagg ccaacagccc cccaaagagg gtggtgaaga gagtgcaaac ttggacttca     780
tgttggccct aagtctgcaa aatgaaggcc aagcctccag tgtggcagag caggacttct     840
ggagggccgt atgtgaggcc gaccagtctc atggcggtcc caggtctctc agtgacataa     900
agggtgcagc tgacgagatc atgttgcctt gtgaattttg tgaggagctc tacccagagg     960
```

-continued

```
aactgctgat tgaccatcag acaagctgta acccttcacg tgccttacct tcactcaata    1020
ctggcagctc ttcccccaga ggggtggagg aacctgatgt catcttccag aactccttgc    1080
aacaggctgc aagtaaccag ttagactctt tgatgggcct gagcaattca caccctgtgg    1140
aggagagcat cattatccca tgtgaattct gtggggtaca gctggaagag gaggtgctgt    1200
tccatcacca ggaccagtgt gaccaacgcc cagccactgc aaccaaccat gtgacagagg    1260
ggattcctag actggattcc cagcctcaag agccccttcc ccttgttttt a             1311
```

<210> SEQ ID NO 4
<211> LENGTH: 419
<212> TYPE: PRT
<213> ORGANISM: Homo sapiens

<400> SEQUENCE: 4

```
Met Ala Glu Phe Leu Asp Asp Gln Glu Thr Arg Leu Cys Asp Asn Cys
 1               5                  10                  15

Lys Lys Glu Ile Pro Val Phe Asn Phe Thr Ile His Glu Ile His Cys
            20                  25                  30

Gln Arg Asn Ile Gly Met Cys Pro Thr Cys Lys Glu Pro Phe Pro Lys
        35                  40                  45

Ser Asp Met Glu Thr His Met Ala Ala Glu His Cys Gln Val Thr Cys
    50                  55                  60

Lys Cys Asn Lys Lys Leu Glu Lys Arg Leu Leu Lys Lys His Glu Glu
65                  70                  75                  80

Thr Glu Cys Pro Leu Arg Leu Ala Val Cys Gln His Cys Asp Leu Glu
                85                  90                  95

Leu Ser Ile Leu Lys Leu Lys Glu His Glu Asp Tyr Cys Gly Ala Arg
            100                 105                 110

Thr Glu Leu Cys Gly Asn Cys Gly Arg Asn Val Leu Val Lys Asp Leu
        115                 120                 125

Lys Thr His Pro Glu Val Cys Gly Arg Glu Gly Glu Lys Arg Asn
    130                 135                 140

Glu Val Ala Ile Pro Pro Asn Ala Tyr Asp Glu Ser Trp Gly Gln Asp
145                 150                 155                 160

Gly Ile Trp Ile Ala Ser Gln Leu Leu Arg Gln Ile Glu Ala Leu Asp
                165                 170                 175

Pro Pro Met Arg Leu Pro Arg Arg Pro Leu Arg Ala Phe Glu Ser Asp
            180                 185                 190

Val Phe His Asn Arg Thr Thr Asn Gln Arg Asn Ile Thr Ala Gln Val
        195                 200                 205

Ser Ile Gln Asn Asn Leu Phe Glu Glu Gln Glu Arg Gln Glu Arg Asn
    210                 215                 220

Arg Gly Gln Gln Pro Pro Lys Glu Gly Gly Glu Glu Ser Ala Asn Leu
225                 230                 235                 240

Asp Phe Met Leu Ala Leu Ser Leu Gln Asn Glu Gly Gln Ala Ser Ser
                245                 250                 255

Val Ala Glu Gln Asp Phe Trp Arg Ala Val Cys Glu Ala Asp Gln Ser
            260                 265                 270

His Gly Gly Pro Arg Ser Leu Ser Asp Ile Lys Gly Ala Ala Asp Glu
        275                 280                 285

Ile Met Leu Pro Cys Glu Phe Cys Glu Glu Leu Tyr Pro Glu Glu Leu
    290                 295                 300

Leu Ile Asp His Gln Thr Ser Cys Asn Pro Ser Arg Ala Leu Pro Ser
305                 310                 315                 320
```

Leu Asn Thr Gly Ser Ser Pro Arg Gly Val Glu Pro Asp Val
            325                 330                 335

Ile Phe Gln Asn Ser Leu Gln Gln Ala Ala Ser Asn Gln Leu Asp Ser
        340                 345                 350

Leu Met Gly Leu Ser Asn Ser His Pro Val Glu Ser Ile Ile Ile
            355                 360                 365

Pro Cys Glu Phe Cys Gly Val Gln Leu Glu Glu Val Leu Phe His
        370                 375                 380

His Gln Asp Gln Cys Asp Gln Arg Pro Ala Thr Ala Thr Asn His Val
385                 390                 395                 400

Thr Glu Gly Ile Pro Arg Leu Asp Ser Gln Pro Gln Glu Pro Leu Pro
            405                 410                 415

Leu Val Phe

<210> SEQ ID NO 5
<211> LENGTH: 1169
<212> TYPE: DNA
<213> ORGANISM: Homo sapiens

<400> SEQUENCE: 5
tgggtgccag cccagctctc cttgtgtgcc gaagctcagc aactcagaca gccaggacat      60
ccagggggcgg aatcgagaca gccagaatgg ggccatagcc cctgggcacg tttcagtgat    120
tcgccctcct caaaatctct acccagaaaa cattgtgccc tctttctccc gtgggccttc    180
agggagatac ggagctagtg gtaggagtga aggtggcagg aattcccggg tcacccctgc    240
agctgccaac taccgcagca gaactgcaaa ggcaaagcct tccaagcaac agggagctgg    300
ggatgcagaa gaggaagagg aggagtaatg gtgtctccag agactttaca tcggttcctg    360
tcttctgtgc acagcagcac ttgccgctgt gcaggcccac ctctttggct ctttgggtgg    420
gagagttttt ccagattttta gattttctaa ggttatggcc attttgtgtc ttttgaggtt    480
gtgctgtggg ggtttgggtt tgagggaagg gagcagggtg gcggttgagg aacgcttcag    540
ccttagctgc taccttttcgg cagcagtgaa atacaagctg cagcctcggc tgccagggct    600
cccttttgac ttattgtcgc cactgcccct tggtgctgtg tggtcccagt ggaaggaggg    660
gaagattttg gaaacctggt agccaccagt aaggtgattc tctgccctgt tggggcctaa    720
atttgggggc ttttgggcaa cctctccgtg tactgcgtct gtccacactc gattgggccc    780
caggtgtgta tgaggcgctc tggtaaggtg ctcaggccag ttgcaatgtc tgtcagtaac    840
gaggcttttg atgtgttgag ctggaggtga gtggaccggg ggctgtgttt taagctgctt    900
ccttggcatt tggcatcact gccttctgtt cccgggggag catggatctt ttgtcctcac    960
tgctttctaa tggggagggc tgagggctcc ctgtccccac agcaggtatg gttgctctgc   1020
cccagcccca cacttgctct gaaaaccaag tgtcagagcc ccttcccctt gttttttattt   1080
tactgttata ataattatta acttccttgt aatagaaata agtttgtac ttggaaaaaa    1140
aaaaaaaaaa aaaaaaaaaa aaaaaaaa                                      1169

<210> SEQ ID NO 6
<211> LENGTH: 178
<212> TYPE: PRT
<213> ORGANISM: Homo sapiens

<400> SEQUENCE: 6

Met Glu Gly Asp Phe Ser Val Cys Arg Asn Cys Lys Arg His Val Val
1               5                   10                  15

```
Ser Ala Asn Phe Thr Leu His Glu Ala Tyr Cys Leu Arg Phe Leu Val
            20                  25                  30

Leu Cys Pro Glu Cys Glu Glu Pro Val Pro Lys Glu Thr Met Glu Glu
        35                  40                  45

His Cys Lys Leu Glu His Gln Gln Val Gly Cys Thr Met Cys Gln Gln
    50                  55                  60

Ser Met Gln Lys Ser Ser Leu Glu Phe His Lys Ala Asn Glu Cys Gln
65                  70                  75                  80

Glu Arg Pro Val Glu Cys Lys Phe Cys Lys Leu Asp Met Gln Leu Ser
                85                  90                  95

Lys Leu Glu Leu His Glu Ser Tyr Cys Gly Ser Arg Thr Glu Leu Cys
            100                 105                 110

Gln Gly Cys Gly Gln Phe Ile Met His Arg Met Leu Ala Gln His Arg
        115                 120                 125

Asp Val Cys Arg Ser Glu Gln Ala Gln Leu Gly Lys Gly Glu Arg Ile
    130                 135                 140

Ser Ala Pro Glu Arg Glu Ile Tyr Cys His Tyr Cys Asn Gln Met Ile
145                 150                 155                 160

Pro Glu Asn Lys Tyr Phe His His Met Gly Lys Cys Cys Pro Asp Ser
                165                 170                 175

Glu Phe

<210> SEQ ID NO 7
<211> LENGTH: 172
<212> TYPE: PRT
<213> ORGANISM: Homo sapiens

<400> SEQUENCE: 7

Met Glu Gly Asp Phe Ser Val Cys Arg Asn Cys Lys Arg His Val Val
1               5                   10                  15

Ser Ala Asn Phe Thr Leu His Glu Ala Tyr Cys Leu Arg Phe Leu Val
            20                  25                  30

Leu Cys Pro Glu Cys Glu Glu Pro Val Pro Lys Glu Thr Met Glu Glu
        35                  40                  45

His Cys Lys Leu Glu His Gln Gln Val Gly Cys Thr Met Cys Gln Gln
    50                  55                  60

Ser Met Gln Lys Ser Ser Leu Glu Phe His Lys Ala Asn Glu Cys Gln
65                  70                  75                  80

Glu Arg Pro Val Glu Cys Lys Phe Cys Lys Leu Asp Met Gln Leu Ser
                85                  90                  95

Lys Leu Glu Leu His Glu Ser Tyr Cys Gly Ser Arg Thr Glu Leu Cys
            100                 105                 110

Gln Gly Cys Gly Gln Phe Ile Met His Arg Met Leu Ala Gln His Arg
        115                 120                 125

Asp Val Cys Arg Ser Glu Gln Ala Gln Leu Gly Lys Gly Glu Arg Ile
    130                 135                 140

Ser Ala Pro Glu Arg Glu Ile Tyr Cys His Tyr Cys Asn Gln Met Ile
145                 150                 155                 160

Pro Glu Asn Lys Tyr Phe His His Met Gly Lys Cys
                165                 170

<210> SEQ ID NO 8
<211> LENGTH: 145
<212> TYPE: PRT
<213> ORGANISM: Homo sapiens
```

<400> SEQUENCE: 8

| | | | | | | | | | | | | | | |
|---|---|---|---|---|---|---|---|---|---|---|---|---|---|---|
| Cys | Pro | Asp | Ser | Glu | Phe | Lys | Lys | His | Phe | Pro | Val | Gly | Asn | Pro | Glu |
| 1 | | | | 5 | | | | | 10 | | | | | 15 | |
| Ile | Leu | Pro | Ser | Ser | Leu | Pro | Ser | Gln | Ala | Ala | Glu | Asn | Gln | Thr | Ser |
| | | | 20 | | | | | 25 | | | | | 30 | | |
| Thr | Met | Glu | Lys | Asp | Val | Arg | Pro | Lys | Thr | Arg | Ser | Ile | Asn | Arg | Phe |
| | | 35 | | | | | 40 | | | | | 45 | | | |
| Pro | Leu | His | Ser | Glu | Ser | Ser | Ser | Lys | Lys | Ala | Pro | Arg | Ser | Lys | Asn |
| | 50 | | | | | 55 | | | | | 60 | | | | |
| Lys | Thr | Leu | Asp | Pro | Leu | Leu | Met | Ser | Glu | Pro | Lys | Pro | Arg | Thr | Ser |
| 65 | | | | | 70 | | | | | 75 | | | | | 80 |
| Ser | Pro | Arg | Gly | Asp | Lys | Ala | Ala | Tyr | Asp | Ile | Leu | Arg | Arg | Cys | Ser |
| | | | | 85 | | | | | 90 | | | | | 95 | |
| Gln | Cys | Gly | Ile | Leu | Leu | Pro | Leu | Pro | Ile | Leu | Asn | Gln | His | Gln | Glu |
| | | | 100 | | | | | 105 | | | | | 110 | | |
| Lys | Cys | Arg | Trp | Leu | Ala | Ser | Ser | Lys | Arg | Lys | Thr | Ser | Glu | Lys | Phe |
| | | 115 | | | | | 120 | | | | | 125 | | | |
| Gln | Leu | Asp | Leu | Glu | Lys | Glu | Arg | Tyr | Tyr | Lys | Phe | Lys | Arg | Phe | His |
| | 130 | | | | | 135 | | | | | 140 | | | | |
| Phe | | | | | | | | | | | | | | | |
| 145 | | | | | | | | | | | | | | | |

<210> SEQ ID NO 9
<211> LENGTH: 2643
<212> TYPE: DNA
<213> ORGANISM: Homo sapiens

<400> SEQUENCE: 9

```
gcagctagtg tgtcatttca gcgtttctcc tctcgtccct ggaagagcta aagatggctg      60
aatttctaga tgaccaggaa actcgactgt gtgacaactg caaaaaagaa attcctgtgt     120
ttaactttac catccatgag atccactgtc aaaggaacat tggtatgtgt cctacctgta     180
aggaaccatt tcccaaatct gacatggaga ctcacatggc tgcagaacac tgtcaggtga     240
cctgcaaatg taacaagaag ttggagaaga ggctgttaaa gaagcatgag gagactgagt     300
gcccttttgcg gcttgctgtc tgccagcact gtgatttaga actttccatt ctcaaactga     360
aggaacatga agattattgt ggtgcccgga cggaactatg tggcaactgt ggtcgcaatg     420
tccttgtgaa agatctgaag actcaccctg aagtttgtgg agagaggggg aggaaaaga      480
gaaatgaggt tgccatacct cctaatgcat atgatgaatc ttggggtcag gatggaatct     540
ggattgcatc ccaactcctc agacaaattg aggctctgga cccacccatg aggctgccgc     600
gaaggcccct gagagccttt gaatcagatg tttttccacaa tagaactacc aaccaaagga     660
acattacagc ccaggtttca attcagaata atctgtttga agaacaagag aggcaggaaa     720
ggaatagagg ccaacagccc cccaaagagg gtggtgaaga gagtgcaaac ttggacttca     780
tgttggcccct aagtctgcaa aatgaaggcc aagcctccag tgtggcagag caggacttct     840
ggagggccgt atgtgaggcc gaccagtctc atggcggtcc caggtctctc agtgacataa     900
agggtgcagc tgacgagatc atgttgcctt gtgaattttg tgaggagctc tacccagagg     960
aactgctgat tgaccatcag acaagctgta acccttcacg tgccttacct tcactcaata    1020
ctggcagctc ttcccccaga gggtggagg aacctgatgt catcttccag aacttcttgc     1080
aacaggctgc aagtaaccag ttagactctt tgatgggcct gagcaattca caccctgtgg    1140
```

-continued

```
aggagagcat cattatccca tgtgaattct gtggggtaca gctggaagag gaggtgctgt    1200
tccatcacca ggaccagtgt gaccaacgcc cagccactgc aaccaaccat gtgacagagg    1260
ggattcctag actggattcc cagcctcaag agacccacc agagctgccc aggaggcgtg     1320
tcagacacca gggagacctg tcttctggtt acctggatga tactaagcag gaaacagcta    1380
atgggcccac ctcctgtctg cctcccagcc gacccattaa caatatgaca gctacctata    1440
accagctatc gagatcaaca tcaggcccca gacctgggtg ccagcccagc tctccttgtg    1500
tgccgaagct cagcaactca gacagccagg acatccaggg gcggaatcga gacagccaga    1560
atggggccat agcccctggg cacgtttcag tgattcgccc tcctcaaaat ctctacccag    1620
aaaacattgt gccctctttc tcccctgggc cttcagggag atacggagct agtggtagga    1680
gtgaaggtgg caggaattcc cgggtcaccc ctgcagctgc caactaccgc agcagaactg    1740
caaaggcaaa gccttccaag aacagggag ctggggatgc agaagaggaa gaggaggagt     1800
aatggtgtct ccagagactt tacatcggtt cctgtcttct gtgcacagca gcacttgccg    1860
ctgtgcaggc ccacctcttt ggctcttttgg gtgggagagt ttttccagat tttagatttt   1920
tctaggttat ggccattttg tgtcttttga ggttgtgctg tgggggtttg ggtttgaggg    1980
aagggagcag ggtggcggtt gaggaacgct tcagccttag ctgctacctt tcggcagcag    2040
tgaaatacaa gctgcagcct cggctgccag ggctccctt tgacttattg tcgccactgc     2100
cccttggtgc tgtgtggtcc cagtggaagg aggggaagat tttggaaacc tggtagccac    2160
cagtaaggtg attctctgcc ctgttgggc ctaaatttgg gggcttttgg gcaacctctc     2220
cgtgtactgc gtctgtccac actcgattgg gccccaggtg tgtatgaggc gctctggtaa    2280
ggtgctcagg ccagttgcaa tgtctgtcag taacgaggct tttgatgtgt tgagctggag    2340
gtgagtggac cgggggctgt gttttaagct gcttccttgg catttggcat cactgccttc    2400
tgttcccggg ggagcatgga tcttttgtcc tcactgcttt ctaatgggga gggctgaggg    2460
ctccctgtcc ccacagcagg tatggttgct ctgccccagc cccacacttg ctctgaaaac    2520
caagtgtcag agcccttcc ccttgttttt attttactgt tataataatt attaacttcc     2580
ttgtaataga aataaagttt gtacttggaa aaaaaaaaa aaaaaaaaa aaaaaaaaa       2640 aaa                                                                  2643
```

<210> SEQ ID NO 10
<211> LENGTH: 582
<212> TYPE: PRT
<213> ORGANISM: Homo sapiens

<400> SEQUENCE: 10

```
Met Ala Glu Phe Leu Asp Asp Gln Glu Thr Arg Leu Cys Asp Asn Cys
 1               5                  10                  15

Lys Lys Glu Ile Pro Val Phe Asn Phe Thr Ile His Glu Ile His Cys
            20                  25                  30

Gln Arg Asn Ile Gly Met Cys Pro Thr Cys Lys Glu Pro Phe Pro Lys
        35                  40                  45

Ser Asp Met Glu Thr His Met Ala Ala Glu His Cys Gln Val Thr Cys
    50                  55                  60

Lys Cys Asn Lys Lys Leu Glu Lys Arg Leu Leu Lys His Glu Glu
65                  70                  75                  80

Thr Glu Cys Pro Leu Arg Leu Ala Val Cys Gln His Cys Asp Leu Glu
                85                  90                  95

Leu Ser Ile Leu Lys Leu Lys Glu His Glu Asp Tyr Cys Gly Ala Arg
```

-continued

```
            100                 105                 110
Thr Glu Leu Cys Gly Asn Cys Gly Arg Asn Val Leu Val Lys Asp Leu
            115                 120                 125
Lys Thr His Pro Glu Val Cys Gly Arg Glu Gly Glu Lys Arg Asn
    130                 135             140
Glu Val Ala Ile Pro Pro Asn Ala Tyr Asp Glu Ser Trp Gly Gln Asp
145                 150                 155                 160
Gly Ile Trp Ile Ala Ser Gln Leu Leu Arg Gln Ile Glu Ala Leu Asp
                165                 170                 175
Pro Pro Met Arg Leu Pro Arg Arg Pro Leu Arg Ala Phe Glu Ser Asp
            180                 185                 190
Val Phe His Asn Arg Thr Thr Asn Gln Arg Asn Ile Thr Ala Gln Val
        195                 200                 205
Ser Ile Gln Asn Asn Leu Phe Glu Glu Gln Glu Arg Gln Glu Arg Asn
    210                 215                 220
Arg Gly Gln Gln Pro Pro Lys Glu Gly Gly Glu Ser Ala Asn Leu
225                 230                 235                 240
Asp Phe Met Leu Ala Leu Ser Leu Gln Asn Glu Gly Gln Ala Ser Ser
                245                 250                 255
Val Ala Glu Gln Asp Phe Trp Arg Ala Val Cys Glu Ala Asp Gln Ser
            260                 265                 270
His Gly Gly Pro Arg Ser Leu Ser Asp Ile Lys Gly Ala Ala Asp Glu
        275                 280                 285
Ile Met Leu Pro Cys Glu Phe Cys Glu Glu Leu Tyr Pro Glu Glu Leu
    290                 295                 300
Leu Ile Asp His Gln Thr Ser Cys Asn Pro Ser Arg Ala Leu Pro Ser
305                 310                 315                 320
Leu Asn Thr Gly Ser Ser Ser Pro Arg Gly Val Glu Glu Pro Asp Val
                325                 330                 335
Ile Phe Gln Asn Phe Leu Gln Gln Ala Ala Ser Asn Gln Leu Asp Ser
            340                 345                 350
Leu Met Gly Leu Ser Asn Ser His Pro Val Glu Glu Ser Ile Ile Ile
        355                 360                 365
Pro Cys Glu Phe Cys Gly Val Gln Leu Glu Glu Glu Val Leu Phe His
    370                 375                 380
His Gln Asp Gln Cys Asp Gln Arg Pro Ala Thr Ala Thr Asn His Val
385                 390                 395                 400
Thr Glu Gly Ile Pro Arg Leu Asp Ser Gln Pro Gln Glu Thr Pro Pro
                405                 410                 415
Glu Leu Pro Arg Arg Arg Val Arg His Gln Gly Asp Leu Ser Ser Gly
            420                 425                 430
Tyr Leu Asp Asp Thr Lys Gln Glu Thr Ala Asn Gly Pro Thr Ser Cys
        435                 440                 445
Leu Pro Pro Ser Arg Pro Ile Asn Asn Met Thr Ala Thr Tyr Asn Gln
    450                 455                 460
Leu Ser Arg Ser Thr Ser Gly Pro Arg Gly Cys Gln Pro Ser Ser
465                 470                 475                 480
Pro Cys Val Pro Lys Leu Ser Asn Ser Asp Ser Gln Asp Ile Gln Gly
                485                 490                 495
Arg Asn Arg Asp Ser Gln Asn Gly Ala Ile Ala Pro Gly His Val Ser
            500                 505                 510
Val Ile Arg Pro Pro Gln Asn Leu Tyr Pro Glu Asn Ile Val Pro Ser
        515                 520                 525
```

-continued

```
Phe Ser Pro Gly Pro Ser Gly Arg Tyr Gly Ala Ser Gly Arg Ser Glu
        530                 535                 540
Gly Gly Arg Asn Ser Arg Val Thr Pro Ala Ala Ala Asn Tyr Arg Ser
545                 550                 555                 560
Arg Thr Ala Lys Ala Lys Pro Ser Lys Gln Gln Gly Ala Gly Asp Ala
                565                 570                 575
Glu Glu Glu Glu Glu Glu
            580
```

<210> SEQ ID NO 11
<211> LENGTH: 1302
<212> TYPE: DNA
<213> ORGANISM: Homo sapiens

<400> SEQUENCE: 11

```
gcagctagtg tgtcatttca gcgtttctcc tctcgtccct ggaagagcta aagatggctg      60
aatttctaga tgaccaggaa actcgactgt gtgacaactg caaaaaagaa attcctgtgt     120
ttaactttac catccatgag atccactgtc aaaggaacat tggtatgtgt cctacctgta     180
aggaaccatt tcccaaatct gacatggaga ctcacatggc tgcagaacac tgtcaggtga     240
cctgcaaatg taacaagaag ttggagaaga ggctgttaaa gaagcatgag agactgagt      300
gcccttttgcg gcttgctgtc tgccagcact gtgatttaga actttccatt ctcaaactga     360
aggtcacccc tgcagctgcc aactaccgca gcagaactgc aaaggcaaag ccttccaagc     420
aacagggagc tggggatgca gaagaggaag aggaggagta atggtgtctc cagagacttt     480
acatcggttc ctgtcttctg tgcacagcag cacttgccgc tgtgcaggcc cacctctttg     540
gctctttggg tgggagagtt tttccagatt ttagatttt ctaggttatg ccatttttgt     600
gtcttttgag gttgtgctgt gggggtttgg gtttgaggga agggagcagg gtggcggttg     660
aggaacgctt cagccttagc tgctaccttt cggcagcagt gaaatacaag ctgcagcctc     720
ggctgccagg gctccctttt gacttattgt cgccactgcc ccttggtgct gtgtggtccc     780
agtggaagga ggggaagatt ttggaaacct ggtagccacc agtaaggtga ttctctgccc     840
tgttggggcc taaatttggg ggcttttggg caacctctcc gtgtactgcg tctgtccaca     900
ctcgattggg ccccaggtgt gtatgaggcg ctctggtaag gtgctcaggc cagttgcaat     960
gtctgtcagt aacgaggctt ttgatgtgtt gagctggagg tgagtggacc gggggctgtg    1020
ttttaagctg cttccttggc atttggcatc actgccttct gttcccgggg gagcatggat    1080
cttttgtcct cactgctttc taatggggag ggctgagggc tccctgtccc cacagcaggt    1140
atggttgctc tgccccagcc ccacacttgc tctgaaaacc aagtgtcaga gccccttccc    1200
cttgttttta ttttactgtt ataataatta ttaacttcct tgtaatagaa ataaagtttg    1260
tacttggaaa aaaaaaaaa aaaaaaaaa aaaaaaaaa aa                          1302
```

<210> SEQ ID NO 12
<211> LENGTH: 135
<212> TYPE: PRT
<213> ORGANISM: Homo sapiens

<400> SEQUENCE: 12

```
Met Ala Glu Phe Leu Asp Asp Gln Glu Thr Arg Leu Cys Asp Asn Cys
  1               5                  10                  15
Lys Lys Glu Ile Pro Val Phe Asn Phe Thr Ile His Glu Ile His Cys
            20                  25                  30
```

-continued

Gln Arg Asn Ile Gly Met Cys Pro Thr Cys Lys Glu Pro Phe Pro Lys
        35                  40                  45

Ser Asp Met Glu Thr His Met Ala Ala Glu His Cys Gln Val Thr Cys
 50                  55                  60

Lys Cys Asn Lys Lys Leu Glu Lys Arg Leu Leu Lys Lys His Glu Glu
 65                  70                  75                  80

Thr Glu Cys Pro Leu Arg Leu Ala Val Cys Gln His Cys Asp Leu Glu
                 85                  90                  95

Leu Ser Ile Leu Lys Leu Lys Val Thr Pro Ala Ala Ala Asn Tyr Arg
            100                 105                 110

Ser Arg Thr Ala Lys Ala Lys Pro Ser Lys Gln Gln Gly Ala Gly Asp
        115                 120                 125

Ala Glu Glu Glu Glu Glu Glu
    130                 135

<210> SEQ ID NO 13
<211> LENGTH: 19
<212> TYPE: PRT
<213> ORGANISM: Homo sapiens
<220> FEATURE:
<221> NAME/KEY: VARIANT
<222> LOCATION: (1)...(19)
<223> OTHER INFORMATION: Xaa = Any Amino Acid; Xaa at 16 and 19 is Cys
      or His

<400> SEQUENCE: 13

Cys Xaa Xaa Cys Xaa Xaa Xaa Xaa Xaa Xaa Xaa Xaa Xaa Xaa Xaa
 1               5                  10                  15

Xaa Xaa Xaa

<210> SEQ ID NO 14
<211> LENGTH: 20
<212> TYPE: PRT
<213> ORGANISM: Homo sapiens
<220> FEATURE:
<221> NAME/KEY: VARIANT
<222> LOCATION: (1)...(20)
<223> OTHER INFORMATION: Xaa = Any Amino Acid;  Xaa at 17 and 20 is Cys
      or His

<400> SEQUENCE: 14

Cys Xaa Xaa Xaa Cys Xaa Xaa Xaa Xaa Xaa Xaa Xaa Xaa Xaa Xaa
 1               5                  10                  15

Xaa Xaa Xaa Xaa
        20

<210> SEQ ID NO 15
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = Any Amino Acid;  Xaa at 18 and 21 is Cys
      or His

<400> SEQUENCE: 15

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa
        20

<210> SEQ ID NO 16

```
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;  Xaa at 19 and 22 is Cys
      or His

<400> SEQUENCE: 16

Cys Xaa Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa
            20

<210> SEQ ID NO 17
<211> LENGTH: 20
<212> TYPE: PRT
<213> ORGANISM: Homo sapiens
<220> FEATURE:
<221> NAME/KEY: VARIANT
<222> LOCATION: (1)...(20)
<223> OTHER INFORMATION: Xaa = Any Amino Acid;  Xaa at 17 and 20 is Cys
      or His

<400> SEQUENCE: 17

Cys Xaa Xaa Cys Xaa Xaa Xaa Xaa Xaa Xaa Xaa Xaa Xaa Xaa Xaa Xaa
 1               5                  10                  15

Xaa Xaa Xaa Xaa
            20

<210> SEQ ID NO 18
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = Any Amino Acid;  Xaa at 19 and 21 is Cys
      or His

<400> SEQUENCE: 18

Cys Xaa Xaa Cys Xaa Xaa Xaa Xaa Xaa Xaa Xaa Xaa Xaa Xaa Xaa Xaa
 1               5                  10                  15

Xaa Xaa Xaa Xaa Xaa
            20

<210> SEQ ID NO 19
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;  Xaa at 19 and 22 is Cys
      or His

<400> SEQUENCE: 19

Cys Xaa Xaa Cys Xaa Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 20
<211> LENGTH: 23
<212> TYPE: PRT
```

```
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;  Xaa at 20 and 23 is Cys
      or His

<400> SEQUENCE: 20

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 21
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;  Xaa at 21 and 24 is Cys
      or His

<400> SEQUENCE: 21

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 22
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;  Xaa at 22 and 25 is Cys
      or His

<400> SEQUENCE: 22

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 23
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;  Xaa at 23 and 26 is Cys
      or His

<400> SEQUENCE: 23

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 24
<211> LENGTH: 21
<212> TYPE: PRT
<213> ORGANISM: Homo sapiens
<220> FEATURE:
<221> NAME/KEY: VARIANT
```

```
<222> LOCATION: (1)...(21)
<223> OTHER INFORMATION: Xaa = Any Amino Acid;   Xaa at 19 and 21 is Cys
      or His

<400> SEQUENCE: 24

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa
            20

<210> SEQ ID NO 25
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 19 and 22 is Cys
      or His

<400> SEQUENCE: 25

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 26
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 20 and 23 is Cys
      or His

<400> SEQUENCE: 26

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 27
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 21 and 24 is Cys
      or His

<400> SEQUENCE: 27

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 28
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 22 and 25 is Cys
      or His
```

```
<400> SEQUENCE: 28

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 29
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 23 and 26 is Cys
      or His

<400> SEQUENCE: 29

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 30
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 24 and 27 is Cys
      or His

<400> SEQUENCE: 30

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 31
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 19 and 22 is Cys
      or His

<400> SEQUENCE: 31

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa
            20

<210> SEQ ID NO 32
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 20 and 23 is Cys
      or His

<400> SEQUENCE: 32
```

-continued

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 33
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid  Xaa at 21 and 24 is Cys
      or His

<400> SEQUENCE: 33

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 34
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;  Xaa at 22 and 25 is Cys
      or His

<400> SEQUENCE: 34

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 35
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;  Xaa at 23 and 26 is Cys
      or His

<400> SEQUENCE: 35

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 36
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;  Xaa at 24 and 27 is Cys
      or His

<400> SEQUENCE: 36

Cys Xaa Xaa Xaa Xaa Cys Xaa Xaa Xaa Xaa Xaa Xaa Xaa Xaa Xaa
1               5                   10                  15

-continued

```
Xaa Xaa Xaa Xaa Xaa Xaa Xaa Xaa Xaa Xaa Xaa
            20                  25

<210> SEQ ID NO 37
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 25 and 28 is Cys
      or His

<400> SEQUENCE: 37

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 38
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 20 and 23 is Cys
      or His

<400> SEQUENCE: 38

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa
            20

<210> SEQ ID NO 39
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 21 and 24 is Cys
      or His

<400> SEQUENCE: 39

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 40
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 22 and 25 is Cys
      or His

<400> SEQUENCE: 40

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa
            20                  25
```

```
<210> SEQ ID NO 41
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 23 and 26 is Cys
      or His

<400> SEQUENCE: 41

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa
             20                  25

<210> SEQ ID NO 42
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 24 and 27 is Cys
      or His

<400> SEQUENCE: 42

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa
             20                  25

<210> SEQ ID NO 43
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 25 and 28 is Cys
      or His

<400> SEQUENCE: 43

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
             20                  25

<210> SEQ ID NO 44
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 26 and 29 is Cys
      or His

<400> SEQUENCE: 44

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
             20                  25

<210> SEQ ID NO 45
<211> LENGTH: 20
```

```
<212> TYPE: PRT
<213> ORGANISM: Homo sapiens
<220> FEATURE:
<221> NAME/KEY: VARIANT
<222> LOCATION: (1)...(20)
<223> OTHER INFORMATION: Xaa = Any Amino Acid; Xaa at 16 and 20 is Cys
      or His

<400> SEQUENCE: 45

Cys Xaa Xaa Cys Xaa Xaa Xaa Xaa Xaa Xaa Xaa Xaa Xaa Xaa Xaa
 1               5                   10                  15

Xaa Xaa Xaa Xaa
            20

<210> SEQ ID NO 46
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = Any Amino Acid;   Xaa at 17 and 21 is Cys
      or His

<400> SEQUENCE: 46

Cys Xaa Xaa Xaa Cys Xaa Xaa Xaa Xaa Xaa Xaa Xaa Xaa Xaa Xaa
 1               5                   10                  15

Xaa Xaa Xaa Xaa Xaa
                20

<210> SEQ ID NO 47
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 17 and 22 is Cys
      or His

<400> SEQUENCE: 47

Cys Xaa Xaa Xaa Xaa Cys Xaa Xaa Xaa Xaa Xaa Xaa Xaa Xaa Xaa
 1               5                   10                  15

Xaa Xaa Xaa Xaa Xaa Xaa
                20

<210> SEQ ID NO 48
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 19 and 23 is Cys
      or His

<400> SEQUENCE: 48

Cys Xaa Xaa Xaa Xaa Xaa Cys Xaa Xaa Xaa Xaa Xaa Xaa Xaa Xaa
 1               5                   10                  15

Xaa Xaa Xaa Xaa Xaa Xaa Xaa
                20

<210> SEQ ID NO 49
<211> LENGTH: 21
<212> TYPE: PRT
<213> ORGANISM: Homo sapiens
```

```
<220> FEATURE:
<221> NAME/KEY: VARIANT
<222> LOCATION: (1)...(21)
<223> OTHER INFORMATION: Xaa = Any Amino Acid;   Xaa at 17 and 21 is Cys
      or His

<400> SEQUENCE: 49

Cys Xaa Xaa Cys Xaa Xaa Xaa Xaa Xaa Xaa Xaa Xaa Xaa Xaa Xaa
  1               5                  10                  15

Xaa Xaa Xaa Xaa Xaa
            20

<210> SEQ ID NO 50
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 18 and 22 is Cys
      or His

<400> SEQUENCE: 50

Cys Xaa Xaa Cys Xaa Xaa Xaa Xaa Xaa Xaa Xaa Xaa Xaa Xaa Xaa Xaa
  1               5                  10                  15

Xaa Xaa Xaa Xaa Xaa Xaa
            20

<210> SEQ ID NO 51
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 19 and 23 is Cys
      or His

<400> SEQUENCE: 51

Cys Xaa Xaa Cys Xaa Xaa Xaa Xaa Xaa Xaa Xaa Xaa Xaa Xaa Xaa Xaa
  1               5                  10                  15

Xaa Xaa Xaa Xaa Xaa Xaa Xaa
            20

<210> SEQ ID NO 52
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 20 and 24 is Cys
      or His

<400> SEQUENCE: 52

Cys Xaa Xaa Cys Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa
            20

<210> SEQ ID NO 53
<211> LENGTH: 25
<212> TYPE: PRT
<213> ORGANISM: Homo sapiens
<220> FEATURE:
<221> NAME/KEY: VARIANT
<222> LOCATION: (1)...(25)
```

```
<223> OTHER INFORMATION: Xaa = Any Amino Acid;   Xaa at 21 and 25 is Cys
      or His

<400> SEQUENCE: 53

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 54
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 22 and 26 is Cys
      or His

<400> SEQUENCE: 54

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 55
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 23 and 27 is Cys
      or His

<400> SEQUENCE: 55

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 56
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 18 and 22 is Cys
      or His

<400> SEQUENCE: 56

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 57
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 19 and 23 is Cys
      or His
```

-continued

```
<400> SEQUENCE: 57

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 58
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;  Xaa at 20 and 24 is Cys
      or His

<400> SEQUENCE: 58

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 59
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;  Xaa at 21 and 24 is Cys
      or His

<400> SEQUENCE: 59

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 60
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;  Xaa at 22 and 26 is Cys
      or His

<400> SEQUENCE: 60

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 61
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;  Xaa at 23 and 27 is Cys
      or His

<400> SEQUENCE: 61

Cys Xaa Xaa Xaa Cys Xaa Xaa Xaa Xaa Xaa Xaa Xaa Xaa Xaa Xaa
```

```
                1               5                  10                 15
Xaa Xaa Xaa Xaa Xaa Xaa Xaa Xaa Xaa Xaa Xaa
            20                  25

<210> SEQ ID NO 62
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 24 and 28 is Cys
      or His

<400> SEQUENCE: 62

Cys Xaa Xaa Xaa Cys Xaa Xaa Xaa Xaa Xaa Xaa Xaa Xaa Xaa Xaa
 1               5                  10                 15

Xaa Xaa Xaa Xaa Xaa Xaa Xaa Xaa Xaa Xaa Xaa Xaa
            20                  25

<210> SEQ ID NO 63
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 19 and 23 is Cys
      or His

<400> SEQUENCE: 63

Cys Xaa Xaa Xaa Xaa Cys Xaa Xaa Xaa Xaa Xaa Xaa Xaa Xaa Xaa
 1               5                  10                 15

Xaa Xaa Xaa Xaa Xaa Xaa Xaa
            20

<210> SEQ ID NO 64
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 20 and 24 is Cys
      or His

<400> SEQUENCE: 64

Cys Xaa Xaa Xaa Xaa Cys Xaa Xaa Xaa Xaa Xaa Xaa Xaa Xaa Xaa
 1               5                  10                 15

Xaa Xaa Xaa Xaa Xaa Xaa Xaa Xaa
            20

<210> SEQ ID NO 65
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 21 and 25 is Cys
      or His

<400> SEQUENCE: 65

Cys Xaa Xaa Xaa Xaa Cys Xaa Xaa Xaa Xaa Xaa Xaa Xaa Xaa Xaa
 1               5                  10                 15

Xaa Xaa Xaa Xaa Xaa Xaa Xaa Xaa Xaa
```

20                  25

<210> SEQ ID NO 66
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 22 and 26 is Cys
      or His

<400> SEQUENCE: 66

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 67
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 23 and 27 is Cys
      or His

<400> SEQUENCE: 67

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 68
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 24 and 28 is Cys
      or His

<400> SEQUENCE: 68

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 69
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 25 and 29 is Cys
      or His

<400> SEQUENCE: 69

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

```
<210> SEQ ID NO 70
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 20 and 24 is Cys
      or His

<400> SEQUENCE: 70

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 71
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 21 and 25 is Cys
      or His

<400> SEQUENCE: 71

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 72
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 22 and 26 is Cys
      or His

<400> SEQUENCE: 72

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 73
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 23 and 27 is Cys
      or His

<400> SEQUENCE: 73

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 74
<211> LENGTH: 28
<212> TYPE: PRT
```

```
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 24 and 28 is Cys
      or His

<400> SEQUENCE: 74

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 75
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 25 and 29 is Cys
      or His

<400> SEQUENCE: 75

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
            20                  25

<210> SEQ ID NO 76
<211> LENGTH: 30
<212> TYPE: PRT
<213> ORGANISM: Homo sapiens
<220> FEATURE:
<221> NAME/KEY: VARIANT
<222> LOCATION: (1)...(30)
<223> OTHER INFORMATION: Xaa = Any Amino Acid;   Xaa at 26 and 30 is Cys
      or His

<400> SEQUENCE: 76

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

<210> SEQ ID NO 77
<211> LENGTH: 22
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = Any Amino Acid;   Xaa at 16 and 21 is Cys
      or His

<400> SEQUENCE: 77

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 78
<211> LENGTH: 22
<212> TYPE: PRT
<213> ORGANISM: Homo sapiens
<220> FEATURE:
<221> NAME/KEY: VARIANT
```

```
<222> LOCATION: (1)...(22)
<223> OTHER INFORMATION: Xaa = Any Amino Acid;   Xaa at 17 and 22 is Cys
      or His

<400> SEQUENCE: 78

Cys Xaa Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 79
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 18 and 23 is Cys
      or His

<400> SEQUENCE: 79

Cys Xaa Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 80
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 80

Cys Xaa Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 81
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 17 and 22 is Cys
      or His

<400> SEQUENCE: 81

Cys Xaa Xaa Cys Xaa Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 82
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 18 and 23 is Cys
      or His
```

<400> SEQUENCE: 82

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 83
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 83

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 84
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 84

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 85
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 85

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 86
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 86

```
Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 87
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 87

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 88
<211> LENGTH: 23
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 16 and 22 is Cys
      or His

<400> SEQUENCE: 88

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 89
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 89

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 90
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 90

Cys Xaa Xaa Xaa Cys Xaa Xaa Xaa Xaa Xaa Xaa Xaa Xaa Xaa Xaa
 1               5                  10                  15
```

-continued

Xaa Xaa Xaa Xaa Xaa Xaa Xaa Xaa Xaa
            20                  25

<210> SEQ ID NO 91
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 91

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 92
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 92

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 93
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 93

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 94
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 94

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

```
<210> SEQ ID NO 95
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 95

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 96
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 96

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 97
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 97

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 98
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 98

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 99
<211> LENGTH: 28
```

```
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 99

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 100
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 100

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
            20                  25

<210> SEQ ID NO 101
<211> LENGTH: 30
<212> TYPE: PRT
<213> ORGANISM: Homo sapiens
<220> FEATURE:
<221> NAME/KEY: VARIANT
<222> LOCATION: (1)...(30)
<223> OTHER INFORMATION: Xaa = Any Amino Acid;   Xaa at 25 and 30 is Cys
      or His

<400> SEQUENCE: 101

Cys Xaa Xaa Xaa Xaa Cys Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

<210> SEQ ID NO 102
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 102

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 103
<211> LENGTH: 26
<212> TYPE: PRT
<213> ORGANISM: Homo sapiens
<220> FEATURE:
```

-continued

```
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 103

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 104
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 104

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 105
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28is Cys
      or His

<400> SEQUENCE: 105

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 106
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 106

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 107
<211> LENGTH: 30
<212> TYPE: PRT
<213> ORGANISM: Homo sapiens
<220> FEATURE:
<221> NAME/KEY: VARIANT
<222> LOCATION: (1)...(30)
<223> OTHER INFORMATION: Xaa = Any Amino Acid;   Xaa at 25 and 30 is Cys
``` or His

<400> SEQUENCE: 107

Cys Xaa Xaa Xaa Xaa Xaa Cys Xaa Xaa Xaa Xaa Xaa Xaa Xaa Xaa
1               5                  10                 15

Xaa Xaa Xaa Xaa Xaa Xaa Xaa Xaa Xaa Xaa Xaa Xaa Xaa Xaa
            20                  25                 30

<210> SEQ ID NO 108
<211> LENGTH: 31
<212> TYPE: PRT
<213> ORGANISM: Homo sapiens
<220> FEATURE:
<221> NAME/KEY: VARIANT
<222> LOCATION: (1)...(31)
<223> OTHER INFORMATION: Xaa = Any Amino Acid;   Xaa at 26 and 31 is Cys
      or His

<400> SEQUENCE: 108

Cys Xaa Xaa Xaa Xaa Xaa Cys Xaa Xaa Xaa Xaa Xaa Xaa Xaa Xaa
1               5                  10                 15

Xaa Xaa Xaa Xaa Xaa Xaa Xaa Xaa Xaa Xaa Xaa Xaa Xaa Xaa Xaa
            20                  25                 30

<210> SEQ ID NO 109
<211> LENGTH: 22
<212> TYPE: PRT
<213> ORGANISM: Homo sapiens
<220> FEATURE:
<221> NAME/KEY: VARIANT
<222> LOCATION: (1)...(22)
<223> OTHER INFORMATION: Xaa = Any Amino Acid;   Xaa at 17 and 22 is Cys
      or His

<400> SEQUENCE: 109

Cys Xaa Xaa Cys Xaa Xaa Xaa Xaa Xaa Xaa Xaa Xaa Xaa Xaa Xaa
1               5                  10                 15

Xaa Xaa Xaa Xaa Xaa Xaa
            20

<210> SEQ ID NO 110
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 18 and 23 is Cys
      or His

<400> SEQUENCE: 110

Cys Xaa Xaa Xaa Cys Xaa Xaa Xaa Xaa Xaa Xaa Xaa Xaa Xaa Xaa
1               5                  10                 15

Xaa Xaa Xaa Xaa Xaa Xaa Xaa
            20

<210> SEQ ID NO 111
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 111

```
Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 112
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 112

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 113
<211> LENGTH: 23
<212> TYPE: PRT
<213> ORGANISM: Homo sapiens
<220> FEATURE:
<221> NAME/KEY: VARIANT
<222> LOCATION: (1)...(23)
<223> OTHER INFORMATION: Xaa = Any Amino Acid;   Xaa at 18 and 23 is Cys
      or His

<400> SEQUENCE: 113

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 114
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;   Xaa at 19 and 24 is Cys
      or His

<400> SEQUENCE: 114

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 115
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 115

Cys Xaa Xaa Cys Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa
            20                  25

<210> SEQ ID NO 116
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 25 is Cys
      or His

<400> SEQUENCE: 116

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 117
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 117

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 118
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 118

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 119
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 119

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25
```

<210> SEQ ID NO 120
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Any Amino Acid;  Xaa at 19 and 24 is Cys
      or His

<400> SEQUENCE: 120

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 121
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;  Xaa at 20 and 25 is Cys
      or His

<400> SEQUENCE: 121

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 122
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;  Xaa at 21 and 26 is Cys
      or His

<400> SEQUENCE: 122

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 123
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;  Xaa at 22 and 27 is Cys
      or His

<400> SEQUENCE: 123

Cys Xaa Xaa Xaa Cys Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 124

<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 124

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 125
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 125

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 126
<211> LENGTH: 30
<212> TYPE: PRT
<213> ORGANISM: Homo sapiens
<220> FEATURE:
<221> NAME/KEY: VARIANT
<222> LOCATION: (1)...(30)
<223> OTHER INFORMATION: Xaa = Any Amino Acid;   Xaa at 25 and 30 is Cys
      or His

<400> SEQUENCE: 126

Cys Xaa Xaa Xaa Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 127
<211> LENGTH: 25
<212> TYPE: PRT
<213> ORGANISM: Homo sapiens
<220> FEATURE:
<221> NAME/KEY: VARIANT
<222> LOCATION: (1)...(25)
<223> OTHER INFORMATION: Xaa = Any Amino Acid;   Xaa at 20 and 25 is Cys
      or His

<400> SEQUENCE: 127

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 128
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 128

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 129
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 129

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 130
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 23 and 28 is Cys
      or His

<400> SEQUENCE: 130

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 131
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 24 and 29 is Cys
      or His

<400> SEQUENCE: 131

Cys Xaa Xaa Xaa Xaa Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 132
<211> LENGTH: 30
<212> TYPE: PRT
<213> ORGANISM: Homo sapiens
<220> FEATURE:
<221> NAME/KEY: VARIANT
<222> LOCATION: (1)...(30)

<223> OTHER INFORMATION: Xaa = Any Amino Acid;   Xaa at 25 and 30 is Cys
      or His

<400> SEQUENCE: 132

Cys Xaa Xaa Xaa Xaa Cys Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa
             20                  25                  30

<210> SEQ ID NO 133
<211> LENGTH: 31
<212> TYPE: PRT
<213> ORGANISM: Homo sapiens
<220> FEATURE:
<221> NAME/KEY: VARIANT
<222> LOCATION: (1)...(31)
<223> OTHER INFORMATION: Xaa = Any Amino Acid;   Xaa at 26 and 31 is Cys
      or His

<400> SEQUENCE: 133

Cys Xaa Xaa Xaa Xaa Cys Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa
             20                  25                  30

<210> SEQ ID NO 134
<211> LENGTH: 26
<212> TYPE: PRT
<213> ORGANISM: Homo sapiens
<220> FEATURE:
<221> NAME/KEY: VARIANT
<222> LOCATION: (1)...(26)
<223> OTHER INFORMATION: Xaa = Any Amino Acid;   Xaa at 21 and 26 is Cys
      or His

<400> SEQUENCE: 134

Cys Xaa Xaa Xaa Xaa Xaa Cys Xaa Xaa Xaa Xaa Xaa Xaa Xaa Xaa
  1               5                  10                  15

Xaa Xaa Xaa Xaa Xaa Xaa Xaa Xaa Xaa Xaa
             20                  25

<210> SEQ ID NO 135
<211> LENGTH: 27
<212> TYPE: PRT
<213> ORGANISM: Homo sapiens
<220> FEATURE:
<221> NAME/KEY: VARIANT
<222> LOCATION: (1)...(27)
<223> OTHER INFORMATION: Xaa = Any Amino Acid;   Xaa at 22 and 27 is Cys
      or His

<400> SEQUENCE: 135

Cys Xaa Xaa Xaa Xaa Xaa Cys Xaa Xaa Xaa Xaa Xaa Xaa Xaa Xaa
  1               5                  10                  15

Xaa Xaa Xaa Xaa Xaa Xaa Xaa Xaa Xaa Xaa Xaa
             20                  25

<210> SEQ ID NO 136
<211> LENGTH: 28
<212> TYPE: PRT
<213> ORGANISM: Homo sapiens
<220> FEATURE:
<221> NAME/KEY: VARIANT
<222> LOCATION: (1)...(28)
<223> OTHER INFORMATION: Xaa = Any Amino Acid;   Xaa at 22 and 28 is Cys
      or His

```
<400> SEQUENCE: 136

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 137
<211> LENGTH: 29
<212> TYPE: PRT
<213> ORGANISM: Homo sapiens
<220> FEATURE:
<221> NAME/KEY: VARIANT
<222> LOCATION: (1)...(29)
<223> OTHER INFORMATION: Xaa = Any Amino Acid;   Xaa at 25 and 29 is Cys
      or His

<400> SEQUENCE: 137

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 138
<211> LENGTH: 30
<212> TYPE: PRT
<213> ORGANISM: Homo sapiens
<220> FEATURE:
<221> NAME/KEY: VARIANT
<222> LOCATION: (1)...(30)
<223> OTHER INFORMATION: Xaa = Any Amino Acid;   Xaa at 25 and 30 is Cys
      or His

<400> SEQUENCE: 138

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

<210> SEQ ID NO 139
<211> LENGTH: 31
<212> TYPE: PRT
<213> ORGANISM: Homo sapiens
<220> FEATURE:
<221> NAME/KEY: VARIANT
<222> LOCATION: (1)...(31)
<223> OTHER INFORMATION: Xaa = Any Amino Acid;   Xaa at 26 and 31 is Cys
      or His

<400> SEQUENCE: 139

Cys Xaa Xaa Xaa Xaa Xaa Cys Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

<210> SEQ ID NO 140
<211> LENGTH: 32
<212> TYPE: PRT
<213> ORGANISM: Homo sapiens
<220> FEATURE:
<221> NAME/KEY: VARIANT
<222> LOCATION: (1)...(32)
<223> OTHER INFORMATION: Xaa = Any Amino Acid;   Xaa at 27 and 32 is Cys
      or His

<400> SEQUENCE: 140

Cys Xaa Xaa Xaa Xaa Xaa Cys Xaa Xaa Xaa Xaa Xaa Xaa Xaa Xaa
```

-continued

```
                1               5              10              15
Xaa Xaa Xaa Xaa Xaa Xaa Xaa Xaa Xaa Xaa Xaa Xaa Xaa Xaa Xaa Xaa
               20              25              30

<210> SEQ ID NO 141
<211> LENGTH: 19
<212> TYPE: PRT
<213> ORGANISM: Homo sapiens
<220> FEATURE:
<221> NAME/KEY: VARIANT
<222> LOCATION: (1)...(19)
<223> OTHER INFORMATION: Xaa = Any Amino Acid

<400> SEQUENCE: 141

Cys Xaa Cys Xaa Xaa Xaa Xaa Xaa Xaa Xaa Xaa Xaa Xaa Xaa His Xaa
  1               5              10              15

Xaa Xaa Cys

<210> SEQ ID NO 142
<211> LENGTH: 20
<212> TYPE: PRT
<213> ORGANISM: Homo sapiens
<220> FEATURE:
<221> NAME/KEY: VARIANT
<222> LOCATION: (1)...(20)
<223> OTHER INFORMATION: Xaa = Any Amino Acid

<400> SEQUENCE: 142

Cys Xaa Cys Xaa Xaa Xaa Xaa Xaa Xaa Xaa Xaa Xaa Xaa Xaa His Xaa
  1               5              10              15

Xaa Xaa Xaa Cys
               20

<210> SEQ ID NO 143
<211> LENGTH: 21
<212> TYPE: PRT
<213> ORGANISM: Homo sapiens
<220> FEATURE:
<221> NAME/KEY: VARIANT
<222> LOCATION: (1)...(21)
<223> OTHER INFORMATION: Xaa = Any Amino Acid

<400> SEQUENCE: 143

Cys Xaa Cys Xaa Xaa Xaa Xaa Xaa Xaa Xaa Xaa Xaa Xaa Xaa His Xaa
  1               5              10              15

Xaa Xaa Xaa Xaa Cys
               20
```